(12) United States Patent
Suessmuth et al.

(10) Patent No.: US 11,358,987 B2
(45) Date of Patent: Jun. 14, 2022

(54) ALBICIDIN DERIVATIVES, THEIR USE AND SYNTHESIS

(71) Applicant: TECHNISCHE UNIVERSITÄT BERLIN, Berlin (DE)

(72) Inventors: Roderich Suessmuth, Berlin (DE); Stefan Graetz, Berlin (DE); Iraj Behroz, Berlin (DE); Leonard Von Eckardstein, Berlin (DE); Patrick Michael Durkin, Berlin (DE); John Weston, Kelkheim (DE); Lieby Zborovsky, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 17/042,815

(22) PCT Filed: Mar. 28, 2019

(86) PCT No.: PCT/EP2019/057877
§ 371 (c)(1),
(2) Date: Sep. 28, 2020

(87) PCT Pub. No.: WO2019/185806
PCT Pub. Date: Oct. 3, 2019

(65) Prior Publication Data
US 2021/0017229 A1 Jan. 21, 2021

(30) Foreign Application Priority Data
Mar. 29, 2018 (EP) .................... 18165020

(51) Int. Cl.
*C07K 7/06* (2006.01)
*A61P 31/04* (2006.01)

(52) U.S. Cl.
CPC ............ *C07K 7/06* (2013.01); *A61P 31/04* (2018.01)

(58) Field of Classification Search
CPC ......... C07K 7/06; A61P 31/04; C07D 403/14; C07D 403/12; C07D 401/12
See application file for complete search history.

(56) References Cited

U.S. PATENT DOCUMENTS

2015/0376120 A1* 12/2015 Sussmuth .............. A61P 31/06
544/163

FOREIGN PATENT DOCUMENTS

WO        2014125075 A1    8/2014

OTHER PUBLICATIONS von Eckardstein et al. "Total Synthesis and Biological Assessment of Novel Albicidins Discovered by Mass Spectrometric Networking", Chemistry—A European Journal, vol. 23, No. 61, 2017, pp. 15316-15321.
Kerwat et al. "Synthesis of Albicidin Derivatives: Assessing the Role of Nterminal Acylation on the Antibacterial Activity", Chemmedchem, vol. 11, No. 17, 2016, pp. 1899-1903.
Petras et al. "The 0-Carbamoyl-Transferase Alb15 Is Responsible for the Modification of Albicidin", ACS Chemical Biology, vol. 11, No. 5, 2016, pp. 1198-1204.
Remington's Pharmaceutical Sciences 17th Edition, Jun. 1985, p. 1418.
Testolin et al. "Structural optimization of cystobactamids, lead compounds with potent activity against Gram-negative pathogens." Poster Helmholtz Center for Infection Research, 2018.

* cited by examiner

*Primary Examiner* — Sudhakar Katakam
(74) *Attorney, Agent, or Firm* — Maschoff Brennan

(57) ABSTRACT

It is provided a chemical compound according to general formula (1)

(1)

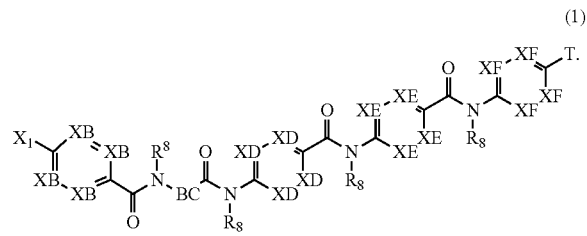

18 Claims, No Drawings

ALBICIDIN DERIVATIVES, THEIR USE AND SYNTHESIS

CROSS-REFERENCE TO A RELATED APPLICATION

This application is a National Phase Patent Application of International Patent Application Number PCT/EP2019/057877, filed on Mar. 28, 2019, which claims priority of European Patent Application Number 18 165 020.1, filed on Mar. 29, 2018.

BACKGROUND

The disclosure relates to novel albicidin derivatives.

Albicidin is a natural product, isolated from *Xanthomonas albilineans* and heterologously expressed in *Xanthomonas axonopodis* pv *vesicatoria*. Its structure (see below) is based on peptides and amino acids, but it does not contain any proteinogenic amino acids.

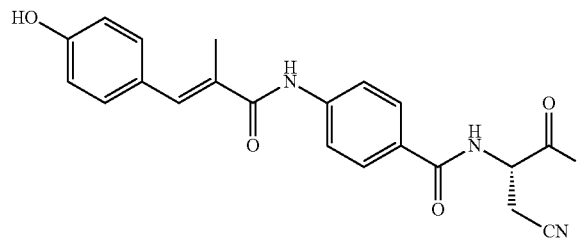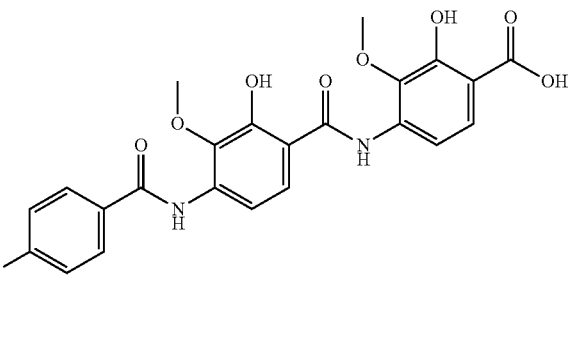

Albicidin is, on the one hand, a causative agent of the leaf scald disease in sugar cane and on the other hand a DNA-gyrase-inhibitor of prokaryotic cells (gram-positive and -negative). The mentioned properties make the natural product albicidin a potential antibiotic.

The known molecular structure of albicidin and available synthetic routes allows the development of a plurality of novel derivatives that may exhibit potential antimicrobial activities.

SUMMARY

The problem underlying the proposed solution is the provision of new compounds, which comprise antibiotic properties, a method of their synthesis and their use.

This problem is attained by a compound having the features as described herein.

Terms and Definitions

The term "purity" as used in the context of the present specification with respect to a preparation of a certain compound refers to the content of said compound relative to the sum of all compounds contained in the preparation. The term "compound" in this context is to be understood as a compound according to the general formula 1 (or any specific embodiments thereof) as well as any salts, hydrates or solvates thereof. Thus, the respective salts, hydrates or solvates are not considered as impurities according to the previous definition. The "purity" of a compound may be determined using elemental analysis, HPLC analysis using UV diode array detection also in combination with mass spectrometry detection, or quantitative NMR analysis.

The term "substituted" refers to the addition of a substituent group to a parent moiety. "Substituent groups" can be protected or unprotected and can be added to one available site or too many available sites in a parent moiety. Substituent groups may also be further substituted with other substituent groups and may be attached directly or by a linking group such as an alkyl, an amide or hydrocarbyl group to a parent moiety. "Substituent groups" amenable herein include, without limitation, halogen, subst. oxygen, subst. nitrogen, subst. sulphur, hydroxyl, alkyl, alkenyl, alkynyl, acyl (—C(O)$R^a$), carboxyl (—C(O)O$R^a$), aliphatic groups, alicyclic groups, alkoxy, substituted oxy (—O$R^a$), aryl, aralkyl, heterocyclic radical, heteroaryl, heteroarylalkyl, amino (—N($R^b$)($R^c$)), imino (=N$R^b$), amido (—C(O)N($R^b$)($R^c$) or —N($R^b$)C(O)$R^a$), hydrazine derivates —N$R^a$N$R^b R^c$, tetrazolyl (C$N_4$H), azido (—$N_3$), nitro (—$NO_2$), cyano (—CN), isocyano (—NC), cyanato (—OCN), isocyanato (—NCO), thiocyanato (—SCN); iso-thio-cyanato (—NCS); carbamido (—OC(O)N($R^b$)($R^c$) or —N($R^b$)C(O)O$R^a$), substituted thio (—S$R^b$), sulfinyl (—S(O)$R^b$), sulfonyl (—S(O)$_2 R^b$), sulfonamidyl (—S(O)$_2$N($R^b$)($R^c$) or —N($R^b$)S(O)$_2 R^b$) and fluorinated groups such as —CH$_2$CF$_3$, —CHFCF$_3$, —CF$_2$CF$_3$, —CHF$_2$, —CH$_2$F, —CF$_3$, —OCF$_3$, —SCF$_3$, —SOCF$_3$ or —SO$_2$CF$_3$. Wherein each $R^a$, $R^b$ and $R^c$ is, independently, H or a further substituent group with a preferred list including without limitation, H, alkyl, alkenyl, alkynyl, cycloalkyl, alkoxy, acyl, aryl, heteroaryl, alicyclyl, heterocyclyl and heteroarylalkyl.

As used herein the term "alkyl," refers to a saturated straight or branched hydrocarbon moiety containing up to 8, particularly up to 4 carbon atoms. Examples of alkyl groups include, without limitation, methyl, ethyl, propyl, butyl, isopropyl, n-hexyl, octyl, and the like. Alkyl groups typically include from 1 to about 8 carbon atoms ($C_1$-$C_8$ alkyl), particularly with from 1 to about 4 carbon atoms ($C_1$-$C_4$ alkyl).

As used herein the term "cycloalkyl" refers to an interconnected alkyl group forming a saturated or unsaturated ring (whereby an unsaturated cycle can also be defined as "cycloalkenyl") or polyring structure containing 3 to 10, particularly 5 to 10 carbon atoms. Examples of cycloalkyl groups include, without limitation, cyclopropyl, cyclopentyl, cyclohexyl, norbornyl, decalinyl or adamantyl (derived from tricyclo[3.3.1.1]decane), and the like. Cycloalkyl groups typically include from 5 to 10 carbon atoms ($C_5$-$C_{10}$ cycloalkyl).

Alkyl or cycloalkyl groups as used herein may optionally include further substituent groups. A substitution on the cycloalkyl group also encompasses an aryl, a heterocyclyl or a heteroaryl substituent, which can be connected to the cycloalkyl group via one atom or two atoms of the cycloalkyl group (like tetraline).

As used herein the term "haloalkyl," refers to a saturated straight or branched hydrocarbon moiety containing 1 to 8, particularly 1 to 4, carbon atoms and at least one halogen atom, in particular Cl or F, connected to a carbon atom. Examples of haloalkyl groups include, without limitation, $CF_3$, $CHF_2$, $CH_2F$, $CH_2CF_3$, $CH_2CHF_2$, $CH_2CH_2F$, $CHFCF_3$, $CHFCHF_2$, $CHFCH_2F$, $CF_2CF_3$, $CF_2CHF_2$, $CF_2CH_2F$ and the like. Haloalkyl groups typically include 1 to 4 carbon atoms ($C_1$-$C_4$ haloalkyl). More particularly haloalkyl groups comprise only F as halogen atoms.

As used herein the term "halo cycloalkyl" refers to an interconnected alkyl group forming a saturated or unsaturated ring or polyring structure containing 3 to 10, particularly 5 to 10 carbon atoms and at least one halogen atom, in particular Cl or F, connected to a carbon atom. Examples of halo cycloalkyl groups include, without limitation, fluorocyclopropyl, chlorocyclohexyl, dichlorocyclohexyl, chloroadamantyl, and the like. Halo cycloalkyl groups typically include from 5 to 10 carbon atoms ($C_5$-$C_{10}$ cycloalkyl). More particularly cyclohaloalkyl groups comprise only F as halogen atoms.

Halo alkyl or halo cycloalkyl groups as used herein may optionally include further substituent groups. A substitution on the halo cycloalkyl group also encompasses an aryl, a heterocyclyl or a heteroaryl substituent, which can be connected to the halo cycloalkyl group via one atom or two atoms of the halo cycloalkyl group (like tetraline).

As used herein the term "alkenyl" refers to a straight or branched hydrocarbon chain moiety containing up to 8 carbon atoms and having at least one carbon-carbon double bond. Examples of alkenyl groups include, without limitation, ethenyl, propenyl, butenyl, 1-methyl-2-buten-1-yl, dienyl groups such as 1,3-butadienyl and the like. Alkenyl groups typically include from 2 to about 8 carbon atoms, more typically from 2 to about 4 carbon atoms. Alkenyl groups as used herein may optionally include further substituent groups.

As used herein the term "alkynyl" refers to a straight or branched hydrocarbon moiety containing up to 8 carbon atoms and having at least one carbon-carbon triple bond. Examples of alkynyl groups include, without limitation, ethynyl, 1-propynyl, 1-butynyl, and the like. Alkynyl groups typically include from 2 to about 8 carbon atoms, more typically from 2 to about 4 carbon atoms. Alkynyl groups as used herein may optionally include further substituent groups.

As used herein the term "carboxy" refers to an carboxy (—C(=O)—O— or —O—C(=O)—) alkyl moiety containing 1 to 8, particularly 1 to 4 carbon atoms comprising at least one carboxy moiety, wherein the carboxy group is used to attach the carboxy group to a parent molecule. Examples of carboxy groups include without limitation, formate, acetate, lactate, citrate, oxalate and the like. Carboxy groups as used herein may optionally include further substituent groups. In particular "carboxy" groups include straight or branched polycarboxy groups (polyester), which comprise several interconnected monomeric carboxy groups (e. g. —C(=O)—O—$CH_2$—$CH_2$—). Non limiting examples are polyethylester or polyacrylate.

As used herein the term "alkoxy" refers to an oxygen alkyl moiety containing 1 to 8, particularly 1 to 4 carbon atoms comprising at least one oxygen moiety, wherein the oxygen atom is used to attach the alkoxy group to a parent molecule. Examples of alkoxy groups include without limitation, methoxy, ethoxy, n-propoxy, isopropoxy, n-butoxy, sec-butoxy, tert-butoxy, n-pentoxy, neopentoxy, n-hexyloxy and the like. Alkoxy groups as used herein may optionally include further substituent groups. In particular "alkoxy" groups include straight or branched polyalkoxy groups (polyether), which comprise several interconnected monomer alkoxy groups (e. g. —O—$CH_2$—$CH_2$—). Non limiting examples are groups derived from polyethyleneglycol (PEG) or polypropylenglycol (PPG).

As used herein the term "heterocyclyl" refers to an interconnected alkyl group forming a saturated or unsaturated ring or polyring structure containing 3 to 10, particularly 5 to 10 carbon atoms in which at least one carbon atom is replaced with an oxygen, a nitrogen or a sulphur atom forming a non-aromatic structure. Examples of heterocyclyl groups include, without limitation, oxalanyl, pyrrolidinyl or piperidinyl. Heterocyclic groups as used herein may optionally include further substituent groups. A substitution on the heterocyclic group also encompasses an aryl, a cycloalkyl or a heteroaryl substituent, which can be connected to the heterocyclic group via one atom or two atoms of the heterocyclic group (comparable to indole or indoline).

As used herein the term "aryl" refers to a hydrocarbon with alternating double and single bonds between the carbon atoms forming an aromatic ring structure, in particular a six ($C_6$) to ten ($C_{10}$) membered ring or polyring structure. The term "heteroaryl" refers to aromatic structures comprising a five to ten membered ring or polyring structure, comparable to aryl compounds, in which at least one member is an oxygen or a nitrogen or a sulphur atom. Due to simplicity reasons they are denominated $C_5$ to $C_{10}$ heteroaryl, wherein at least one carbon atom is replaced with an oxygen, a nitrogen or a sulphur atom forming an aromatic structure. For example a $C_5$ heteroaryl comprises a five membered ring structure with at least one carbon atom being replaced with an oxygen, a nitrogen or a sulphur atom. Examples for such a $C_5$ heteroaryl are triazolyl, pyrazolyl, imidazolyl, thiophenyl, furanyl or oxazolyl. A $C_6$ heteroaryl can be pyridyl, pyrimidinyl or triazinyl. A $C_9$ heteroaryl can be indolyl and a $C_{10}$ heteroaryl can be quinolinyl. Aryl or hetero aryl groups as used herein may optionally include further substituent groups. A substitution on the hetero aryl group also encompasses an aryl, a cycloalkyl or a heterocyclyl substituent, which can be connected to the hetero aryl via one atom or two atoms of the hetero aryl group (comparable to indole). The same applies to an aryl group.

As used herein "*" indicates a stereo center of a L- or D-enantiomer, which is located on the tertiary carbon atom below the asterisk *, and wherein the compound of a general formula comprising "*" is an essentially pure L-enantiomer, an essentially pure D-enantiomer or a mixture of the L- and D-enantiomer of the same molecular formula, wherein in particular such a compound is an essentially pure L-enantiomer or an essentially pure D-enantiomer.

According to a first aspect, the proposed solution relates to compounds having a molecular structure as defined by formula (1)

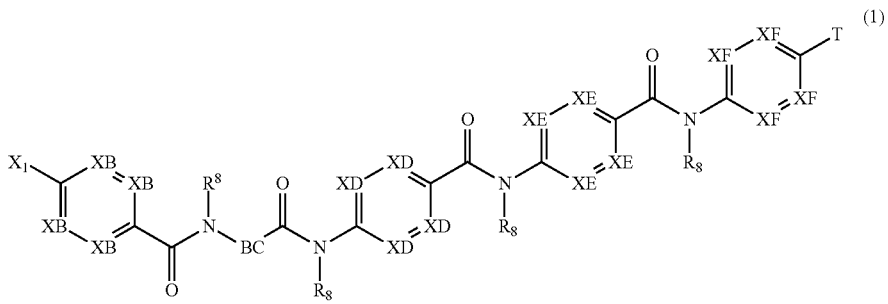

a) with XB being independently from each other N or CR$^{14}$;
b) with XD being independently from each other N or CR$^{13}$;
c) with XE being independently from each other N or CR$^{11}$;
d) with XF being independently from each other N or CR$^{10}$;
wherein at least one of XB, XD, XE and XF must be N;
with each R$^{10}$, R$^{11}$, R$^{13}$ and R$^{14}$ being selected independently from —H, —OH, —F, —Cl, —Br, —I, —CCH, —CN, —N$_3$, —OC$_1$-C$_6$ alkyl, optionally substituted with OH or F, such as, —OCF$_3$, —NH$_2$, —NHCH$_3$, —N(CH$_3$)$_2$, —C$_1$-C$_6$ alkyl, in particular —CH$_3$ or —CH$_2$CH$_3$, —(CH$_2$)m-OR$_a$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, —O—PO$_3$H$_2$, —O—PO$_3$R$_a$H or —OPO$_3$R$_{a2}$, in particular from —H, —OH, —F, —OCH$_3$, —OC$_2$H$_5$, —OiC$_3$H$_7$, —OnC$_3$H$_7$, —OCF$_3$ or —CF$_3$,
with R$^a$ being selected from
hydrogen,
a substituted or unsubstituted C$_1$-C$_{16}$ alkyl, a substituted or unsubstituted C$_2$-C$_{16}$ alkenyl, a substituted or unsubstituted C$_2$-C$_{16}$ alkynyl, or a C$_1$-C$_{16}$ haloalkyl, or
a substituted or unsubstituted C$_3$-C$_{10}$ cycloalkyl or a substituted or unsubstituted C$_3$-C$_{10}$ halo cycloalkyl;
with m being selected from 0, 1 or 2, in particular 0 or 1,
e) with BC being selected from

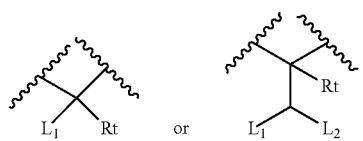

with L$_1$ being a substituted or unsubstituted aromatic heterocycle or a substituted or unsubstituted non-aromatic heterocycle, or —NHR$^d$ or —NR$^d{}_2$;
with Rt being selected from H or C$_1$-C$_4$ alkyl,
with L$_1$ and Rt forming a non-aromatic heterocycle, in particular a N-heterocyclic ring, which is optionally substituted,
with L$_2$ being selected from —H, —OH, —OR$^d$, and substituted or unsubstituted —C$_1$-C$_4$ alkyl, C$_1$-C$_6$ alkoxycarbonyl and C$_1$-C$_6$ alkylaminocarbonyl, with R$^d$ being selected from a substituted or unsubstituted C$_1$-C$_{16}$ alkyl, a substituted or unsubstituted C$_2$-C$_{16}$ alkenyl, in particular a substituted or unsubstituted C$_1$-C$_8$ alkyl, a substituted or unsubstituted C$_2$-C$_5$ alkenyl, a substituted or unsubstituted C$_3$-C$_{10}$ cycloalkyl, and all moieties optionally substituted with F,
or with BC being selected from

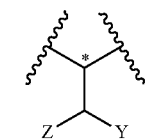

with Y being selected from —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$), —CF$_3$ or —C(=O)NH$_2$, and
with Z being selected from —H, —OH, —CH$_3$, —CH$_2$CH$_3$, —CCH, —OCH$_3$, —NH$_2$, —NHCH$_3$, —N(CH$_3$)$_2$, —N(CH$_3$)$_3{}^+$,
f) with X$^1$ being BA-CONR$^8$— with BA being selected from

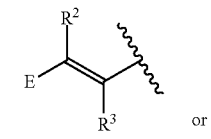
(BA1)

or

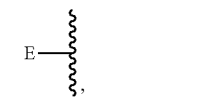
(BA2)

with R$^2$ and R$^3$ being selected, where applicable, independently from each other from —H, —F, —CN, —OH, a substituted or unsubstituted C$_1$-C$_3$ alkyl, a substituted or unsubstituted C$_1$-C$_3$ alkoxy or a C$_1$-C$_3$ haloalkyl, in particular with R$^2$ and R$^3$ being selected, where applicable, independently from each other from —H, —F, —CN, —OH, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from —H, —F, —OCH$_3$ or —CH$_3$ with E being
a substituted or unsubstituted C$_1$-C$_{16}$ alkyl, a substituted or unsubstituted C$_2$-C$_{16}$ alkenyl, a substituted or unsubstituted C$_2$-C$_{16}$ alkynyl, in particular a substituted or unsubstituted C$_1$-C$_8$ alkyl, a substituted or unsubstituted C$_2$-C$_8$ alkenyl, a substituted or unsubstituted C$_2$-C$_5$ alkynyl, a substituted or unsubstituted C$_3$-C$_{10}$ cycloalkyl, a substituted or unsubstituted C$_3$-C$_{10}$ heterocycle; in particular a substituted or unsubstituted C$_4$-C$_1$ heterocycle a substituted or unsubstituted C$_5$-C$_{10}$ heteroaryl,
a substituted or unsubstituted C$_6$-C$_{10}$ aryl,
wherein at least one optional substituent may be in particular hydroxy or halogen;

f) with each R$^8$ being —H, or C$_1$-C$_4$ alkyl, optionally substituted with one or more F, in particular with each R$^8$ being selected independently from each other from H or CH$_3$, more particularly R$^8$ being H, and g) with T being selected from
—CO$_2$H, —SO$_3$H, —C(=O)OR$^a$ or —CON(R$_a$)$_2$
with R$^a$ having the above meaning, wherein the following compounds are disclaimed:

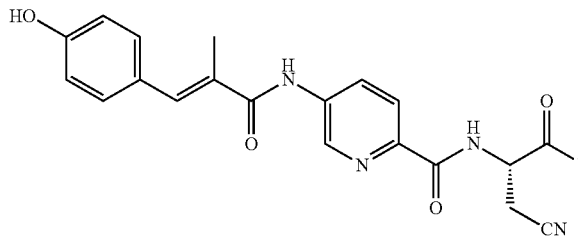
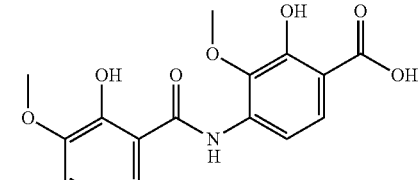

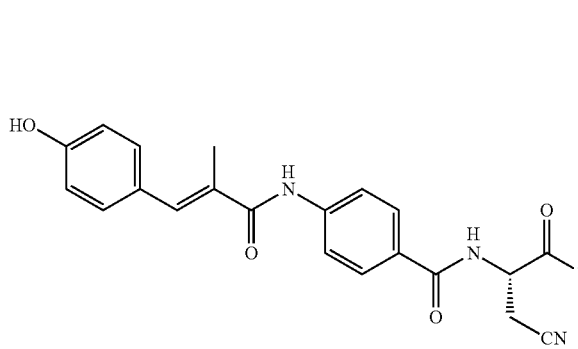
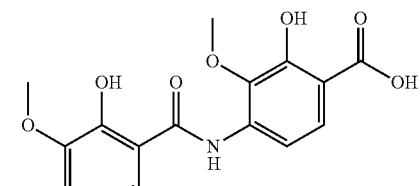

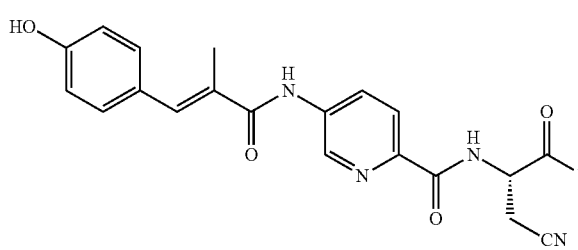
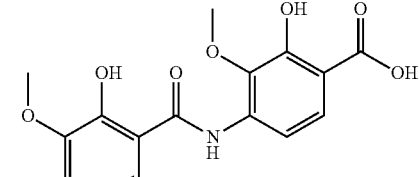

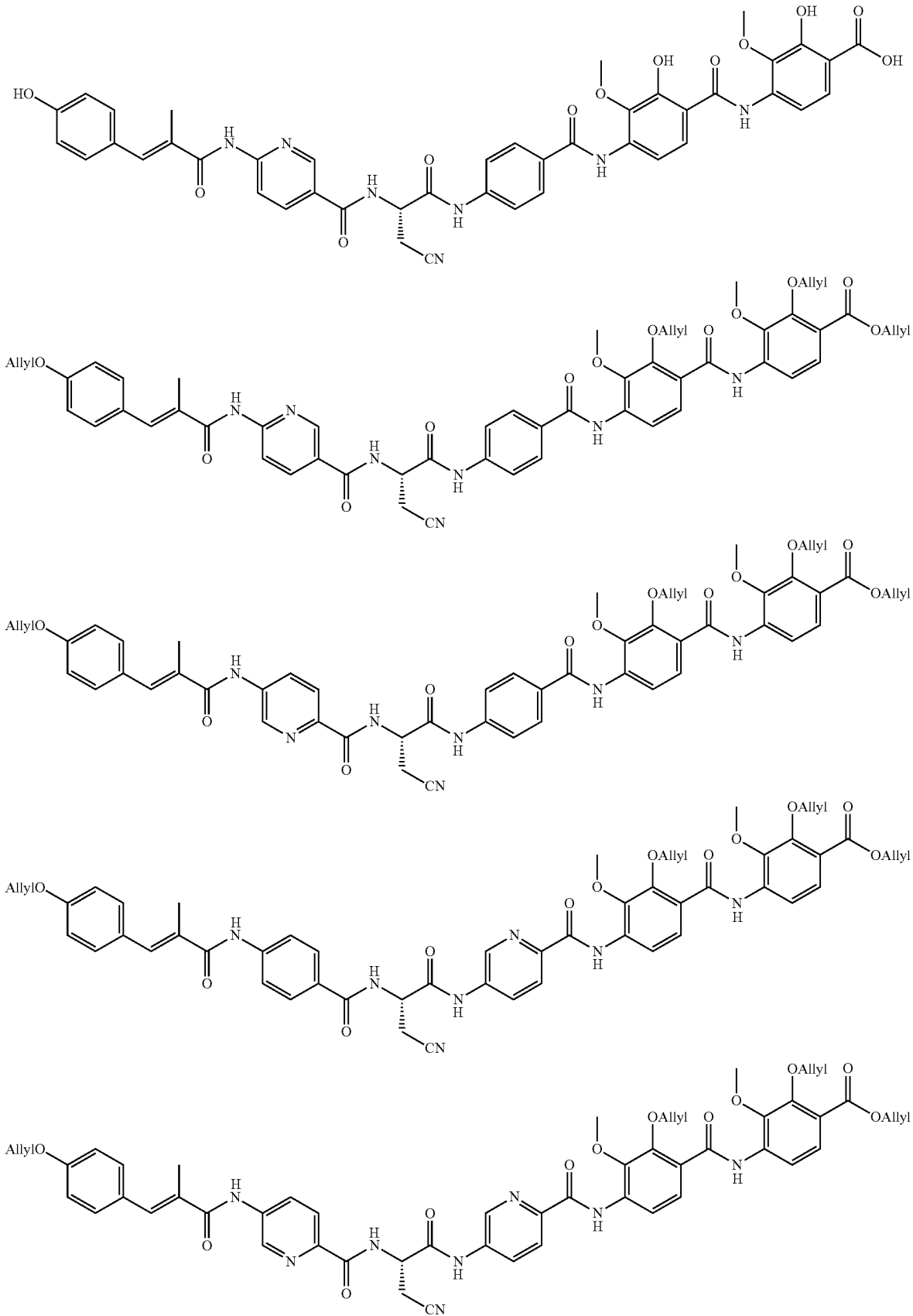

It is to be understood that with Rt and $L_1$, $L_2$ there could be two chiral centers here (providing $L_1$ and $L_2$ are not the same). Thus diastereoisomers are possible in addition to enantiomers.

In one embodiment of the present compound according to formula (1) XB, XD, XE and XF are independently from each other one, two, three or four N and one, two, three or four $CR^1$, $CR^{11}$, $CR^{13}$ and $CR^{14}$, respectively. Thus, rings B, D, E and F of the general formulae (1) corresponding to XB, XD, XE, XF may be substituted or non-substituted pyridines, pyridazines, pyrimidine, pyrazines, triazines and tetrazines.

Thus, it is possible that only one of the rings B, D, E and F comprises at least one N atom while the others are substituted or non-substituted aryl rings, as illustrated by the following structures (2a, 2b, 2c, 2d):

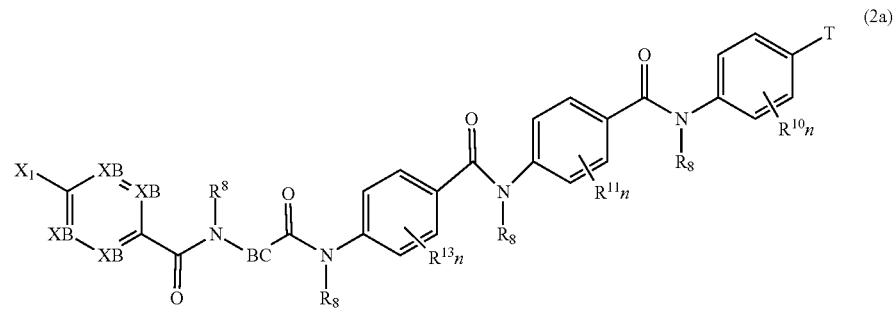
(2a)

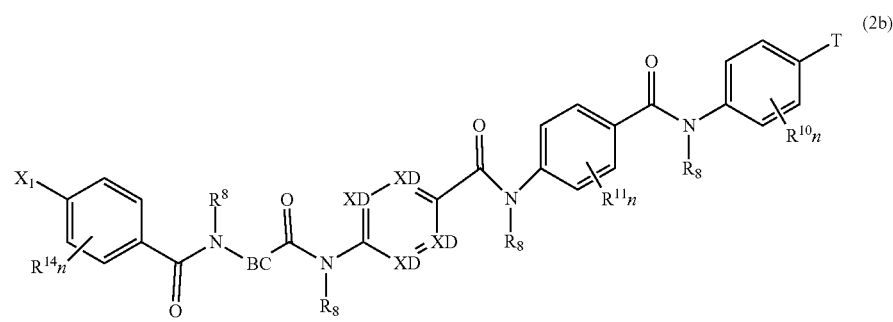
(2b)

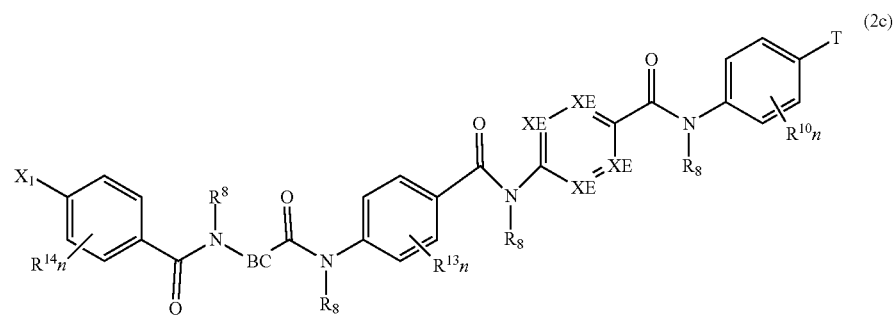
(2c)

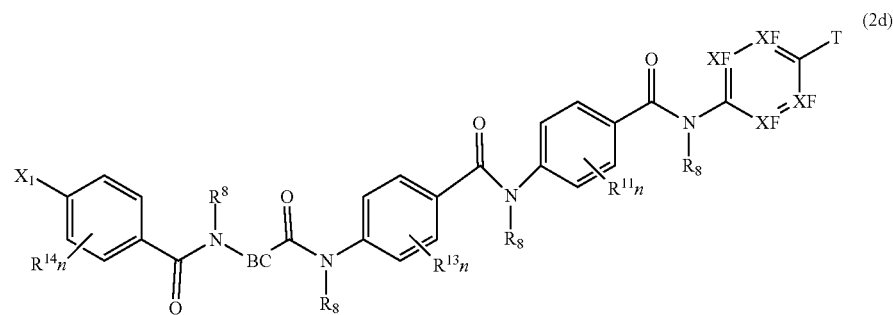
(2d)

It is furthermore possible that only two of the rings B, D, E and F comprises at least one N atom while the others are substituted or non-substituted aryl rings, as illustrated by the following structures (3a, 3b, 3c, 3d, 3e, 3f):
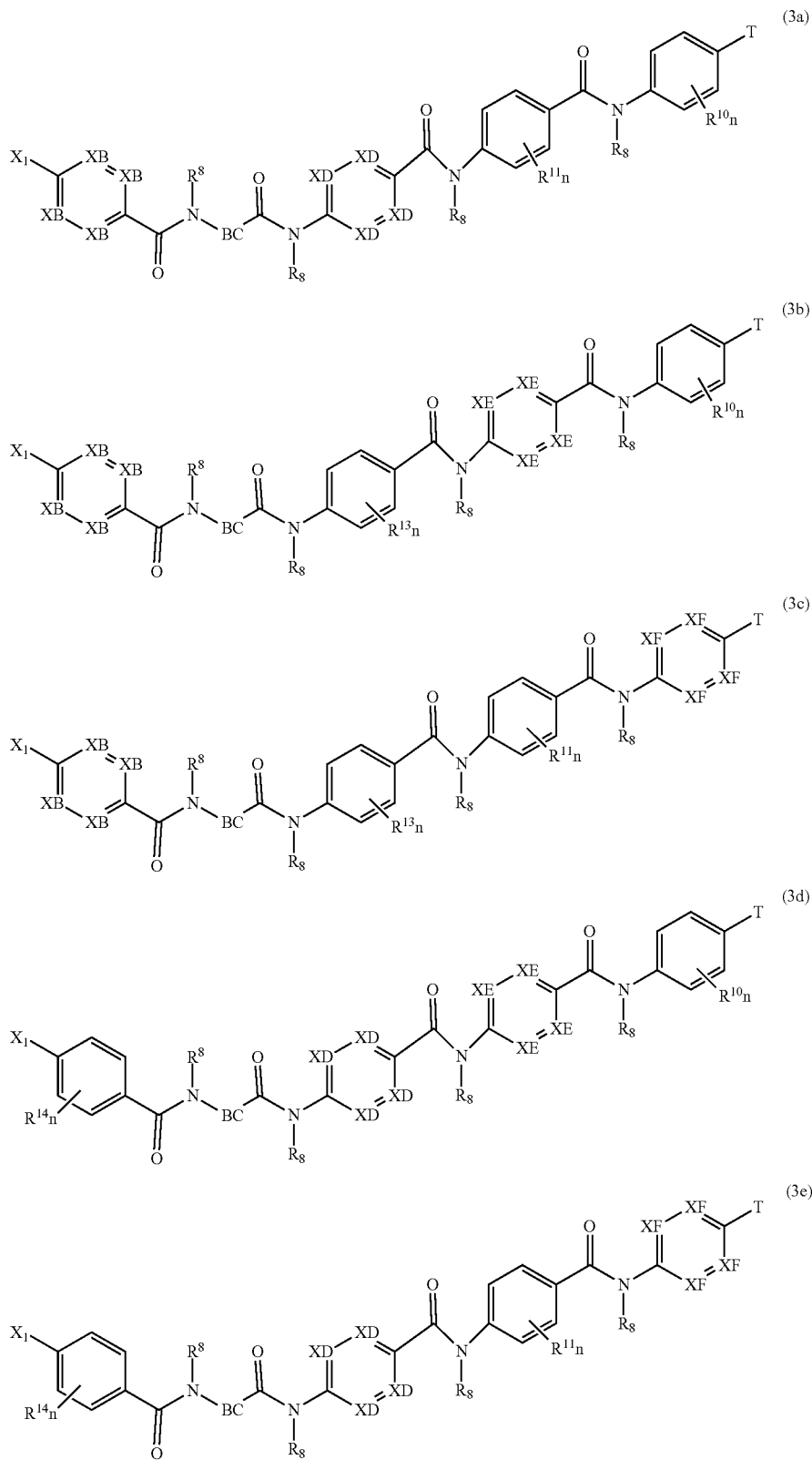

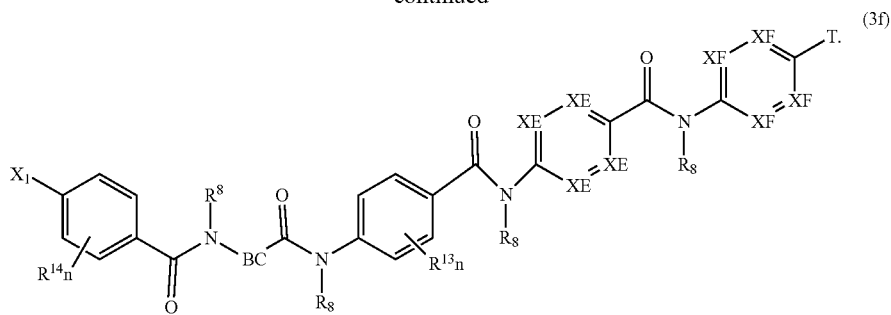
(3f)
It is furthermore possible that three of the rings B, D, E and F comprise at least one N atom while the one other is substituted or non-substituted aryl rings, as illustrated by the following structures (4a, 4b, 4c, 4d):
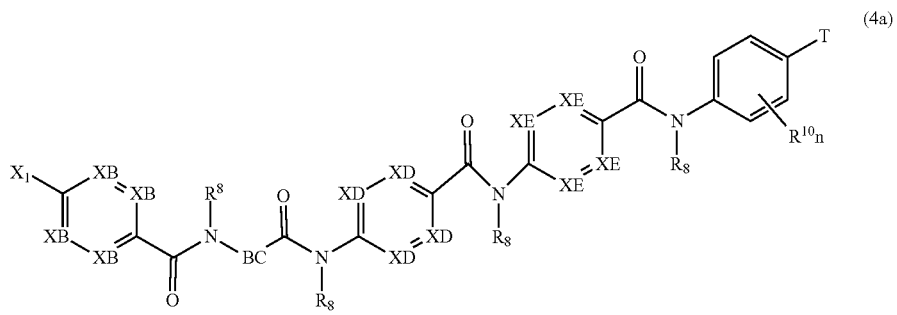
(4a)
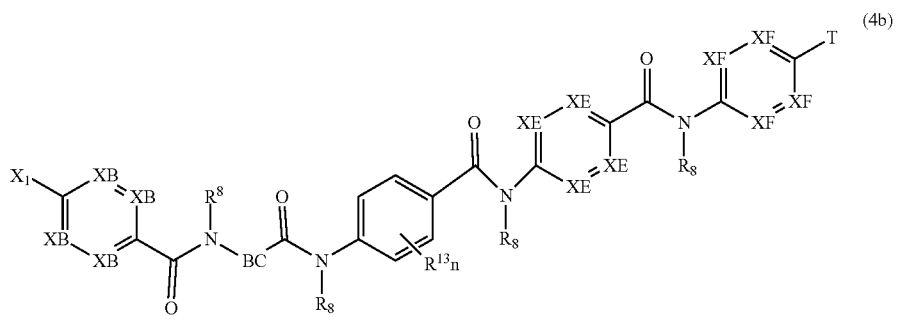
(4b)
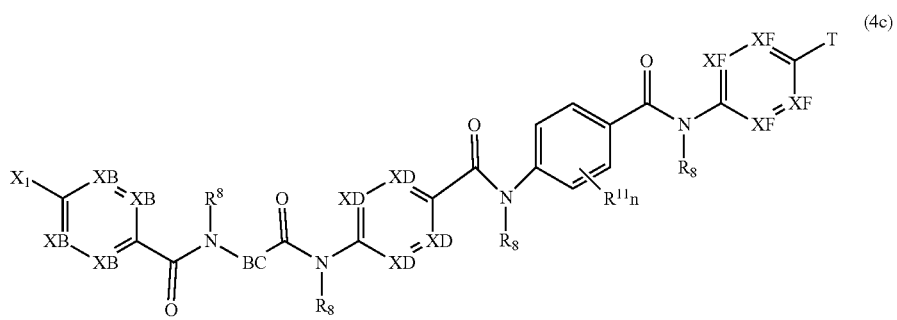
(4c)

-continued

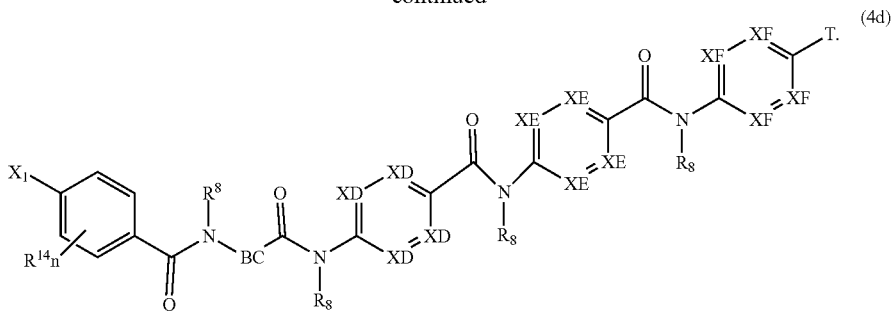

(4d)

In a more preferred embodiment XB, XD, XE and XF are independently from each other one or two N and one or two $CR^{10}$, $CR^{11}$, $CR^{11}$ and $CR^{14}$, respectively. Thus, rings B, D, E and F of the general formulae (1) corresponding to XB, XD, XE, XF may be substituted or non-substituted pyridines, pyridazines, pyrimidines, pyrazines, wherein substituted and non-substituted pyridines are of particular interest. It is to be understood that in case of substituted pyridines the corresponding tautomeric structures are also covered. For example in case of a hydroxy pyridine the corresponding pyridone is covered as well.

In one further embodiment of the present compound according to general formula (1)
one or two of XB is N and none of XD, XE, XF is N, or
one or two of XD is N and none of XB, XE, XF is N, or
one or two of XE is N and none of XB, XD, XF is N, or
one or two of XF is N and none of XB, XD, XE is N.

In yet another embodiment of the present compound according to general formula (1)
one or two of XB is N and one or two of XD is N and none of XE, XF is N, or
one or two of XB is N and one or two of XE is N and none of XD, XF is N, or
one or two of XB is N and one or two of XF is N and none of XD, XE is N, or
one or two of XD is N and one or two of XE is N and none of XB, XF is N, or
one or two of XD is N and one or two of XF is N and none of XB, XE is N, or
one or two of XE is N and one or two of XF is N and none of XB, XD is N.

In yet a further embodiment of the present compound according to general formula (1)
one or two of XB is N, one or two of XD is N and one or two of XE is N and none of XF is N, or
one or two of XB is N, one or two of XD is N and one or two of XF is N and none of XE is N, or
one or two of XB is N, one or two of XE is N and one or two of XF is N and none of XD is N, or
one or two of XD is N, one or two of XE is N and one or two of XF is N and none of XB is N.

In one embodiment of the present compound each $R^{10}$, $R^{11}$, $R^{13}$ and $R^{14}$ is independently selected from being from —H, —OH, —F, —OCH$_3$, —OC$_2$H, —OC$_3$H$_7$, —OCF$_3$, —CF$_3$ or —(CH$_2$)m-OR$^a$,
with $R^a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$—CH$_2$C$_6$H$_5$, with m being selected from 1 or 2;
more particularly with one of $R^{10}$, $R^{11}$ and $R^{13}$ being —OH, OCH$_3$, —OC$_2$H$_5$ or —OiPr and $R^{14}$ being H, respectively.

In case that each of XB, XD, XE and XF is $CR^{14}$, $CR^{13}$, $CR^{11}$ and $CR^{10}$, respectively, then the number of $R^{14}$, $R^{13}$, $R^{11}$ and $R^{10}$ on the respective ring is determined according to $R^{14}{}_n$, $R^{13}{}_n$, $R^{11}{}_n$ and $R^{10}{}_n$. In an embodiment of the present compound n of $R^{14}$ n, $R^{13}$, $R^{10}$ and $R^{11}$ is 0, 1, 2, 3 or 4, in particular n is 0, 1, 2 or 3.

In one embodiment each $R^{10}$ and with each $R^{11}$ may be independently selected from any other $R^{10}$ from —OH, —F, —OCH$_3$, —OC$_2$H$_5$, —OnC$_3$H$_7$, —OisoC$_3$H$_7$, —OCF$_3$, —CF$_3$ or —(CH$_2$)m-OR$^a$,
with $R^a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$—CH$_2$C$_6$H$_5$,
with m being selected from 1 or 2,
more particularly with one $R^{10}$ or $R^{11}$ being —OH and the other $R^{10}$ or $R^{11}$ being —OCH$_3$, —OC$_2$H$_5$ or —OiPr respectively.

In one further preferred embodiment of $R^{13Q}$ n is 1 or 2, in particular 1, and $R^{13}$ is —OH, wherein in case of n is 1 $R^{13}$ is preferably in 2-position (i.e. ortho position to —CO—) or in 3-position (i.e. ortho-position to —NR$^8$—). In case n=2 one $R^{13}$ is OH (ortho position to —CO—) and the other is —OCH$_3$ (ortho-position to —NR$^8$—).

In one embodiment of the present compound according to formula (1) the moiety $L_1$ is a five membered or six membered aromatic heterocycle or 3-7 membered non-aromatic heterocycle, preferably a five membered or six membered aromatic N-heterocycle or non-aromatic N heterocycle that may be substituted or unsubstituted.

In specific embodiments the moiety $L_1$ is a five membered aromatic N-heterocycle selected from a group comprising substituted or unsubstituted
pyrroles, imidazoles, pyrazoles, triazoles, tetrazoles; wherein triazoles are the most preferred;
pyrazolone, preferably 3H-pyrazol-3-ones, 4H-pyrazol-4-ones, 1,2-dihydro-3H-pyrazol-3-ones, 2,4-dihydro-3H-pyrazol-3-ones, triazolones, preferably 1,2,4-triazol-3-one, imidazolones, pyrrolidones,
thiadiazoles, preferably 1,3,4-thiadiazoles, thiazoles, isothiazoles, thiazolidinediones; and
isoxazoles, oxazoles, oxadiazoles (1,3,4-oxadiazoles, 1,2,4-oxadiazoles), The aromatic five membered heterocycles may be preferably substituted by a $C_1$-$C_6$ alkyl moiety, most preferably by a methyl or ethyl moiety. It is most preferred, if the N atom is substituted by a $C_1$-$C_6$ alkyl moiety, most preferably by a methyl or ethyl moiety.

In further embodiments of the present compound of formula (1) the moiety $L_1$ is a five membered non-aromatic N-heterocycle selected from a group comprising substituted or unsubstituted
pyrrolidines, pyrazolidines,
hydantoines, imidazolidinones (imidazolidin-4-one), isoxazolidines, oxazolidinones (1,3-oxazolidin-2-one); isothiazolidines, isothiazolinone.

In yet further embodiments the moiety $L_1$ is a six membered aromatic N-heterocycle selected from a group comprising substituted or unsubstituted pyridines, pyridazines, pyrimidines, pyrazines, triazines and tetrazines.

In still another embodiment of the present compound of formula (1) the moiety $L_1$ is a six membered non-aromatic N heterocycle selected from a group comprising substituted or unsubstituted piperidines and piperazines or morpholines.

The non-aromatic 5 and 6 membered heterocycles may be preferably substituted by a $C_1$-$C_6$ alkyl moiety, most preferably by a methyl or ethyl moiety. It is most preferred, if the N atom is substituted by a $C_1$-$C_6$ alkyl moiety, most preferably by a methyl or ethyl moiety. For example, a suitable substituted N-heterocycle may be N-methyl piperidine.

In still another embodiment of the present compound of formula (1) the moiety $L_1$ is —NHR$^d$ or —NR$^d_2$ wherein Rd is a methyl or ethyl moiety.

The moiety $L_2$ may be selected from —H, —OH, —OR$^d$, and —CH$_3$, —C$_2$H$_6$ or —C$_3$H$_7$, with R$^d$ being substituted or unsubstituted $C_1$-$C_5$ alkyl, preferably a $C_1$-$C_3$ alkyl.

In a variant Z is being H and Y being CN or —C(=O)NH$_2$, more preferably Z being H and Y being CN.

In a preferred embodiment the present compound may be of the general formulae (5)

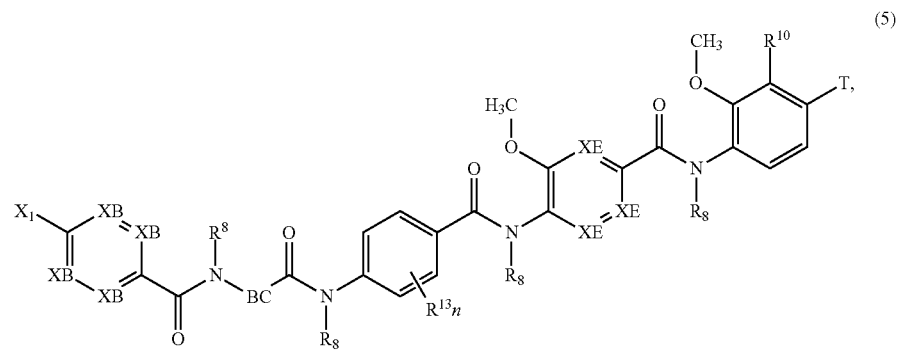

(5)

wherein $X^1$, XB, XE, BC, $R^8$, $R^{13}$, $R^{10}$ and T have the above meaning.

In another preferred embodiment the present compound may be of the general formulae (5a)

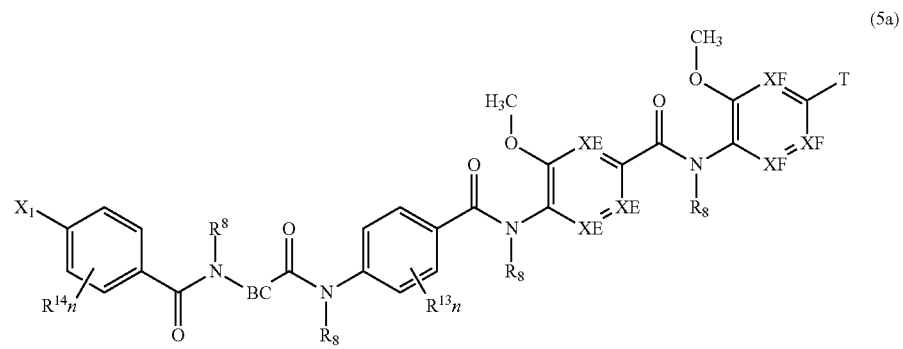

(5a)

wherein $X^1$, XB, XE, BC, $R^8$, $R^{13}$, $R^{14}$ and T have the above meaning.

In another preferred embodiment the present compound may be of the general formulae (5b)

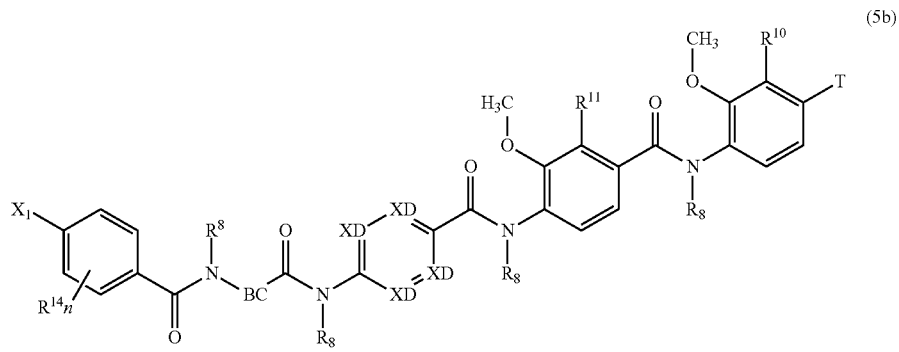

(5b)

wherein $X^1$, XD, BC, $R^8$, $R^{11}$, R10, $R^{14}$ and T have the above meaning.

In another preferred embodiment the present compound may be of the general formulae (5c)

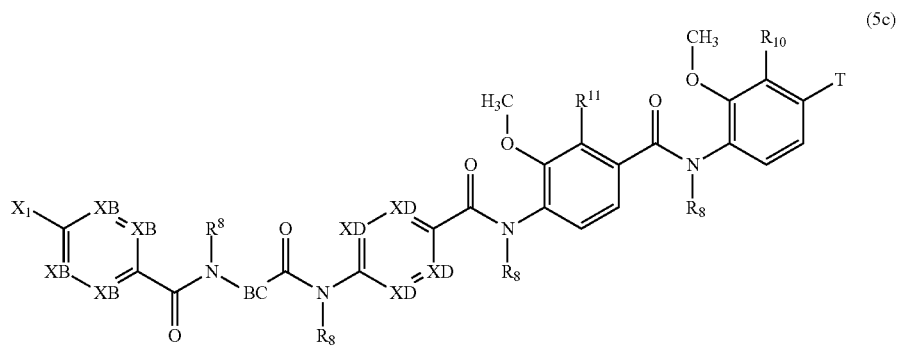

(5c)

wherein $X^1$, XB, XD, BC, $R^8$, R10, $R^{11}$ and T have the above meaning.

In another preferred embodiment the present compound may be of the general formulae (5d)

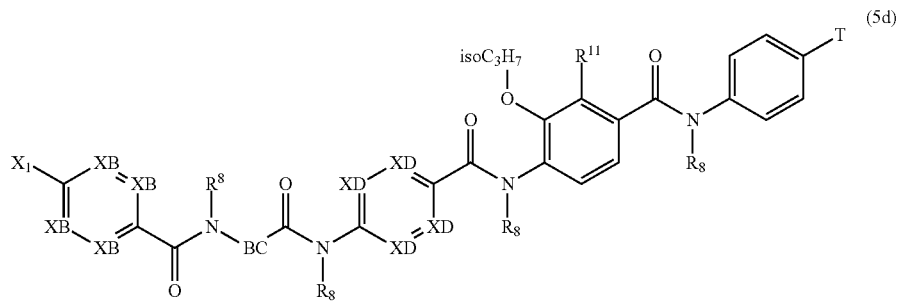

(5d)

wherein $X^1$, XB, XD, BC, $R^8$, $R^{11}$ and T have the above meaning.

In another preferred embodiment the present compound may be of the general formulae (5e)

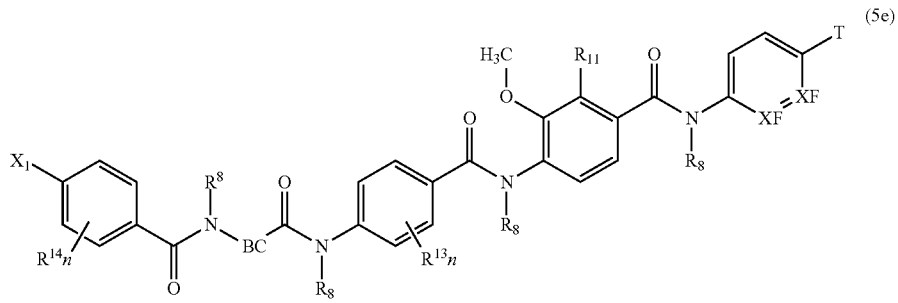

(5e)

wherein $X^1$, XF, BC, $R^8$, $R^{11}$, $R^{13}$, $R^{14}$ and T have the above meaning.

In another preferred embodiment the present compound may be of the general formulae (6)

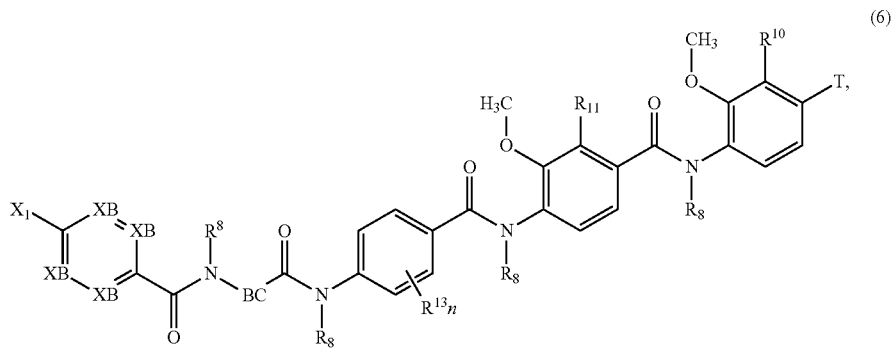

(6)

wherein $X^1$, XB, BC, $R^8$, $R^{11}$, $R^{10}$, $R^{13}$ and T have the above meaning.

In yet another preferred embodiment the present compound may be of the general formulae (7)

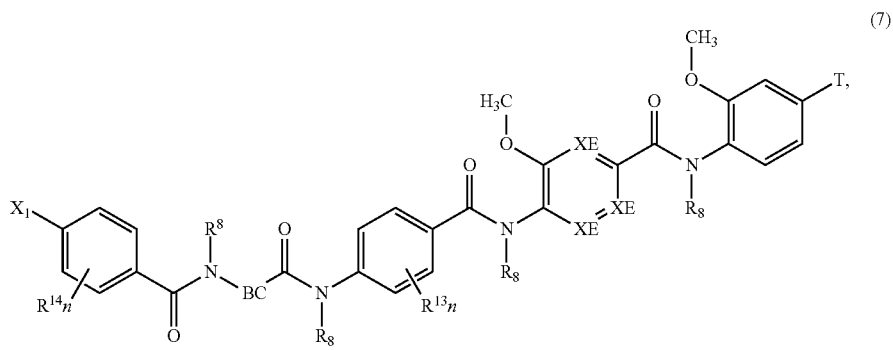

(7)

wherein $X^1$, XE, BC, $R^8$, $R^{14}$, $R^{10}$, $R^{13}$ and T have the above meaning.

In yet another preferred embodiment the present compound may be of the general formulae (8)

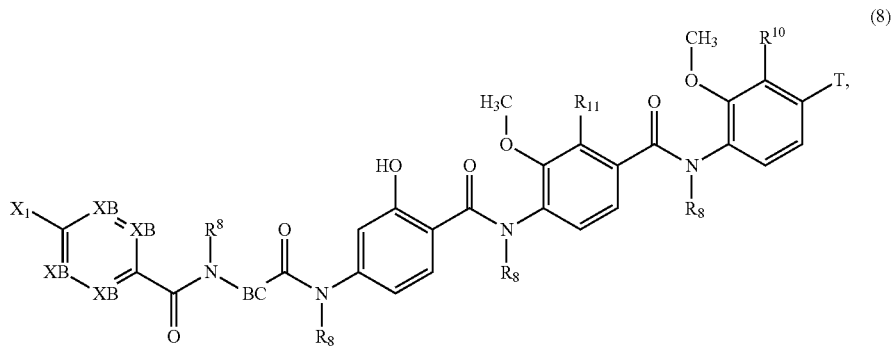

(8)

wherein $X^1$, XB, BC, $R^8$, $R^{11}$, $R^{10}$ and T have the above meaning.

In still another preferred embodiment the present compound may be of the general formulae (9)

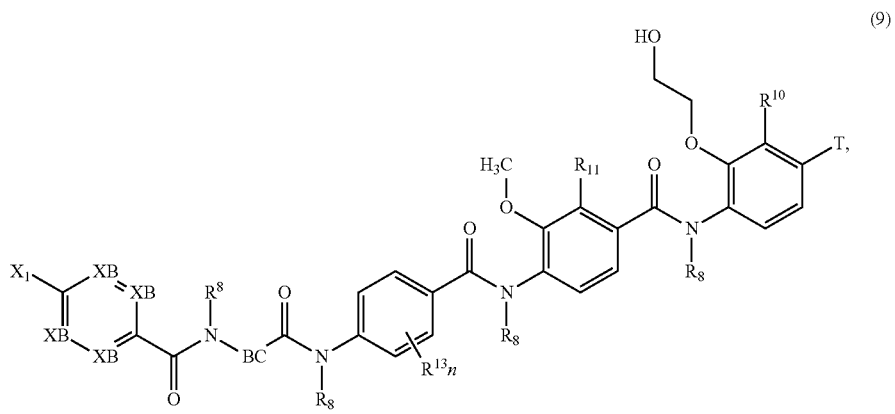

(9)

wherein $X^1$, XB, BC, $R^8$, $R^{11}$, $R^{10}$, $R^3$ and T have the above meaning.

In another embodiment of the present compounds of general formula (1) and (2) the moiety $X^1$ is BA-CONHR$^8$—, with BA being BA1, with $R^2$ and $R^3$ having the same meaning as defined previously, and with E being

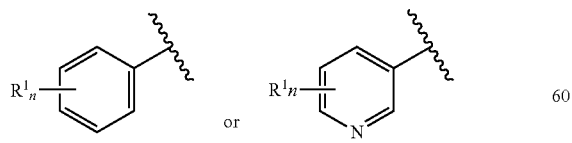

or with n of $R^1$. being 0, 1, 2, 3, 4 or 5, in particular n of $R^1$ being 0, 1, 2 or 3, more particularly n of $R^1$ being 1, and with each $R^1$ independently from any other $R^1$ being selected from —OH, —F, —Cl, —Br, I, —CCH, —CN, —N$_3$, —OCH$_3$, —OC$_2$H, —OC$_3$H$_7$, in particular —OiPr, —OCF$_3$, —OCHCCH, —NH$_2$, —NHCH$_3$, —N(CH$_3$)$_2$, —CH$_3$, —CH$_2$—CH$_3$, —CF$_3$, —OCONH$_2$, —NO$_2$, —OCH$_2$O—, —O—PO$_3$H$_2$, —O—PO$_3$RaH—O—PO$_3$R$_{a2}$ or —(CH$_2$)m-OR$_a$, with m and R$_a$ having the above meaning. $R^1$ is preferably —OH, —OCHCCH, —OCH$_3$, —OC$_2$H, —F, —CN, most preferably —F, —OH, —CN and —OCHCCH.

In another embodiment of the present compounds of general formula (1) and (2) the moiety $X^1$ is BA-CONHR$^8$—, with BA being BA2, with E being

- a substituted or unsubstituted C$_1$-C$_5$ alkyl, a substituted or unsubstituted C$_2$—C alkenyl, a substituted or unsubstituted C$_2$-C$_8$ alkynyl, a substituted or unsubstituted C$_3$-C$_{10}$ cycloalkyl,
- a substituted or unsubstituted C$_4$-C$_{10}$ heterocycle
- a substituted or unsubstituted C$_5$-C$_{10}$ heteroaryl, in particular pyridine, wherein at least one optional substituent may be in particular aryl, phenyl, methoxyphenyl, hydroxy or halogen; such as fluor;

E may be in particular a C2 Alkynyl substituted with aryl or heteroaryl;

or with E being a $C_6$ aryl according to

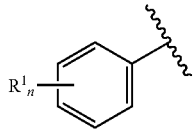

with n of $R^1$. being 0, 1, 2, 3, 4 or 5, in particular n of $R^1$ being 0, 1, 2 or 3, more particularly n of $R^1$ being 1, and with each $R^1$ independently from any other $R^1$ being selected from —OH, —F, —Cl, —Br, I, —CCH, —CN, —$N_3$, —$OCH_3$, —$OC_2H$, —$OC_3H_7$, in particular —OiPr, —$OCF_3$, —OCHCCH, —$NH_2$, —$NHCH_3$, —$N(CH_3)_2$, —$CH_3$, —$CH_2$—$CH_3$, —$CF_3$, —$OCONH_2$, —$NO_2$, —$OCH_2O$—, —O—$PO_3H_2$, —O—$PO_3R_aH$—O—$PO_3R_{a2}$ or —$(CH_2)_m$—$OR_a$; with m and $R_a$ having the above meaning. $R^1$ is preferably —OH, —OCHCCH, —$OCH_3$, —$OC_2H$, —F most preferably —OH.

In some embodiments, $X^1$ is selected from

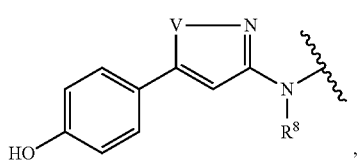

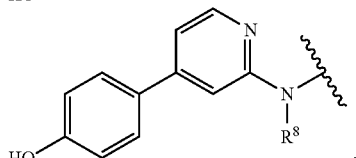

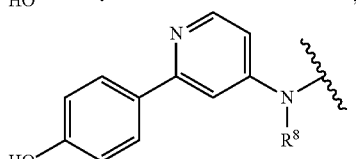

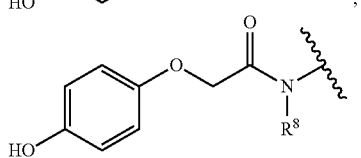

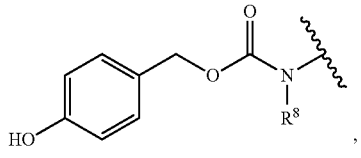

or with $R^8$ being selected from H or $CH_3$, in particular $R^8$ is H and with V being selected from O, NH or S, in particular from O or NH.

In some embodiments, $X^1$ is selected from

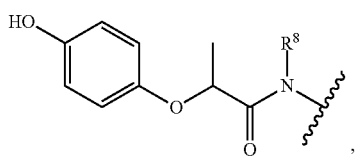

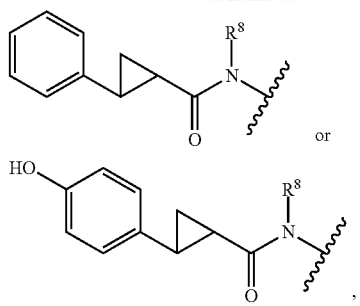

or with $R^8$ being selected from H or $CH_3$, in particular $R^8$ is H. It is to be understood that all possible optical isomers may be covered.

In some embodiments, $X^1$ is selected from

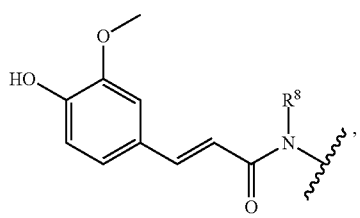

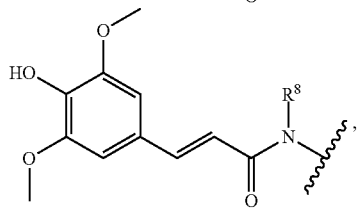

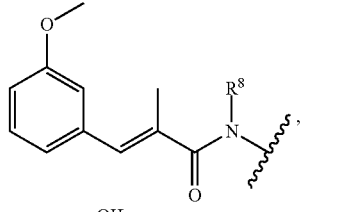

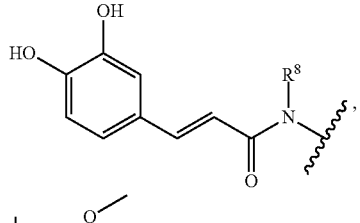

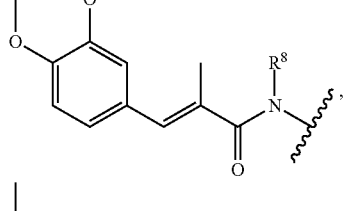

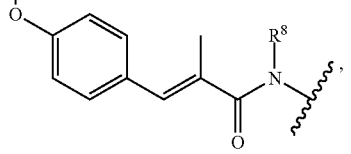

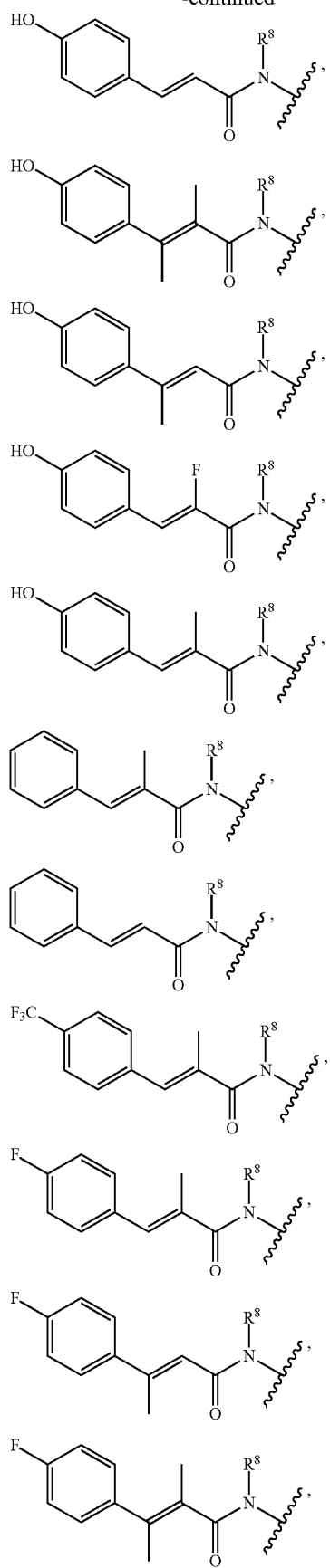
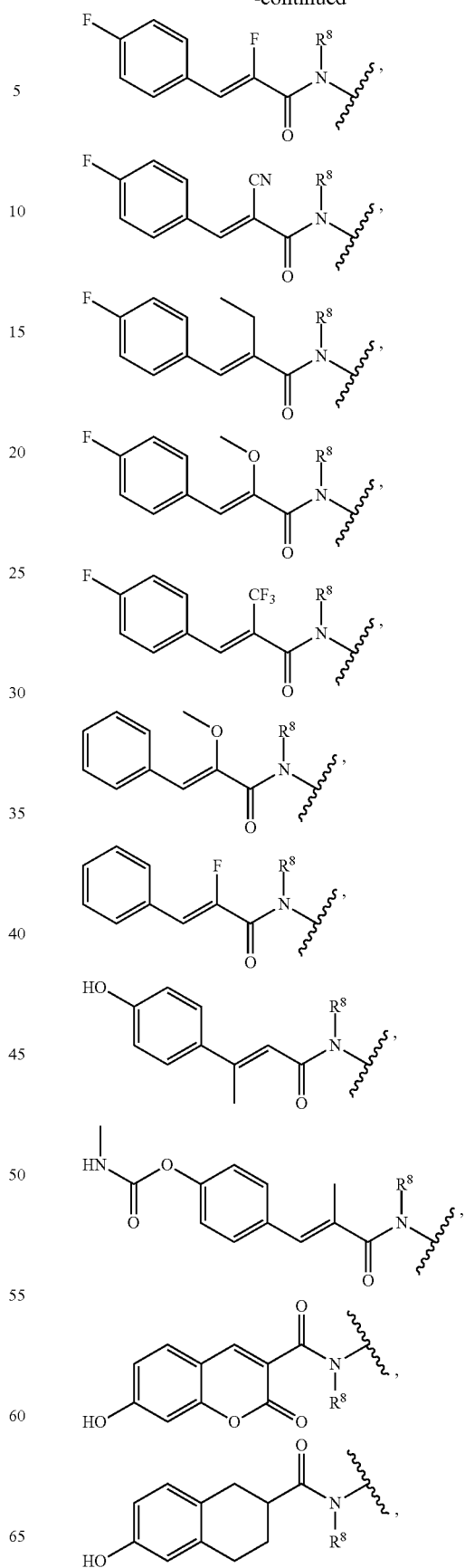

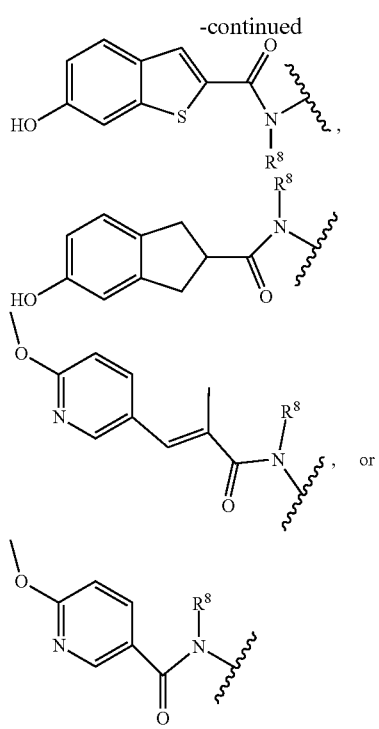

with R⁸ being selected from H or CH₃, in particular R⁸ is H.

In a more preferred embodiment X¹ is

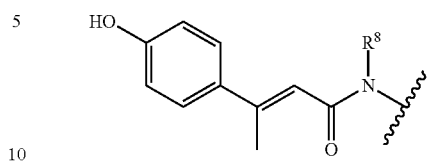

with R⁸ being H.

In yet another preferred embodiment of the present compound the moiety T is —CO₂H, —SO₃H, —C(=O)ORᵃ or —CON(Rᵃ)₂, with Rᵃ being selected from hydrogen, —CH₃, —CH₂CH₃, —CH₂CH₂CH₃, —CH₂CH₂CH₂CH₃, —CH(CH₃)₂, —CH₂CH(CH₃)₂, —C(CH₃)₃, —C₆H₅—CH₂C₆H₅;

with T being in particular —CO₂H.

It further embodiments in case of the compounds of formulas (1), (2a-d), (3a-f), (4a-d), (5,5a-e), (6), (7), (8) and (9) in each case moiety T is —CO₂H; moiety BC is CH—CH₂-Triazole, and moiety X₁ is —NHCO—C(CH₃)=-Ph(OH, F, CN).

Particular embodiments of the solution are one the following compounds:

Compound 1

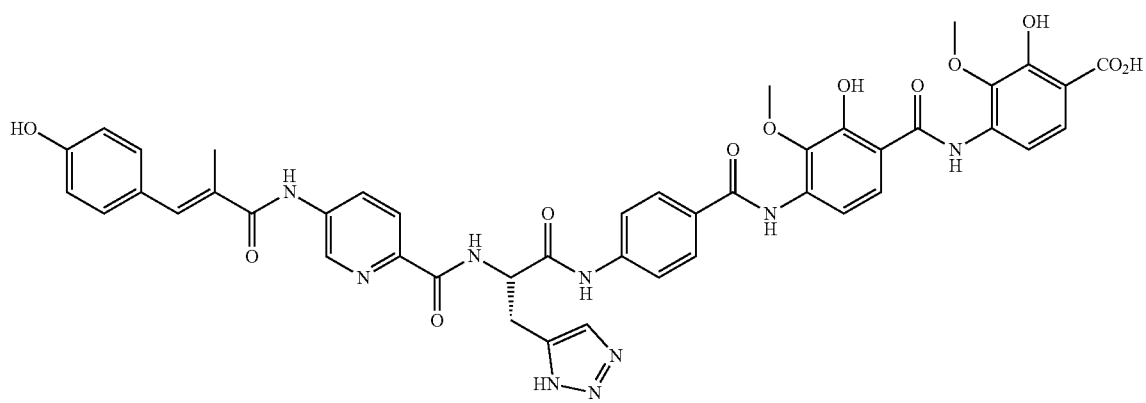

Compound 2

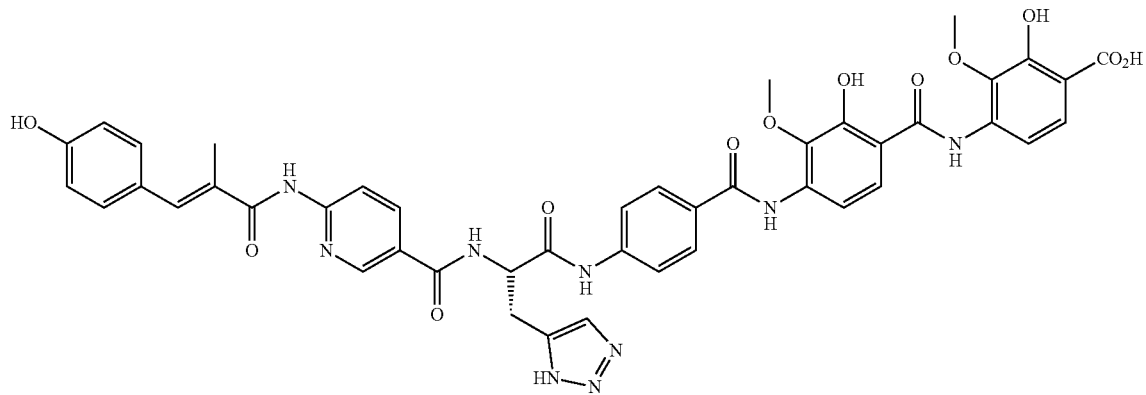

-continued
Compound 3
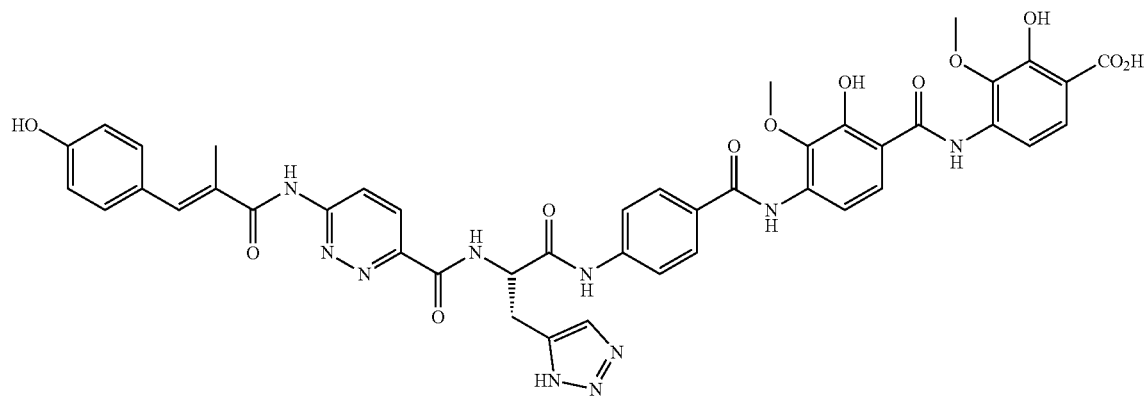
Compound 4
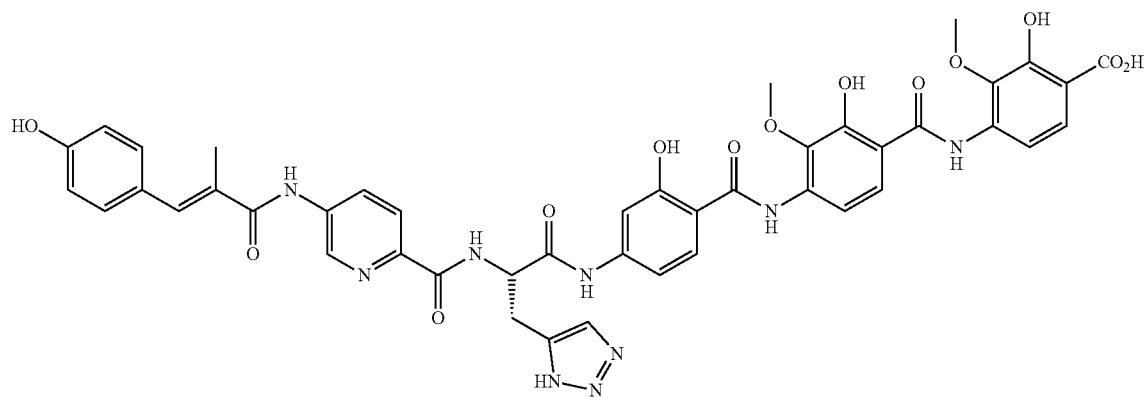
Compound 5
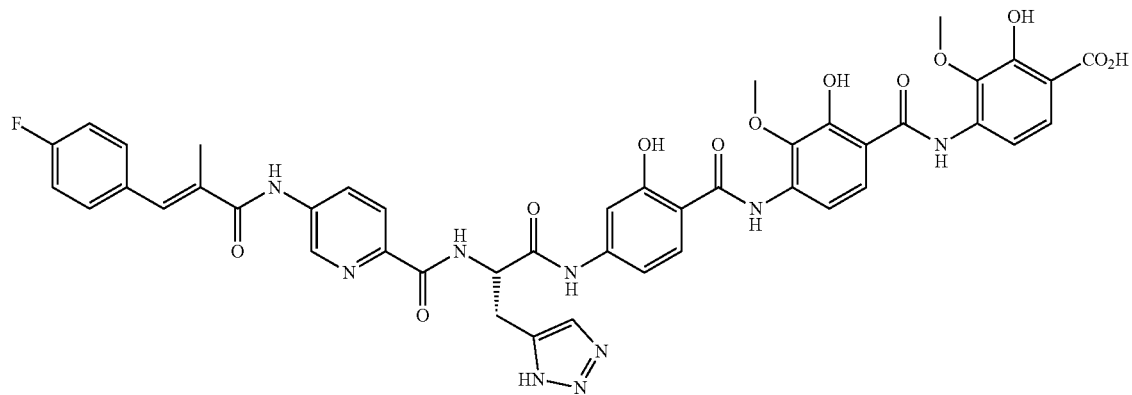

-continued
Compound 6
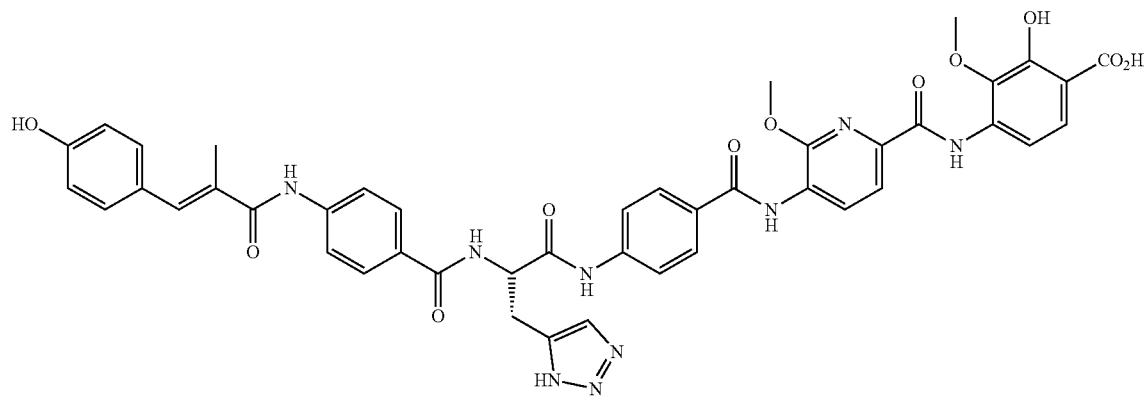
Compound 7
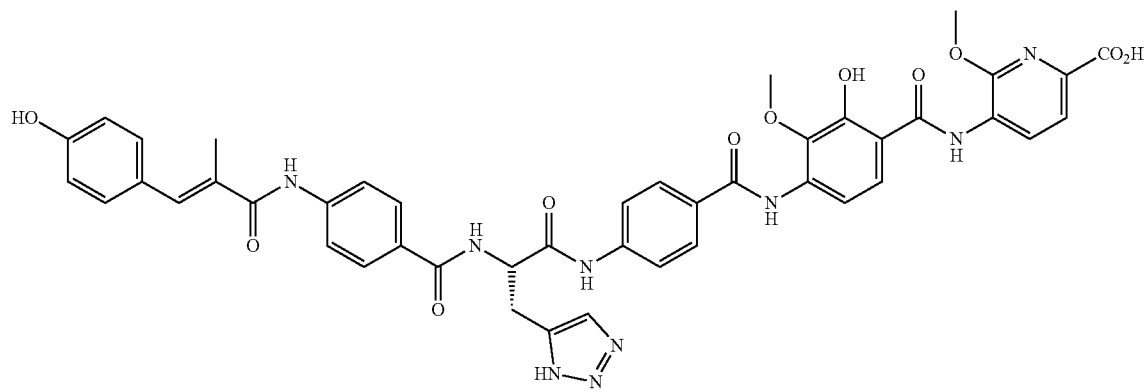
Compound 8
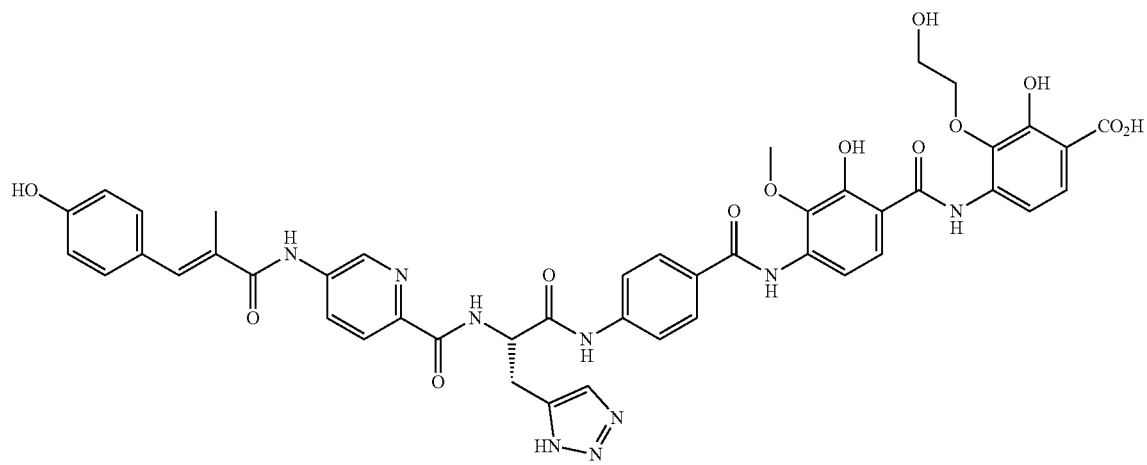

Compound 9
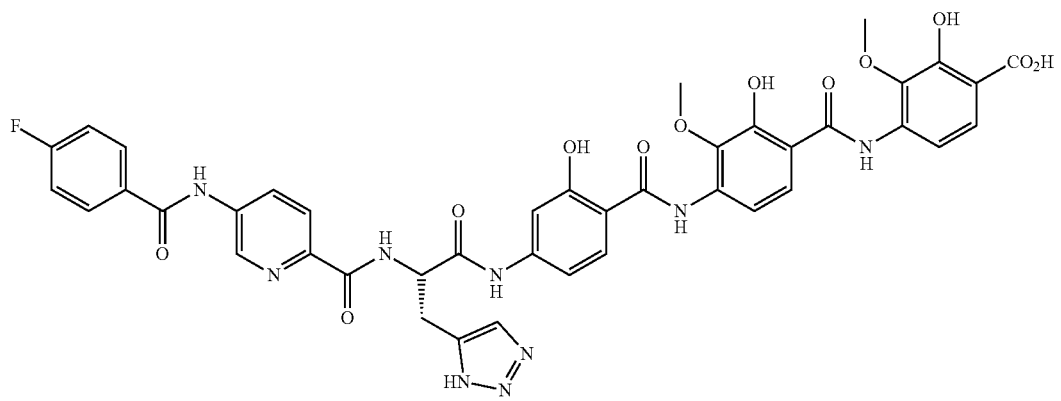
Compound 10
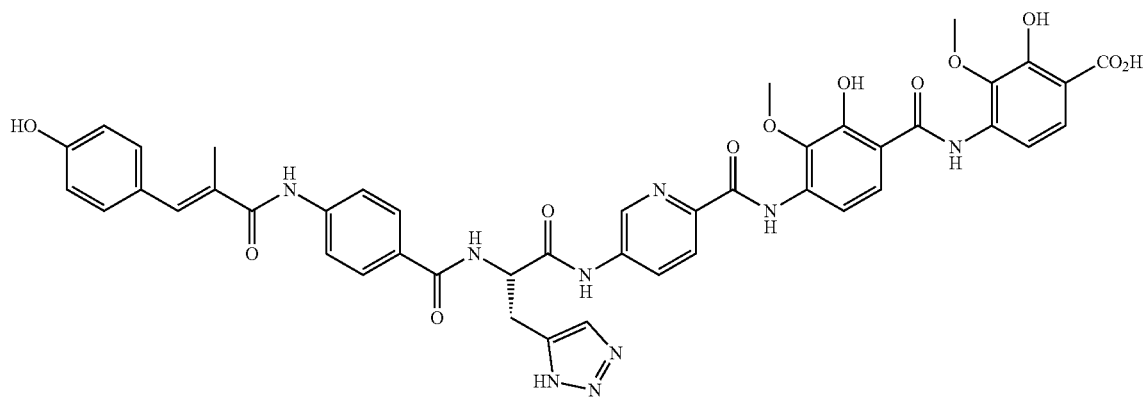
Compound 11
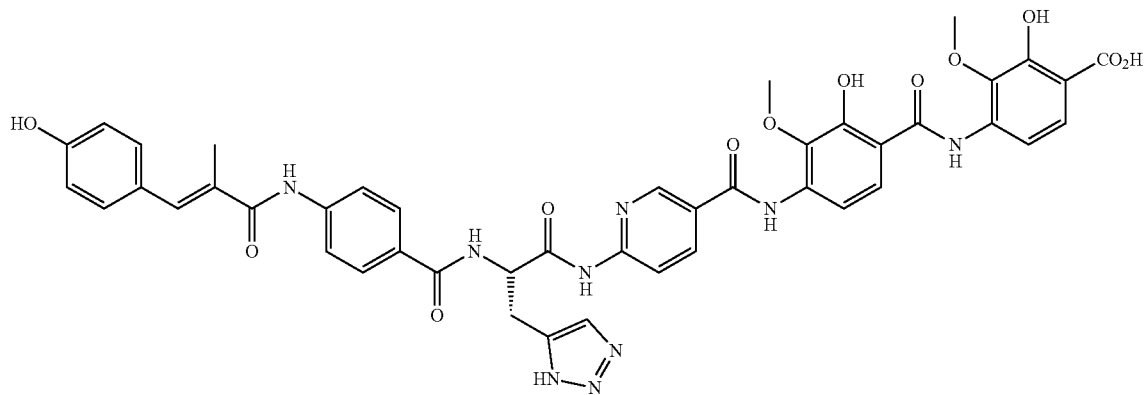

Compound 12
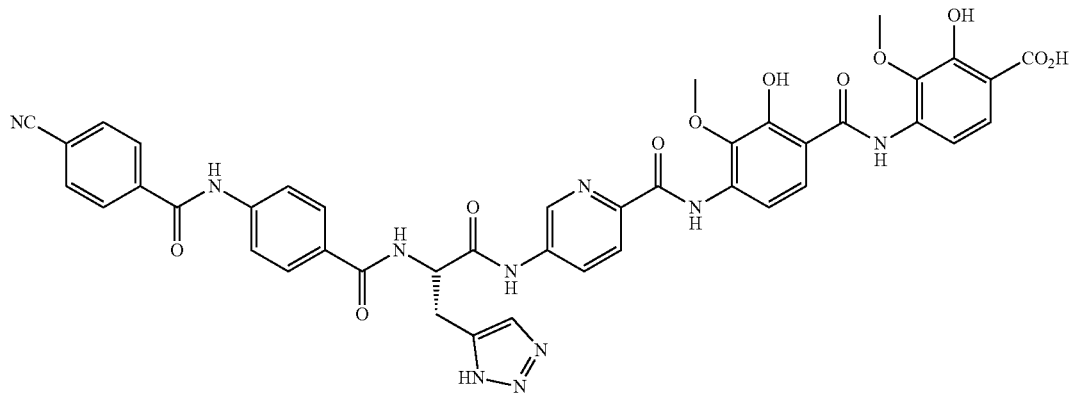
Compound 13
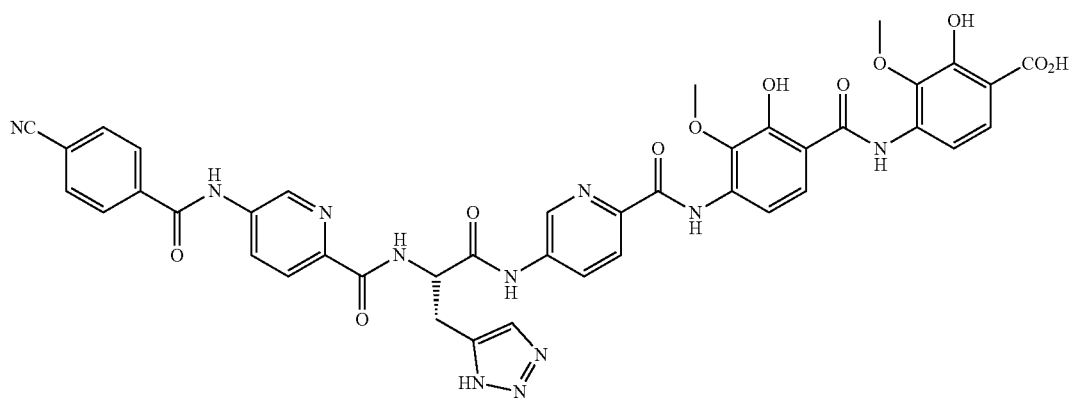
Compound 14
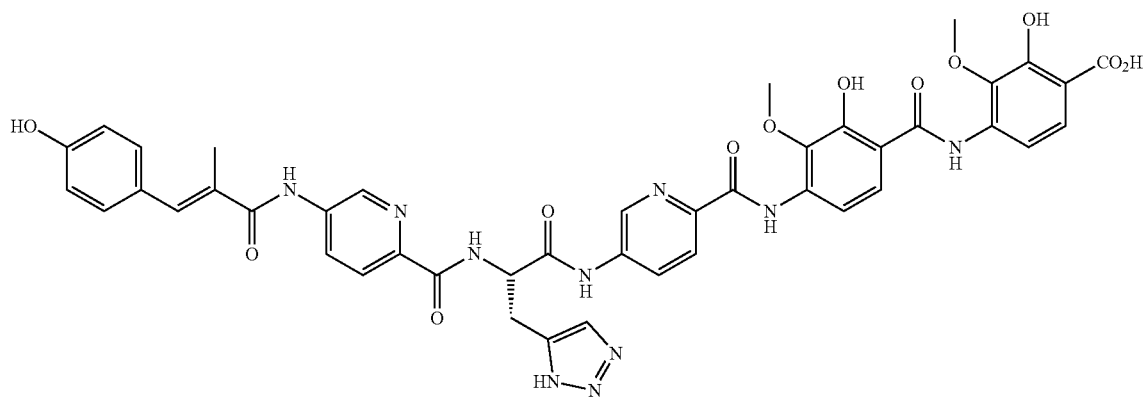
Compound 15
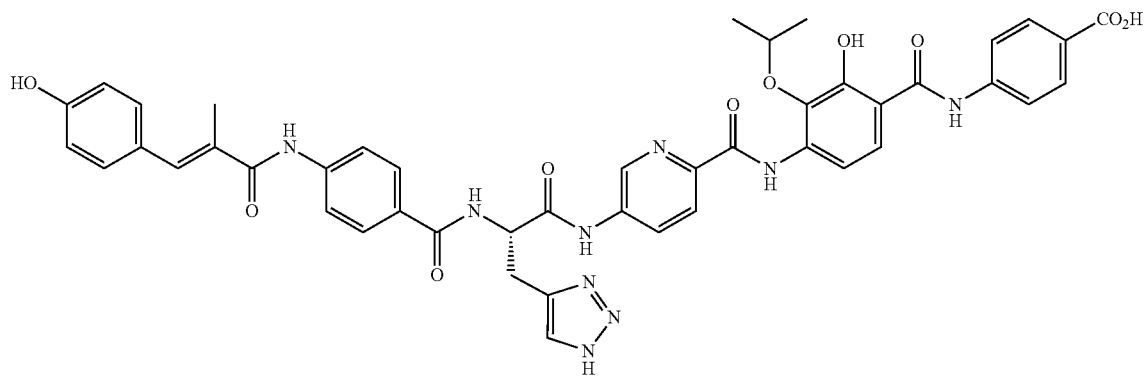

-continued
Compound 16
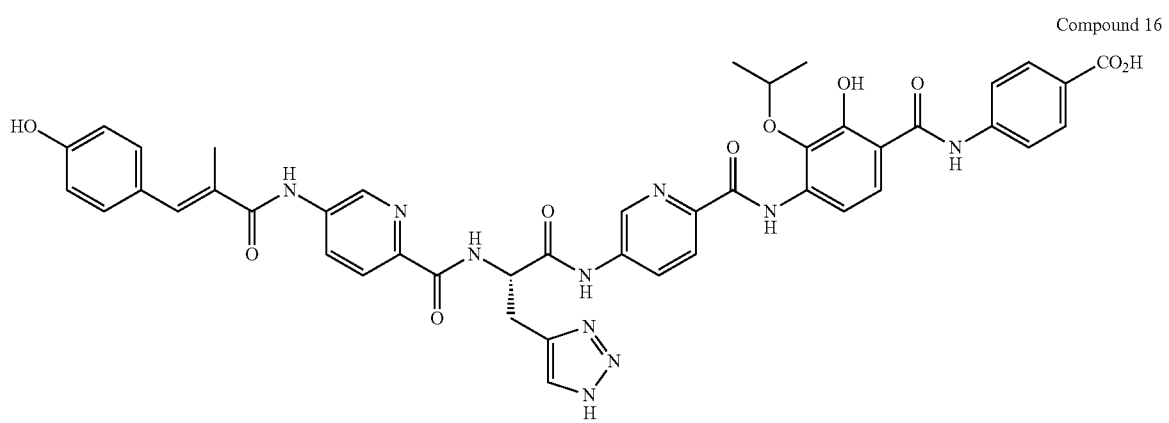
Compound 17
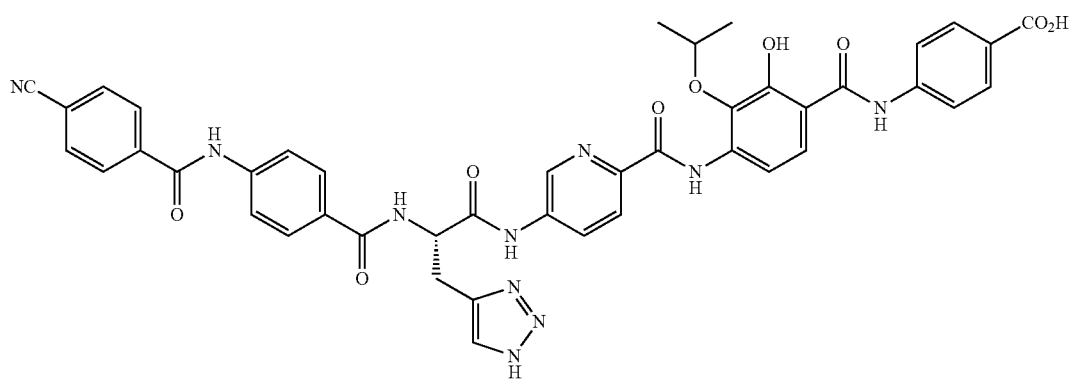
Compound 18
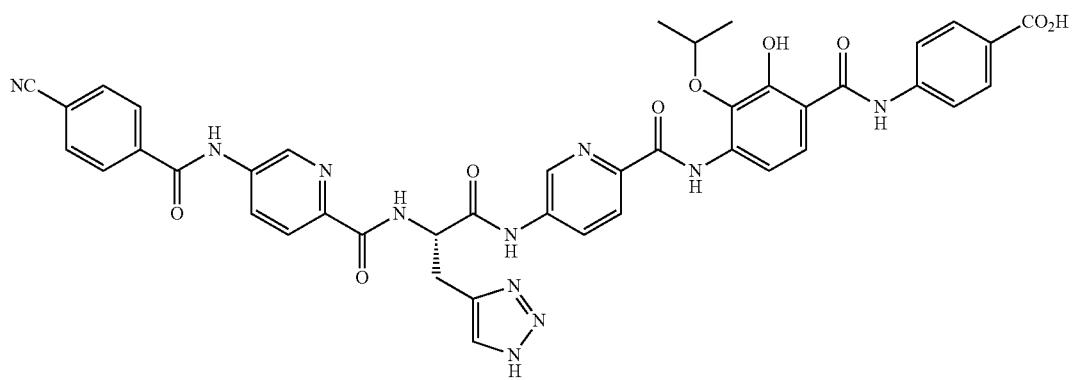
Compound 19
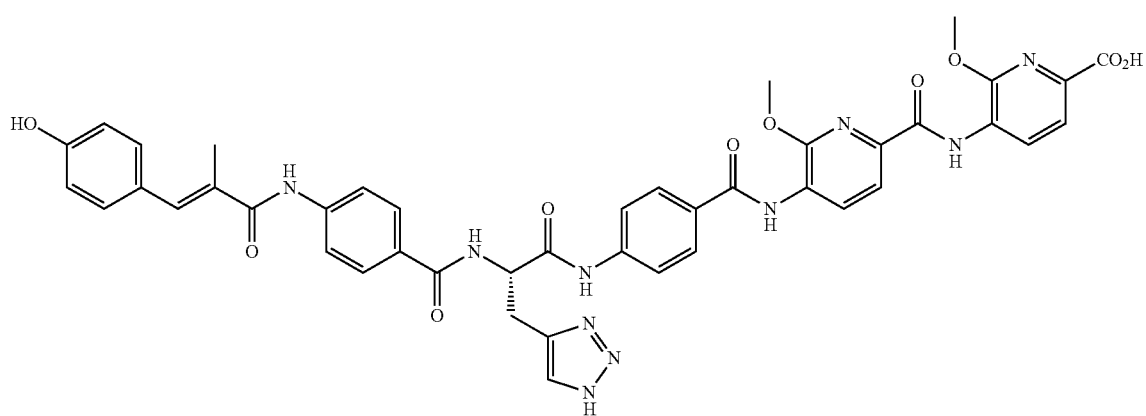

-continued
Compound 20
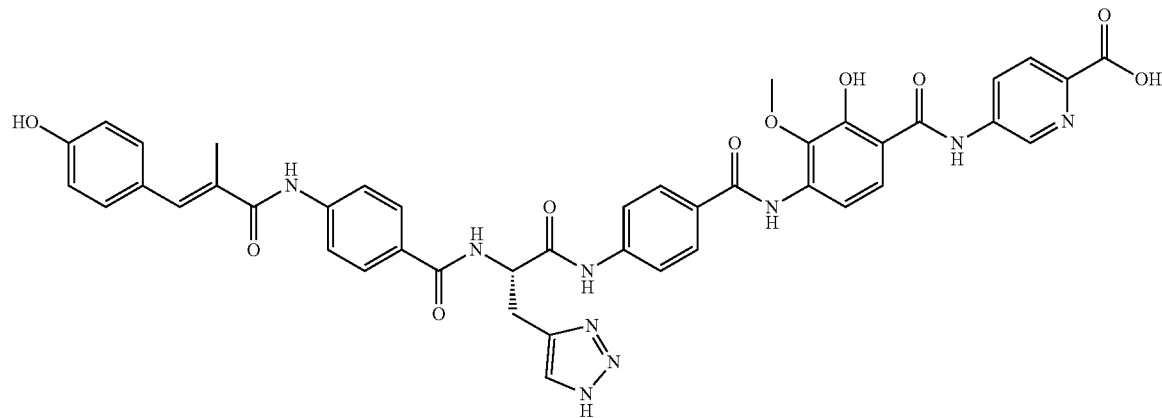
Compound 21
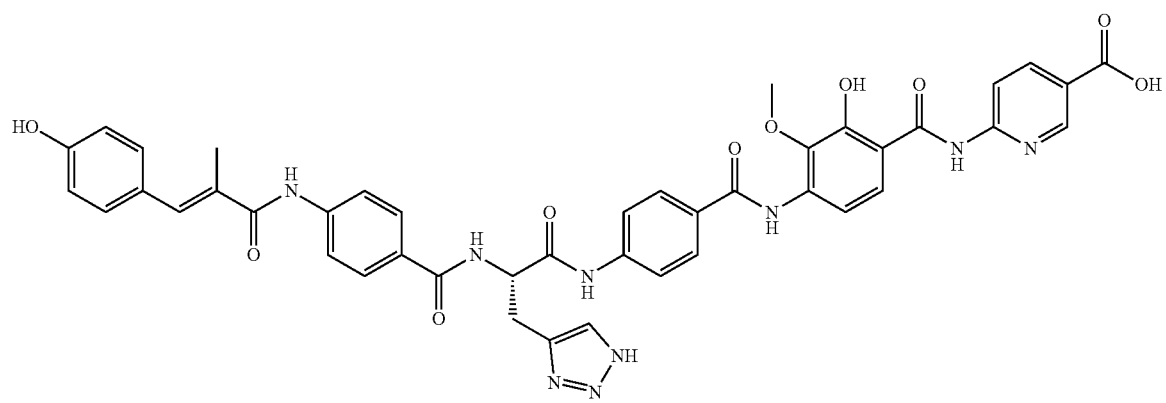
Compound 22
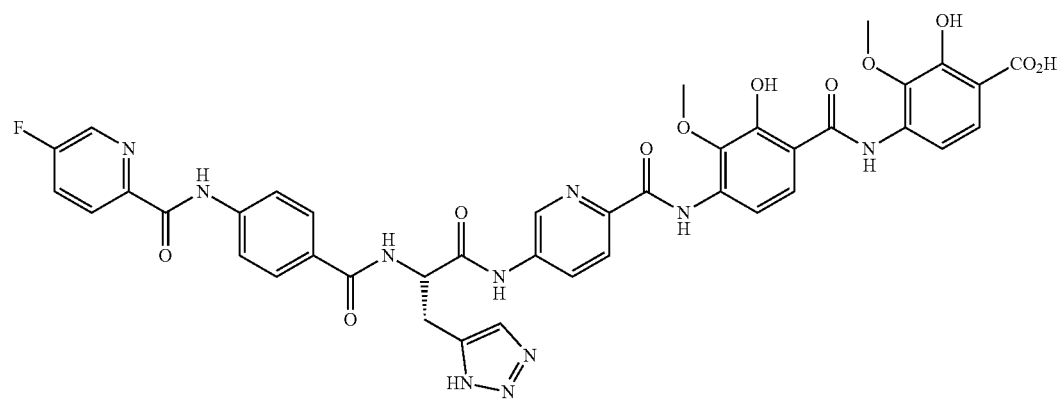

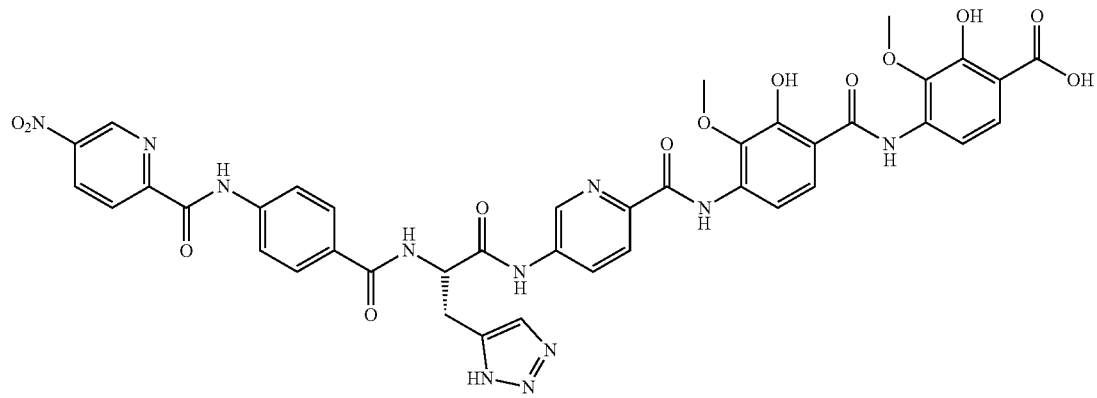

Compound 23

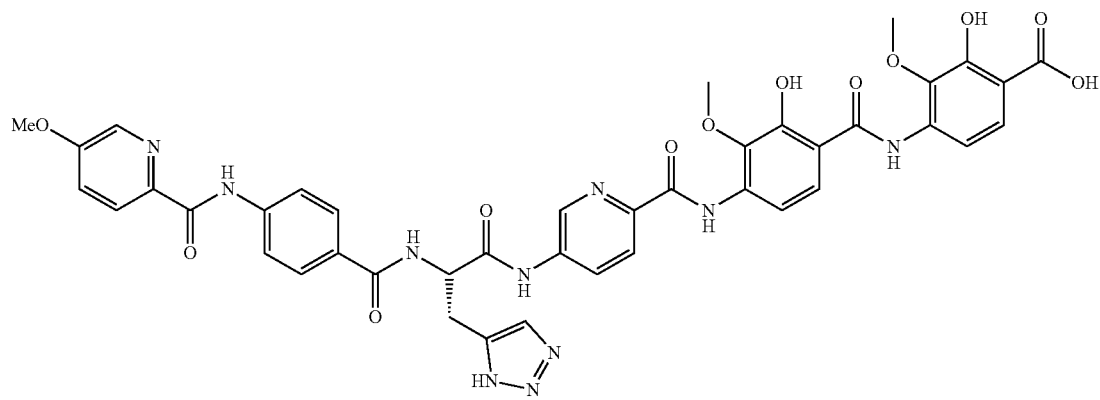

Compound 24

The compounds of the proposed solution may be used in a method of treatment of diseases, in particular for use in a method of treatment of bacterial infections caused by gram-negative or gram-positive bacterial strains.

The bacterial infection may be an infection caused by one of the genus *Acinetobacter, Bordatella, Borellia, Brucella, Camphylobacter, Chlamydia, Chlamydophila, Enterobacter, Escherichia, Francisella, Haemophilus, Helicobacter, Klebsiella, Legionella, Leptospira, Morganella Moraxella, Neisseria, Proteus, Pseudomonas, Rickettsia, Shigella, Salmonella, Stenotrophomonas, Treponema* or *Yersinia*, in particular an infection caused by one of the genus *Escherichia, Enterobacter, Salmonella, Klebsiella, Pseudomonas, Haemophilus, Shigella, Proteus* or *Morganella*.

In a further embodiment the bacterial infection is an infection caused
by a gram-positive bacterium, particularly an infection by one of the genus *Bacillus, Chlostridium, Corynebacterium, Enterococcus, Listeria, Micrococcus, Staphylococcus* or *Streptococcus*, further in particular by one of the genus of *Staphylococcus, Streptococcus, Bacillus* or *Micrococcus* or
by a bacterium of the family of Mycobacteriaceae, in particular of the genus *Mycobacterium*, further in particular an infection by one of *Mycobacterium tuberculosis, Mycobacterium leprae, Mycobacterium ulcerans* or *Mycobacterium avium*, or
by a bacterium of the family of Mycoplasmataceae, in particular of the genus *Mycoplasma*, further in particular an infection by *Mycoplasma* pneumonia.

For this purpose, the present compounds may be provided in a pharmaceutical acceptable form. Pharmaceutically acceptable salts of the present compounds mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The present compounds form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the solution are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

In a preferred embodiment formulations of the present albicidin derivatives are provided which contain cyclodextrins for improving solubility of the otherwise poorly soluble albicidin derivatives. Cyclodextrins are used in a concentration of 20-40%, preferably 25-35%, more preferably 28-30%.

Salts with a pharmaceutically unacceptable anion such as, for example, trifluoroacetate likewise belong within the framework of the solution as useful intermediates for the preparation or purification of pharmaceutically acceptable salts and/or for use in non-therapeutic, for example in vitro, applications.

The proposed solution furthermore relates to pharmaceutical preparations (or pharmaceutical compositions) which contain an effective amount of at least one of the present compounds and/or its pharmaceutically acceptable salts and a pharmaceutically acceptable carrier, i. e. one or more pharmaceutically acceptable carrier substances (or vehicles) and/or additives (or excipients). The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the solution are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatine capsules it is possible to use, for example, lactose, corn starch or derivatives thereof, talc, stearic acid or its salts, etc. Carrier substances for soft gelatine capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the present compounds and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

A prodrug is a precursor chemical compound of a biological active compound of the solution. Instead of administering the active compound or drug, a prodrug might be used instead to improve the absorption, distribution, metabolization and excretion. Prodrugs are often designed to improve bioavailability when a drug itself is poorly absorbed from the gastrointestinal tract. A prodrug may also be used to improve the selectively of the drug. This reduces adverse or unintended effects of a drug, especially important in treatments like chemotherapy, which can have severe unintended and undesirable side effects.

In addition to the active compound according to the solution and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavourings, aromatizers, thickeners, diluents, buffer substances, solvents, solubilizers, agents for achieving a depot effect, salts for altering the osmotic pressure, coating agents or antioxidants. They can also contain two or more of the present compounds and/or their pharmaceutically acceptable salts. In case a pharmaceutical preparation contains two or more of the present compounds the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the present compounds allows a great deal of control over the biological and physicochemical properties of the compounds and thus allows the selection of such desired compounds. Furthermore, in addition to at least one compound and/or its pharmaceutically acceptable salts, the pharmaceutical preparations can also contain one or more other therapeutically or prophylactically active ingredients. When using the present compounds the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

The compounds of the solution may also exist in various polymorphous forms, for example as amorphous and crystalline polymorphous forms. All polymorphous forms of the compounds of the solution belong within the framework of the solution and are a further aspect of the solution.

The compounds of the solution may be present as optical isomers or as mixtures thereof. The solution relates both to the pure isomers and all possible isomeric mixtures and is hereinafter understood as doing so, even if stereochemical details are not specifically mentioned in every case. Enantiomeric mixtures of compounds of the general formula 1, which are obtainable by the process or any other way, may be separated in known manner—on the basis of the physical-chemical differences of their components—into pure enantiomers, for example by fractional crystallisation, distillation and/or chromatography, in particular by preparative HPLC using a chiral HPLC column.

According to the solution, apart from separation of corresponding isomer mixtures, generally known methods of diastereoselective or enantioselective synthesis can also be applied to obtain pure diastereoisomers or enantiomers, e.g. by carrying out the method described hereinafter and using educts with correspondingly suitable stereochemistry.

It is advantageous to isolate or synthesise the biologically more active isomer, provided that the individual compounds have different biological activities.

Methods of Synthesis

General methods for synthesizing the compounds of the solution are described in detail in WO 2014/125075 A1.

A first procedure for the synthesis of albicidin-derivatives with variations of the B ring (such as compounds 1-5, 8-9) may comprise the steps according to the general reaction scheme 1:

Reaction scheme 1
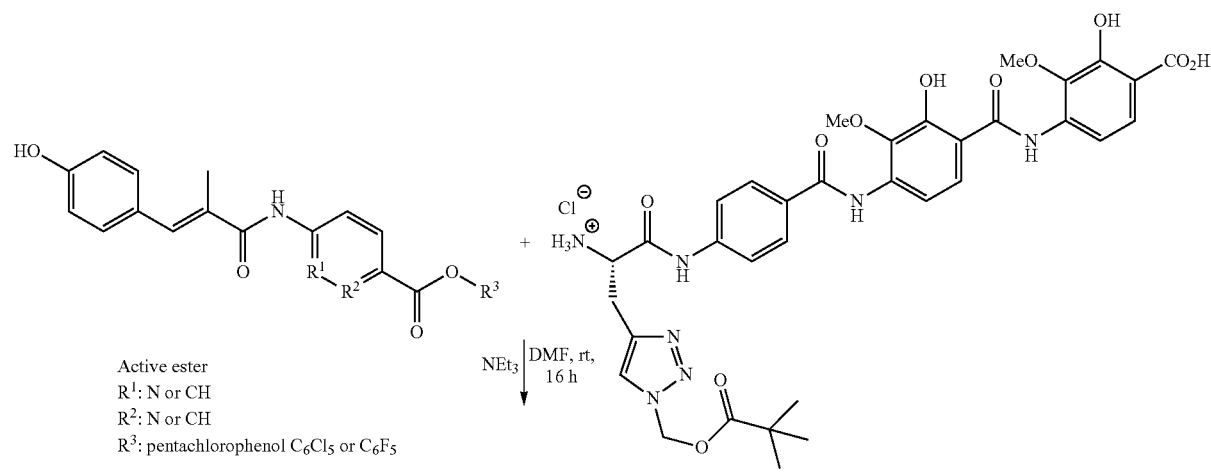
Active ester
R[1]: N or CH
R[2]: N or CH
R[3]: pentachlorophenol $C_6Cl_5$ or $C_6F_5$
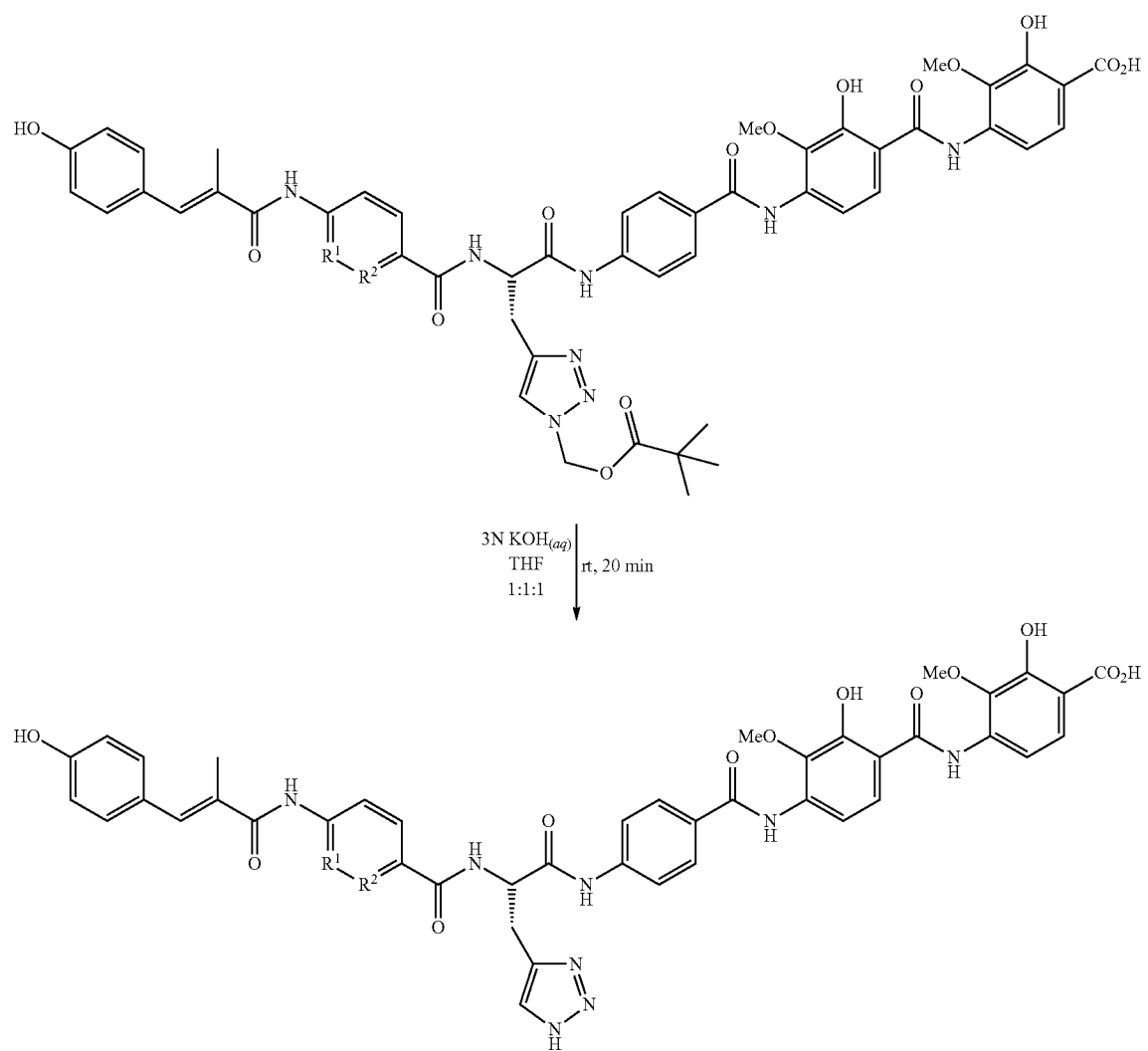

The amine is reacted with the active ester in basic conditions, preferably in the presence of triethylamine. Specifically, the corresponding amine is dissolved in anhydrous N,N'-dimethylformamide under an atmosphere of nitrogen. After the addition of triethylamine the active ester (see Reaction scheme 1) is added and the reaction mixture is stirred for 16 h in the dark. All volatiles were removed under high vacuum. The residue is dissolved in a mixture of equal volumes of THF (one part) and Methanol (one part) and cooled to 0° C. 3 N $KOH_{(aq)}$ (one part) is added dropwise, and the reaction mixture is stirred for 20 minutes. After completion of the reaction all volatiles were removed, and the residue was purified by means of preparative HPLC.

Another general procedure according to reaction scheme 2 enables the synthesis of albicidin-derivatives with variations of building block D:

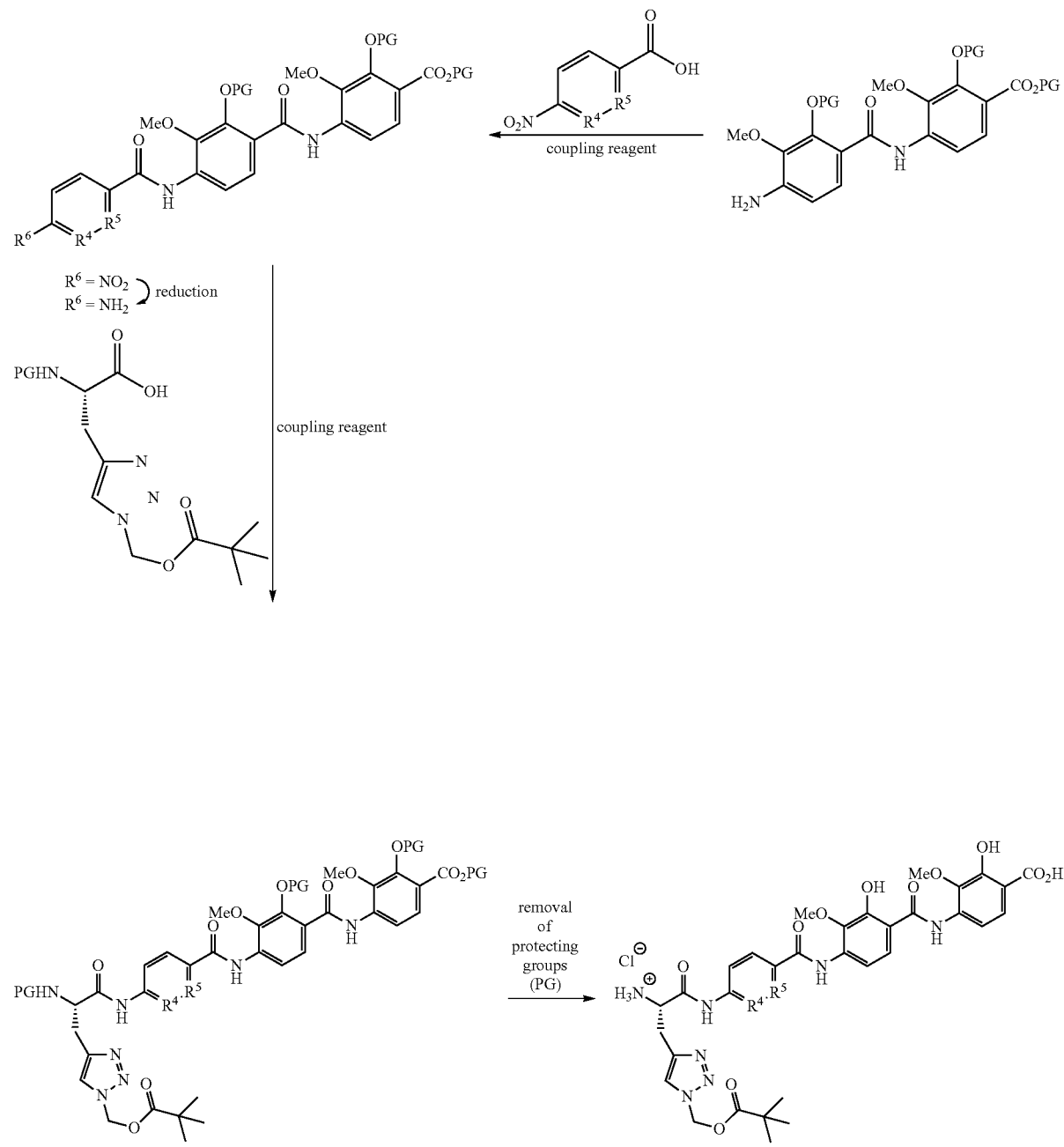

Building block D:
$R^4$: N or CH
$R^5$: N or CH

After synthesis of the so obtained tetrapeptide, the assembly of the hexapeptide would follow the reaction scheme 1.
Another general procedure for the synthesis of albicidin-derivatives with variations of the E and F ring (such as compounds 6 or 7) may comprise the steps according to the general reaction scheme 3:
Reaction scheme 3
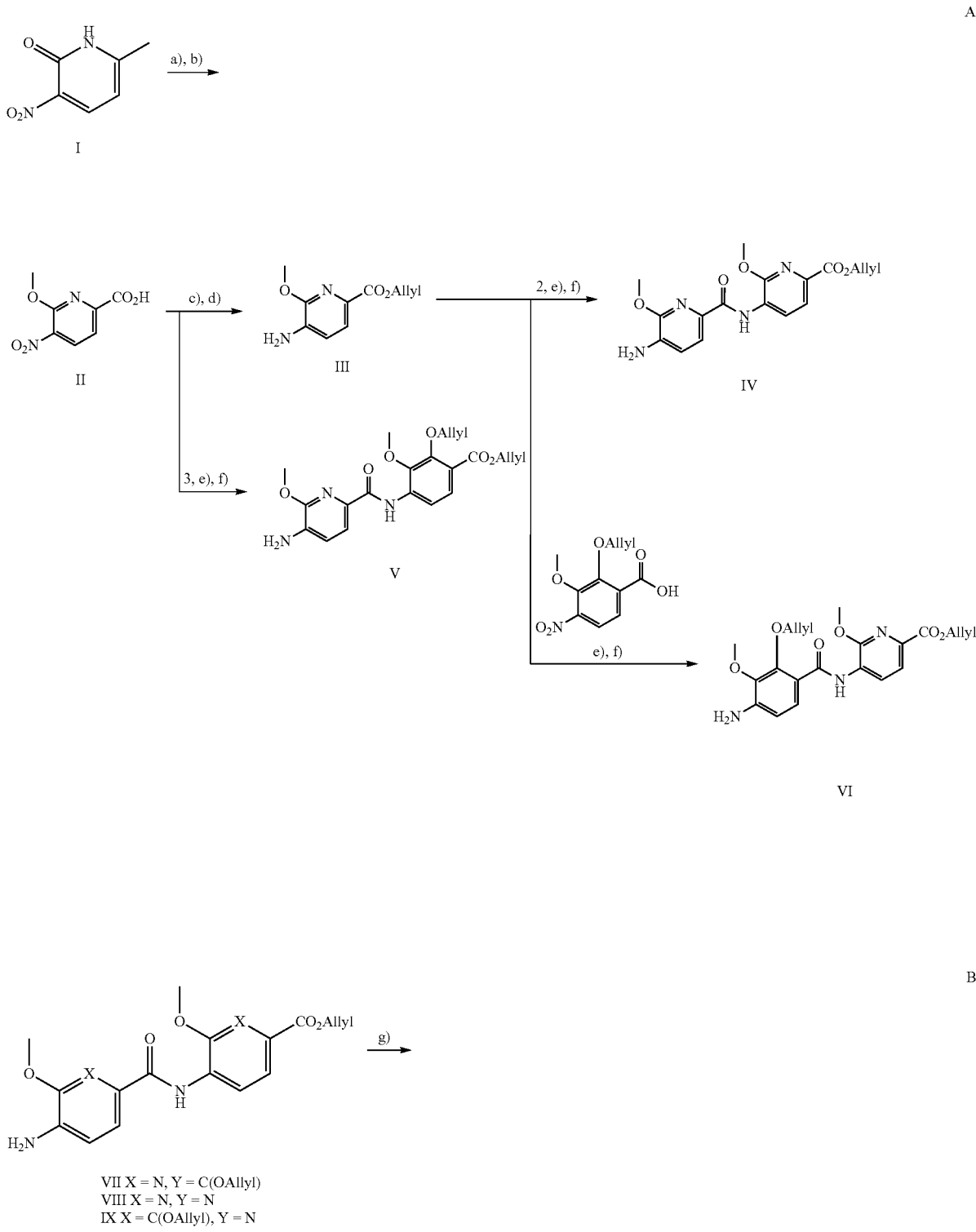

-continued

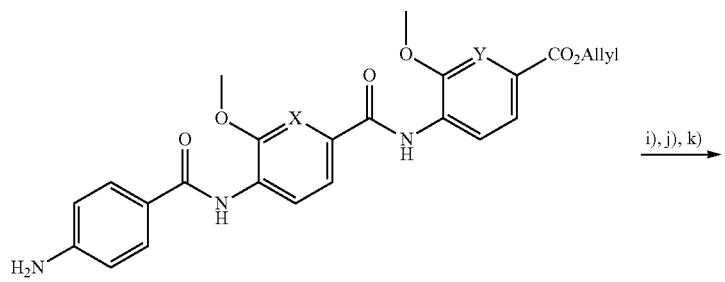

X X = N, Y = C(OAllyl)
XI X = N, Y = N
XII X = C(OAllyl), Y = N i), j), k) →

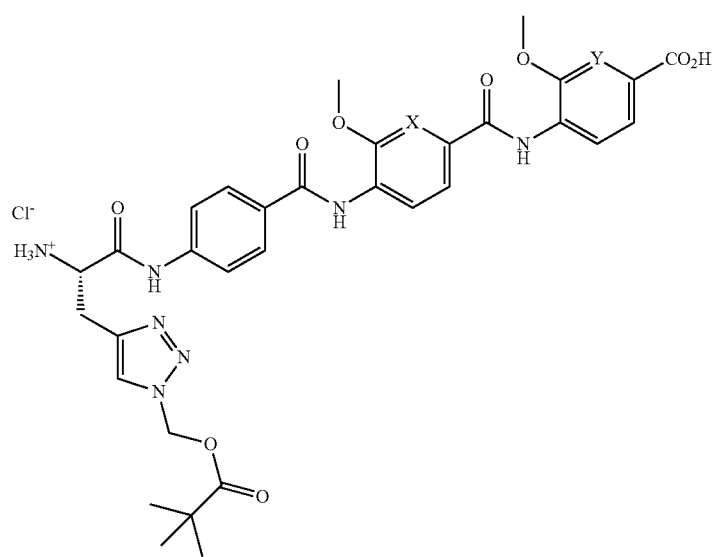

XIII X = N, Y = C(OH)
XIV X = N, Y = N
XV X = C(OH), Y = N

Reagents and conditions. A) Synthesis of EF-dipeptides IV-VI: a) Ag$_2$CO$_3$, MeI, toluene, 80° C., 16 h, 83%; b) CrO$_3$, conc. H$_2$SO$_4$, 0° C. → RT, 16 h, 69%; c) SOCl$_2$, allyl alcohol, RT, 16 h, 93%; d) Zn, AcOH, EtOH, 0° C., 2 h, quant.; e) triphosgene, 2,4,6-collidine, DIPEA, THF, 0° C. → RT, 16 h, 69-90%; f) Zn, AcOH, EtOH/THF (2:1), 0° C. → RT, 16 h, 87%-quant.; B) Synthesis of CDEF-tetrapeptides XIII-XV: g) Et$_3$N, pNBC, THF, −15° C., 30 min, 88-90%; h) Zn, AcOH, EtOH/THF (3:1), 0° C. → RT, 16 h, quant., 48-93%; i) BocHN-AzaHis(POM)-OH, EEDQ, THF, RT, 16 h, 85-88%; j) morpholine, Pd(PPh$_3$)$_4$, THF, RT, 16 h, 70-90%; k) for X: 4N HCl in dioxane, RT 2 h, quant.; for XI and XII: TFA, CH$_2$Cl$_2$, RT, 15 min, then 0.1N HCl, quant.

After the synthesis of the tetrapeptides XIII-XV, the assembly of the hexapeptide would follow the same route as depicted in reaction scheme 1

The solution is explained in more detail by means of the following examples.

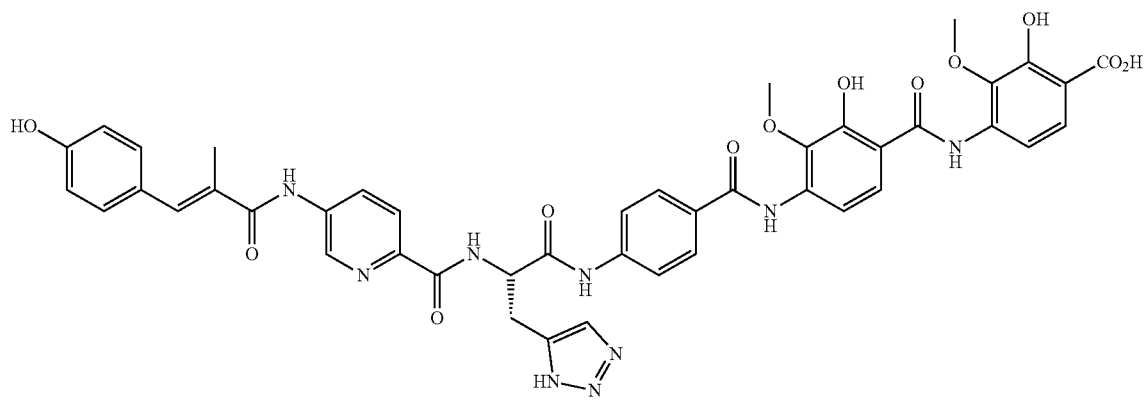

Compound 1

Compound 1 is synthesized in a multistep synthesis route in accordance to reaction scheme 1 as follows:

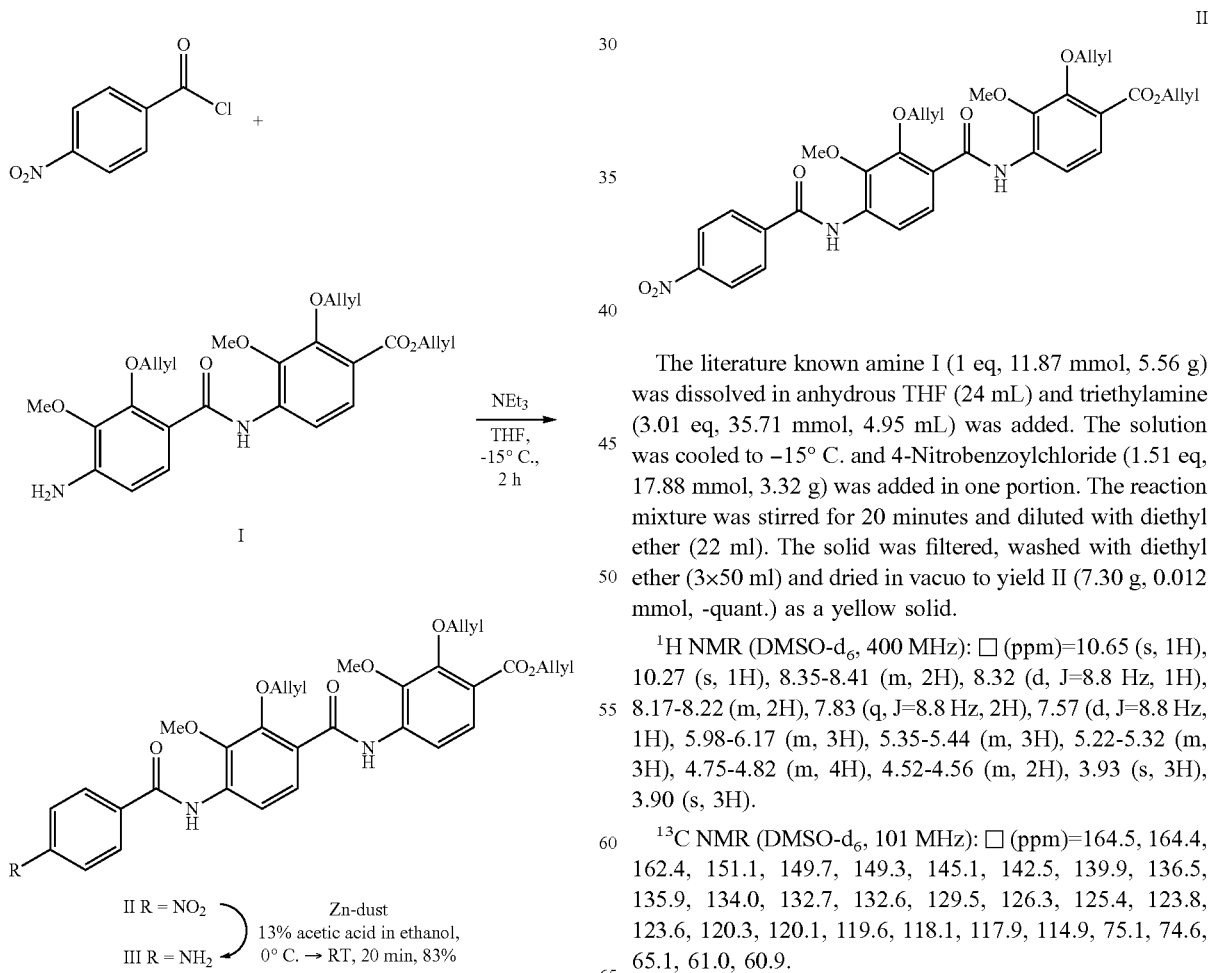

Preparation of Compound II:

The literature known amine I (1 eq, 11.87 mmol, 5.56 g) was dissolved in anhydrous THF (24 mL) and triethylamine (3.01 eq, 35.71 mmol, 4.95 mL) was added. The solution was cooled to −15° C. and 4-Nitrobenzoylchloride (1.51 eq, 17.88 mmol, 3.32 g) was added in one portion. The reaction mixture was stirred for 20 minutes and diluted with diethyl ether (22 ml). The solid was filtered, washed with diethyl ether (3×50 ml) and dried in vacuo to yield II (7.30 g, 0.012 mmol, -quant.) as a yellow solid.

$^1$H NMR (DMSO-$d_6$, 400 MHz): □ (ppm)=10.65 (s, 1H), 10.27 (s, 1H), 8.35-8.41 (m, 2H), 8.32 (d, J=8.8 Hz, 1H), 8.17-8.22 (m, 2H), 7.83 (q, J=8.8 Hz, 2H), 7.57 (d, J=8.8 Hz, 1H), 5.98-6.17 (m, 3H), 5.35-5.44 (m, 3H), 5.22-5.32 (m, 3H), 4.75-4.82 (m, 4H), 4.52-4.56 (m, 2H), 3.93 (s, 3H), 3.90 (s, 3H).

$^{13}$C NMR (DMSO-$d_6$, 101 MHz): □ (ppm)=164.5, 164.4, 162.4, 151.1, 149.7, 149.3, 145.1, 142.5, 139.9, 136.5, 135.9, 134.0, 132.7, 132.6, 129.5, 126.3, 125.4, 123.8, 123.6, 120.3, 120.1, 119.6, 118.1, 117.9, 114.9, 75.1, 74.6, 65.1, 61.0, 60.9.

HRMS (ESI): m/z calc. for $C_{32}H_{31}N_3O_{10}$ [M+H]$^+$: 618.2082; found 618.2079.

Preparation of Compound III:

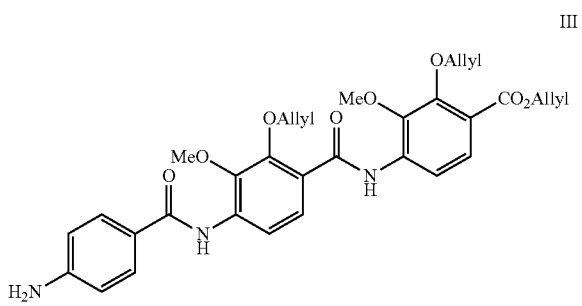

Compound II (1 eq, 12.84 mmol, 7.30 g) was suspended in a mixture of ethanol (800 ml) and acetic acid (100 ml) and cooled to 0° C. Zinc dust (33.80 g) was added portion wise. After 20 min the reaction was proven to be complete (verified by TLC-control). The solid was filtered and washed with DCM (3×100 ml). The combined liquids were evaporated to dryness. The residue was taken up in DCM (300 ml) and saturated aqueous $NaHCO_3$—Solution (300 ml). The aqueous phase was further extracted twice with DCM (2×100 ml). The combined organic fractions were washed successively with saturated aqueous $NaHCO_3$—Solution (1×300 ml), distilled water (1×300 ml) and brine (1×300 ml), dried over $Na_2SO_4$ and evaporated to obtain III (5.79 g, 9.85 mmol, 83%) as a yellow solid.

$^1$H NMR (DMSO-$d_6$, 400 MHz): □ (ppm)=10.65 (s, 1H), 9.19 (s, 1H), 8.34 (d, J=8.8 Hz, 1H), 8.01 (d, J=8.8 Hz, 1H), 7.79 (d, J=8.8 Hz, 1H), 7.68-7.74 (m, 2H), 7.57 (d, J=9.0 Hz, 1H), 6.59-6.65 (m, 2H), 5.98-6.18 (m, 3H), 5.89 (s, 2H), 5.40 (tdd, J=11.5, 5.6, 1.5 Hz, 3H), 5.21-5.32 (m, 3H), 4.75-4.83 (m, 4H), 4.54 (d, J=5.8 Hz, 2H), 3.93 (s, 3H), 3.92 (s, 3H).

$^{13}$C NMR (DMSO-$d_6$, 101 MHz): □ (ppm)=165.0, 164.4, 162.4, 152.7, 151.1, 149.4, 143.3, 142.4, 137.2, 136.6, 134.0, 132.7, 132.6, 129.4, 126.3, 125.6, 121.7, 120.2, 120.1, 120.0, 118.1, 117.8, 117.5, 114.8, 112.7, 75.1, 74.5, 65.1, 61.0, 60.9.

HRMS (ESI): m/z calc. for $C_{32}H_{33}N_3O_8$ [M+H]$^+$: 588.2340; found 588.2343.

Preparation of Compound IV:

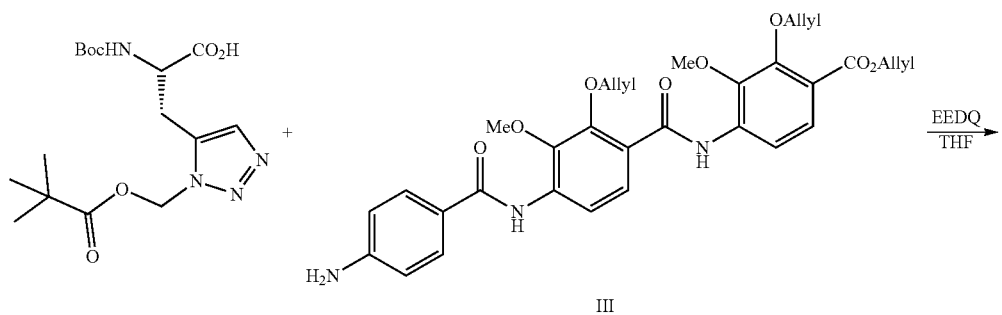

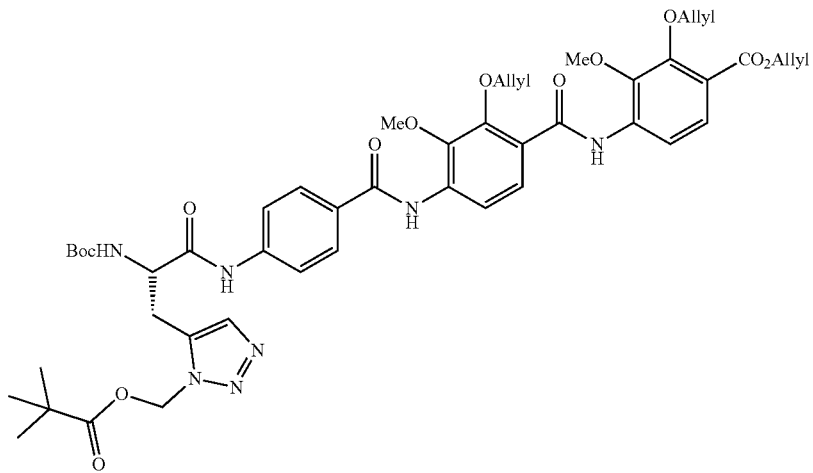

Literature known Boc-Q-(1-pivaloyloxymethyl)-1,2,3-triazol-4-yl)-Alanine (1.46 eq, 3.99 mmol, 1.48 g) was dissolved in THF (20 ml) and cooled to 0° C. N-Ethoxycarbonyl-2-ethoxy-1,2-dihydroqinoline (EEDQ) (3.00 eq, 8.20 mmol, 2.03 g) was added and after 5 minutes compound III (1 eq, 2.72 mmol, 1.6 g) was added. The reaction mixture was slowly warmed to room temperature and stirred for 16 h. All volatiles were removed in vacuo and the residue was taken up in ethyl acetate (100 ml). The organic fraction was washed with saturated aqueous $NaHCO_3$—Solution (3×50 ml) and brine (1×50 ml), dried over $Na_2SO_4$ and evaporated. The residue was purified via flash chromatography on silica gel eluting with 1-15% acetone in DCM. Compound IV (1.90 g, 2.02 mmol, 74%) was obtained as a light-yellow solid.

$^1$H NMR (DMSO-$d_6$, 500 MHz): □=10.65 (s, 1H), 10.41 (s, 1H), 9.63 (s, 1H), 8.33 (d, J=8.7 Hz, 1H), 7.92-7.99 (m, 4H), 7.74-7.84 (m, 3H), 7.57 (d, J=8.7 Hz, 1H), 7.20 (m, 1H), 6.29 (s, 2H), 5.99-6.16 (m, 3H), 5.22-5.45 (m, 6H), 4.81 (d, J=6.1 Hz, 2H), 4.77 (d, J=5.5 Hz, 2H), 4.54 (d, J=5.6 Hz, 3H), 3.93 (d, J=6.1 Hz, 6H), 2.96-3.16 (m, 2H), 1.26-1.38 (m, 9H), 1.09 ppm (s, 9H)

$^{13}$C NMR (DMSO-$d_6$, 126 MHz): □=176.4, 170.7, 164.8, 164.4, 162.4, 155.3, 151.1, 149.5, 144.2, 143.4, 142.5, 142.2, 136.5, 133.9, 132.7, 132.6, 128.7, 128.5, 126.3, 125.5, 124.1, 122.7, 120.3, 120.1, 118.7, 118.6, 118.1, 117.8, 114.8, 78.3, 75.1, 74.5, 69.8, 65.1, 61.0, 60.9, 54.9, 38.1, 28.1, 26.4 ppm HRMS (ESI): m/z calc. for $C_4H_{57}N_7O_{13}$ $[M+H]^+$ 940.4087, found 940.4088.

Preparation of Compound V:

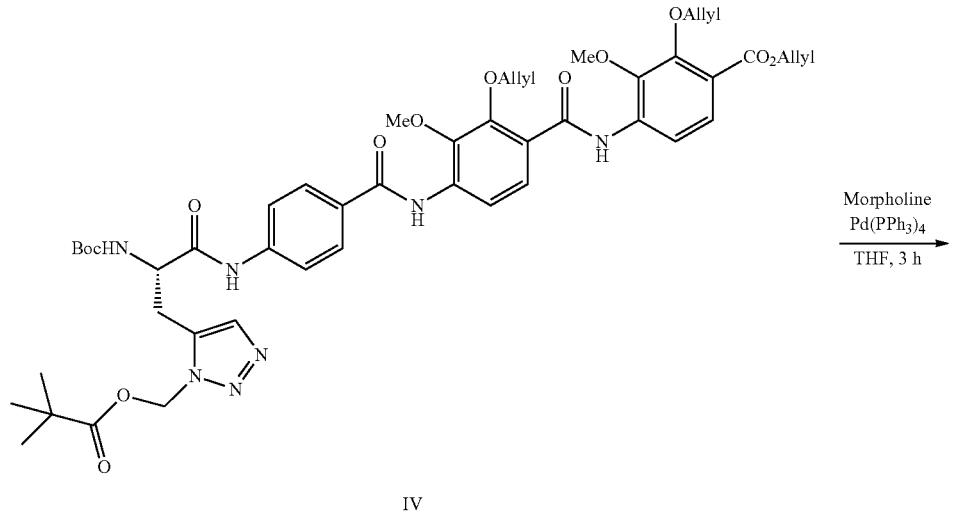

IV

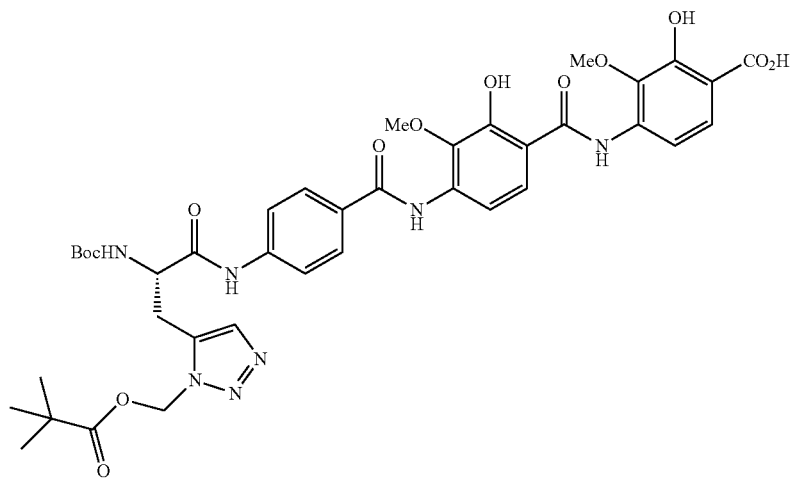

V

Tetrapeptide IV (1 eq, 2.00 mmol, 1.88 g) was dissolved in THF (5 ml) and morpholine (20 eq, 40.00 mmol, 3.48 g) and tetrakis(triphenylphosphin)palladium(0) (0.3 eq, 0.60 mmol, 693 mg) were added. The mixture was stirred for 2.5 h shielded from light. All volatiles were removed in vacuo and the residue was purified via flash chromatography on C-18-material eluting with 5 to 50% acetonitrile in water. Compound V (1.24 g, 1.51 mmol, 76%) was obtained as a white solid.

$^1$H NMR (DMSO-$d_6$, 500 MHz): $\square$=11.51 (s, 1H), 11.16 (s, 1H), 9.64 (s, 1H), 8.05 (d, J=9.0 Hz, 1H), 7.96 (d, J=8.9 Hz, 3H), 7.81 (d, J=8.9 Hz, 1H), 7.76 (d, J=8.7 Hz, 2H), 7.59 (dd, J=8.9, 3.8 Hz, 2H), 7.17-7.20 (m, 1H), 6.29 (s, 2H), 4.38-4.44 (m, 1H), 3.92 (s, 3H), 3.78 (s, 3H), 2.97-3.15 (m, 2H), 1.26-1.38 (m, 9H), 1.09 ppm (s, 9H)

$^{13}$C NMR (DMSO-$d_6$, 126 MHz): $\square$=176.4, 172.0, 164.8, 164.4, 163.3, 154.3, 149.7, 146.2, 143.4, 142.2, 140.1, 137.8, 136.1, 135.9, 128.7, 128.6, 128.3, 125.4, 124.1, 118.7, 116.1, 114.8, 110.3, 109.0, 78.3, 69.8, 60.5, 60.2, 59.7, 38.1, 28.1, 26.4 ppm HRMS (ESI): m/z calc. for $C_{39}H_{45}N_7O_{13}$ [M−H]$^-$ 818.3003, found 818.3009.

Preparation of Compound VI:

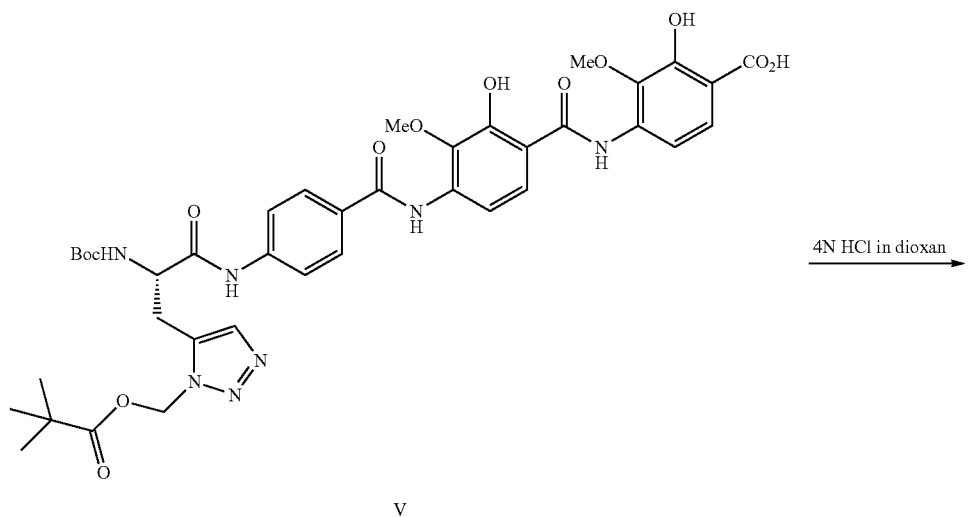

V

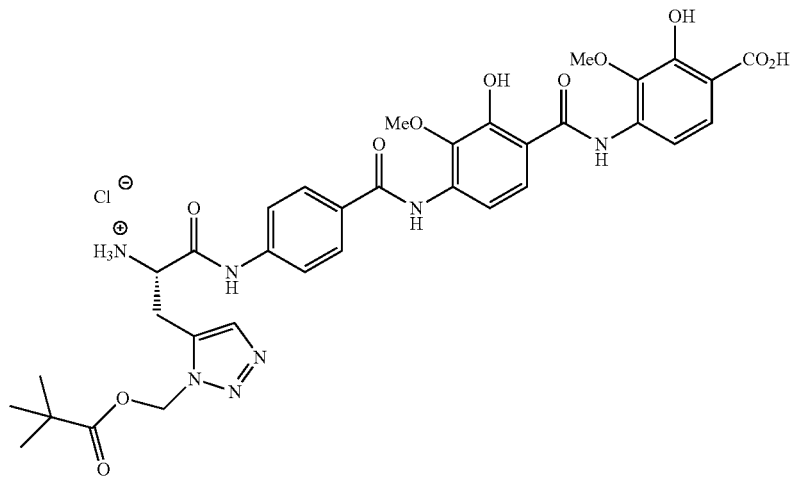

VI

Tetrapeptide V (1.00 eq, 1.51 mmol, 1.24 g) was dissolved 4 N HCl in dioxane and stirred for 1 hour. The solvent was evaporated in vacuo and the product VI (1.13 g, 1.50 mmol, quant.) was obtained as white solid. Compound VI was used in the next step without further characterization.

HRMS (ESI): m/z calc. for $C_{34}H_{37}N_7O_{11}$ [M+H]$^+$: 720.2624, found: 720.2624.

Preparation of Active Ester XI

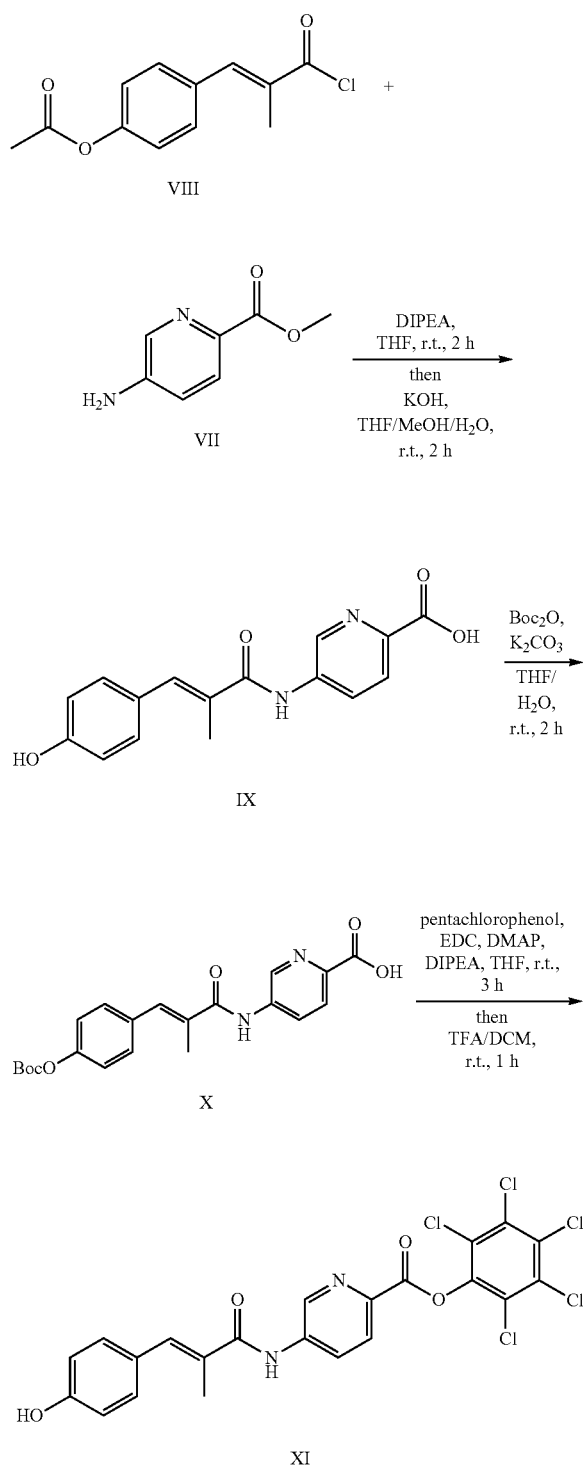

Commercially available compound VII (1.0 eq, 1.38 mmol, 210 mg) and DIPEA (2.6 eq, 3.59 mmol, 0.6 mL) were dissolved in THF (3 mL). The literature known acyl chloride VIII (1.3 eq, 1.79 mmol, 428 mg) was added to the reaction mixture at 0° C. After 2 h at r.t. the resulting slurry was diluted with Et$_2$O (30 mL), the formed precipitated was filtered and washed with Et$_2$O. The obtained crude material was dissolved in THF/MeOH (1:2, 5 mL) and treated with 5 N KOH (5 eq, 6.9 mmol 1.4 mL). After 2 h at r.t. the reaction mixture was concentrated in vacuo and diluted with H$_2$O (10 mL). The product was precipitated with 6 N HCl, filtered and washed with H$_2$O. Compound IX was obtained as a colorless solid (330 mg, 1.11 mmol, 80%).

$^1$H NMR (DMSO-d$_6$, 500 MHz): □=10.39 (s, 1H), 8.99 (d, J=2.4 Hz, 1H), 8.33 (dd, J=8.7, 2.4 Hz, 1H), 8.05 (d, J=8.5 Hz, 1H), 7.36 (d, J=8.7 Hz, 2H), 7.33 (s, 1H), 6.85 (d, J=8.5 Hz, 2H), 2.12 ppm (d, J=1.1 Hz, 3H)

$^{13}$C NMR (DMSO-d$_6$, 126 MHz): □=169.3, 165.6, 157.8, 142.0, 140.7, 139.2, 134.9, 131.5, 129.0, 127.0, 126.4, 125.4, 115.5, 14.5 ppm HRMS (ESI): m/z calc. for $C_{16}H_{14}N_2O_4$ [M+H]$^+$: 299.1026, found: 299.1032.

Compound IX (1 eq, 1.01 mmol, 300 mg) and DMAP (0.1 eq, 0.10 mmol, 12 mg) were dissolved in THF (3 m). After addition of 10% K$_2$CO$_3$ (1.1 eq, 1.12 mmol, 1.5 mL), the resulting mixture was treated with Boc$_2$O (1.1 eq, 1.12 mmol, 241 mg) and stirred for 2 h at r.t. Afterwards, it was diluted with 10% KHSO$_4$ (30 mL) and extracted with EtOAc (3×30 mL). The combined organic layers were dried over Na$_2$SO$_4$ and concentrated in vacuo. Compound X was obtained as a colorless solid (370 mg, 0.93 mmol, 92%).

$^1$H NMR (DMSO-d$_6$, 400 MHz): □ (ppm)=$^1$H NMR (DMSO-d$_6$, 400 MHz): d=10.47 (s, 1H), 8.98 (d, J=2.5 Hz, 1H), 8.33 (dd, J=8.5, 2.5 Hz, 1H), 8.05 (d, J=8.5 Hz, 1H), 7.54 (d, J=8.8 Hz, 2H), 7.39 (s, 1H), 7.28 (d, J=8.8 Hz, 2H), 2.12 (d, J=1.5 Hz, 3H), 1.49 ppm (s, 9H)

$^{13}$C NMR (DMSO-d$_6$, 101 MHz): □=169.0, 165.8, 151.2, 150.4, 142.5, 141.0, 138.9, 133.6, 133.3, 132.6, 130.8, 126.9, 125.4, 121.7, 83.6, 27.4, 14.5 ppm Compound X (1 eq, 0.85 mmol, 340 mg), EDC*HCl (1.2 eq, 1.024 mmol, 196 mg), DMAP (0.1 eq, 0.085 mmol, 10 mg) and DIPEA (1.3 eq, 1.11 mmol, 0.2 mL) were dissolved in THF (4 mL). After 1 min at r.t., pentachlorophenol (1.1 eq, 0.94 mmol, 250 mg) was added and resulting the reaction mixture was stirred for another 3 h at r.t. Afterwards, the solution was dissolved with EtOAc (50 mL) and washed with H$_2$O (2×30 mL), 10% KHSO$_4$ (2×30 mL) and brine (1×30 mL). All volatiles were removed in vacuo and the obtained crude material was dissolved in TFA/DCM (1:2, 2 mL). After 1 h at r.t. the reaction mixture was diluted with cold Et$_2$O/hexane (4:1, 30 mL), the formed precipitate was filtered, and washed with Et$_2$O. Active ester XI was obtained as a colorless solid (289 mg, 0.52 mmol, 62%).

$^1$H NMR (DMSO-d$_6$, 400 MHz): □=10.64 (s, 1H), 9.14 (d, J=2.5 Hz, 1H), 8.51 (dd, J=8.8, 2.5 Hz, 1H), 8.34 (d, J=8.5 Hz, 1H), 7.36-7.41 (m, 3H), 6.86 (d, J=8.8 Hz, 2H), 2.13-2.16 ppm (m, 3H)

Due to the low solubility of the compound, no $^{13}$C-Data were recorded.

HRMS (ESI): m/z calc. $C_{22}H_3Cl_5N_2O_4$ [M+H]$^+$: 546.9361, found: 564.0363.

Preparation of Compound 1:
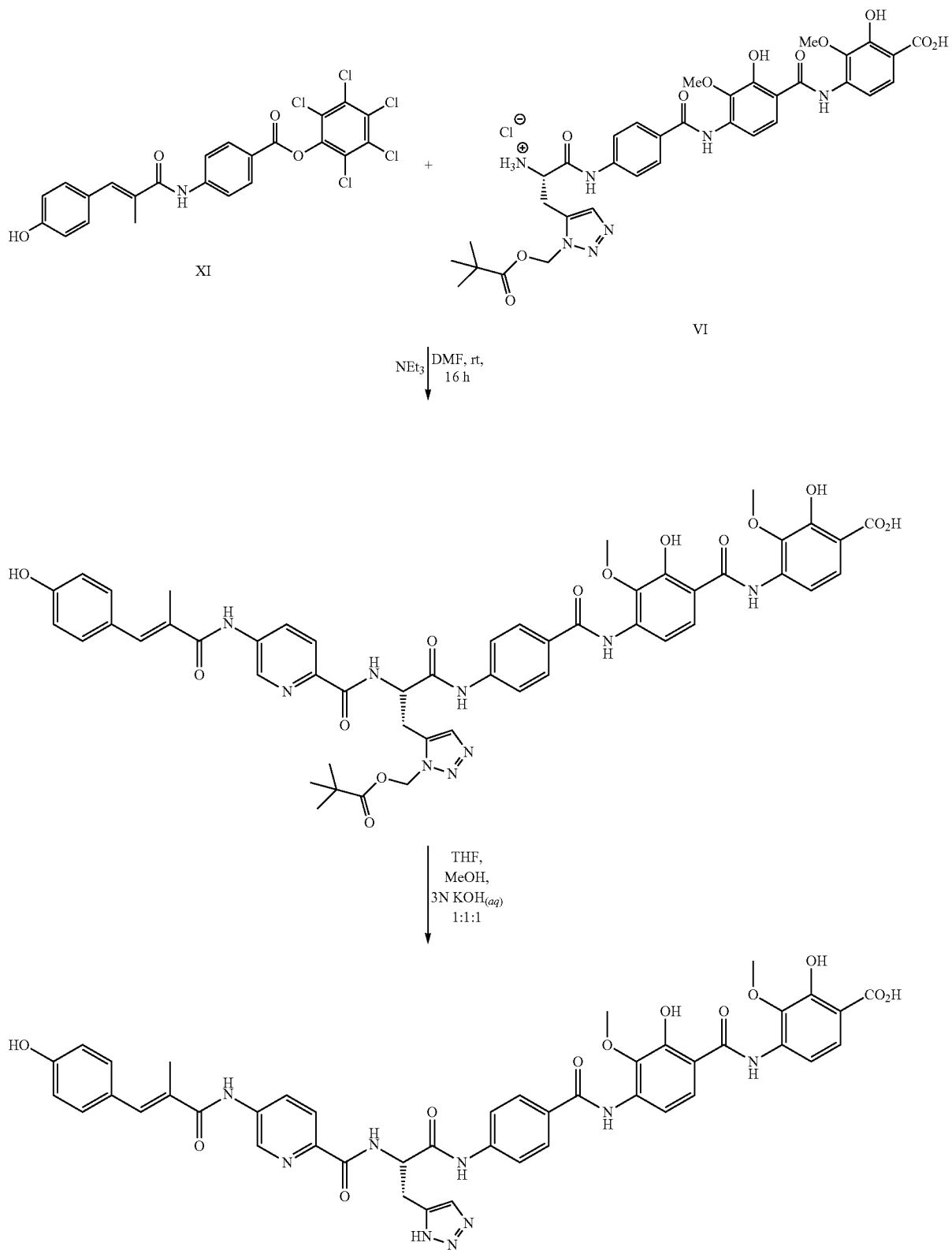

Compound VI (1 eq, 0.053 mmol, 40 mg) was dissolved in DMF (2 ml) and triethylamine (5 eq, 0.26 mmol, 36 μL) was added. After adding the active ester (1.1 eq, 0.058 mmol, 32.0 mg), the mixture was stirred for 16 h shielded from light. All volatiles were removed in vacuo. The residue was dissolved in a mixture of Methanol (1 ml) and THF (1 ml) and cooled to 0° C. 3 N KOH$_{(aq)}$ (1 ml) was added dropwise. After 15 min of stirring, 550 μl of 6 N HCl$_{(aq)}$ were added dropwise. The resulting mixture was evaporated to dryness. The residue was purified via prep HPLC. Compound 1 (19 mg, 0.021 mmol, 41%) was obtained as a white fluffy solid.

Analytical Data for Compound 1:
$^1$H NMR (DMSO-d$_6$, 700 MHz): □=11.60 (br. s, 1H), 11.54 (s, 1H), 11.18 (s, 1H), 10.57 (s, 1H), 10.37 (s, 1H), 9.82 (br. s, 1H), 9.68 (s, 1H), 8.98 (d, J=2.3 Hz, 1H), 8.79 (d, J=8.1 Hz, 1H), 8.34 (dd, J=8.5, 2.1 Hz, 1H), 8.05 (d, J=8.8 Hz, 1H), 8.01 (d, J=8.5 Hz, 1H), 7.98 (d, J=8.5 Hz, 2H), 7.81 (d, J=8.5 Hz, 1H), 7.76 (d, J=8.5 Hz, 2H), 7.58 (t, J=9.4 Hz, 2H), 7.37 (d, J=8.5 Hz, 2H), 7.33 (s, 1H), 6.85 (d, J=8.3 Hz, 2H), 4.99 (s, 1H), 3.92 (s, 3H), 3.78 (s, 3H), 3.34 (d, J=6.2 Hz, 2H), 2.13 ppm (m, 3H)

HRMS (ESI): m/z calculated for C$_{44}$H$_{39}$N$_9$O$_{12}$ [M+H]$^+$: 886.2791; found 886.2778.

Compound 2

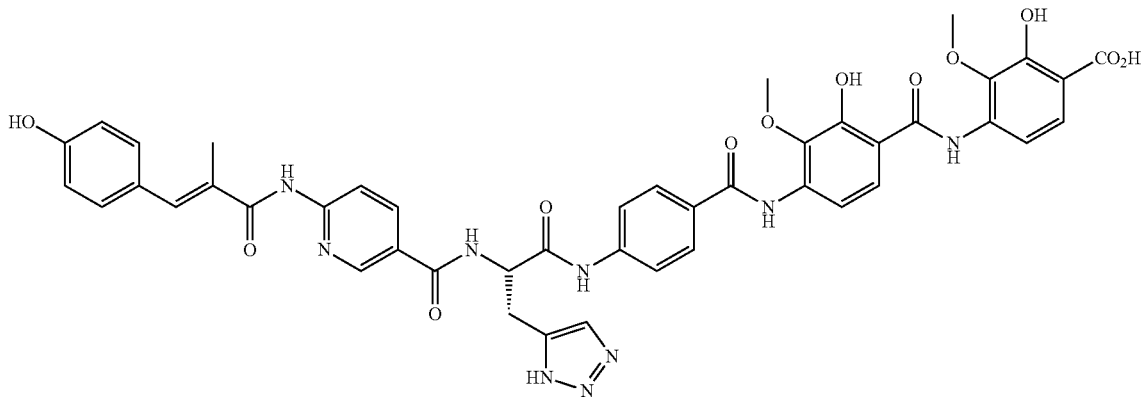

$^1$H NMR (DMSO-d$_6$, 700 MHz): □=11.52 (s, 1H), 11.17 (s, 1H), 10.58 (s, 1H), 10.53 (s, 1H), 9.77 (s, 1H), 9.66 (s, 1H), 8.95 (d, J=7.5 Hz, 1H), 8.83-8.85 (m, 1H), 8.26 (dd, J=8.6, 2.3 Hz, 1H), 8.20 (d, J=8.8 Hz, 1H), 8.05 (d, J=8.8 Hz, 1H), 7.97 (d, J=8.7 Hz, 2H), 7.81 (d, J=8.4 Hz, 1H), 7.79 (d, J=8.7 Hz, 2H), 7.57-7.61 (m, 2H), 7.41 (s, 1H), 7.36 (d, J=8.5 Hz, 2H), 6.83 (d, J=8.5 Hz, 2H), 4.91-4.99 (m, 1H), 3.92 (s, 3H), 3.78 (s, 3H), 3.30-3.34 (m, 1H), 3.21-3.25 (m, 1H), 2.10-2.12 ppm (m, 3H).

HRMS (ESI): m/z calculated for C$_{44}$H$_{39}$N$_9$O$_{12}$ [M+H]$^+$: 886.2791; found: 886.2772.

Compound 3

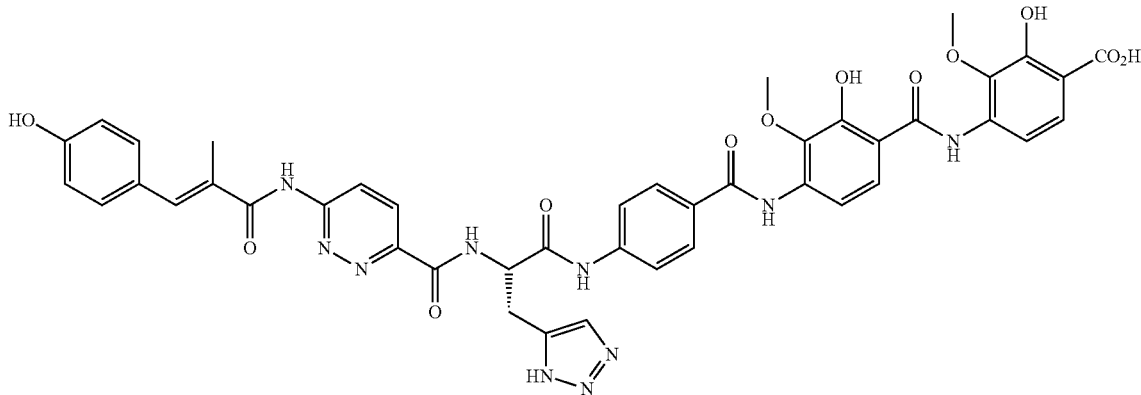

¹H NMR (DMSO-d$_6$, 400 MHz): δ=11.59 (br. s, 1H), 11.54 (s, 1H), 11.31 (s, 1H), 11.19 (s, 1H), 10.57 (s, 1H), 9.84 (br. s, 1H), 9.70 (s, 1H), 9.13 (d, J=8.0 Hz, 1H), 8.49 (d, J=9.3 Hz, 1H), 8.20 (d, J=9.0 Hz, 1H), 8.06 (d, J=8.8 Hz, 1H), 7.98 (d, J=8.8 Hz, 2H), 7.81 (d, J=8.8 Hz, 1H), 7.77 (d, J=8.8 Hz, 2H), 7.58 (t, J=8.3 Hz, 2H), 7.48 (s, 1H), 7.39 (d, J=8.5 Hz, 2H), 6.85 (d, J=8.5 Hz, 2H), 4.99-5.07 (m, 1H), 3.91 (s, 3H), 3.78 (s, 3H), 3.38 (d, J=6.8 Hz, 2H), 2.14 ppm (d, J=1.3 Hz, 3H).

HRMS (ESI): m/z calculated for $C_{43}H_{38}N_{10}O_{12}$ [M+H]⁺: 887.2743; found: 887.2727.

Compound 4

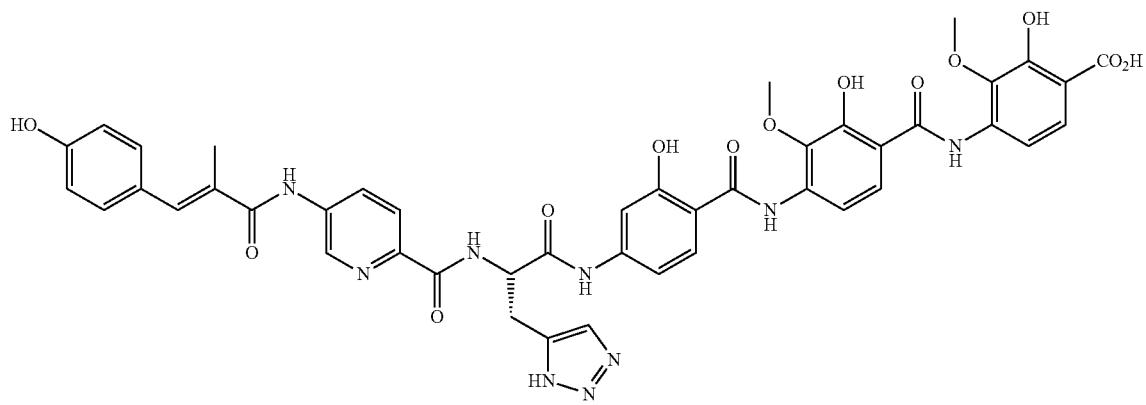

¹H NMR (DMSO-d$_6$, 400 MHz): δ=11.93 (s, 1H), 11.56 (s, 1H), 11.11 (s, 1H), 11.08 (s, 1H), 10.50 (s, 1H), 10.35 (s, 1H), 9.80 (br. s, 1H), 8.99 (d, J=2.5 Hz, 1H), 8.77 (d, J=8.3 Hz, 1H), 8.33 (dd, J=8.5, 2.5 Hz, 1H), 8.16 (d, J=8.8 Hz, 1H), 7.95-8.05 (m, 3H), 7.83 (d, J=9.0 Hz, 1H), 7.56-7.61 (m, 2H), 7.37 (d, J=8.5 Hz, 2H), 7.33 (s, 1H), 7.14 (dd, J=8.7, 1.9 Hz, 1H), 6.85 (d, J=8.5 Hz, 2H), 4.93-5.01 (m, 1H), 3.91 (s, 3H), 3.82 (s, 3H), 3.32 (d, J=6.5 Hz, 2H), 2.12-2.14 ppm (m, 3H).

HRMS (ESI): m/z calculated for $C_{44}H_{39}N_9O_{13}$ [M+H]⁺: 902.2740; found: 902.2737.

Compound 5

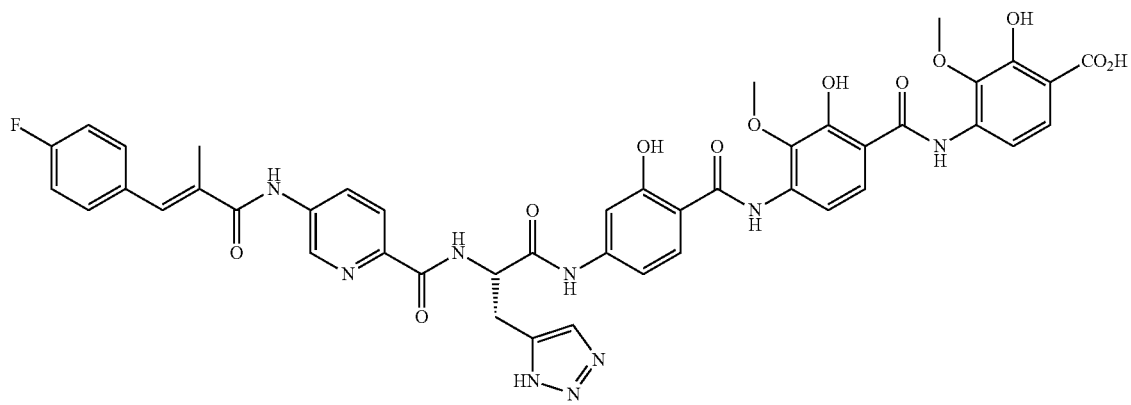

¹H NMR (DMSO-d₆, 500 MHz): $\delta$=11.90-11.94 (m, 1H), 11.55-11.57 (m, 1H), 11.10-11.12 (m, 1H), 11.07-11.08 (m, 1H), 10.48-10.51 (m, 1H), 10.44 (s, 1H), 8.98-9.01 (m, 1H), 8.78 (d, J=8.2 Hz, 1H), 8.34 (dd, J=8.7, 2.4 Hz, 1H), 8.13-8.18 (m, 1H), 7.96-8.05 (m, 3H), 7.83 (d, J=8.9 Hz, 1H), 7.51-7.63 (m, J=9.2 Hz, 5H), 7.40 (s, 1H), 7.30 (s, 2H), 7.14 (dd, J=9.0, 2.0 Hz, 1H), 4.94-5.00 (m, 1H), 3.91 (s, 3H), 3.82 (s, 3H), 3.32 (d, J=6.3 Hz, 2H), 2.13 ppm (d, J=1.2 Hz, 3H).

HRMS (ESI): m/z calculated for $C_{44}H_3FN_9O_{12}$ [M+H]⁺: 904.2697; found: 904.2691.

Compound 6

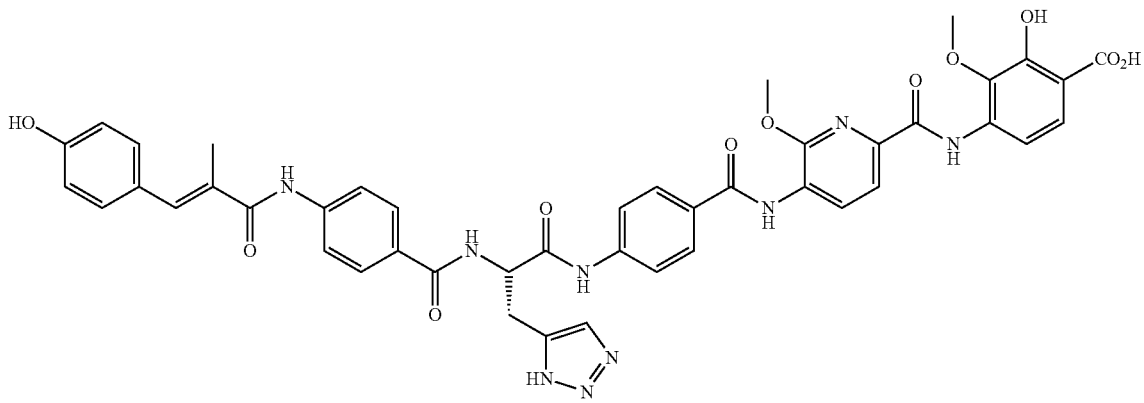

¹H NMR (DMSO-d₆, 500 MHz): $\delta$=11.67 (br. s, 1H), 10.62 (s, 1H), 10.53 (s, 1H), 10.07 (s, 1H), 9.70 (s, 1H), 8.69 (d, J=7.5 Hz, 1H), 8.54 (d, J=7.9 Hz, 1H), 8.07 (d, J=8.9 Hz, 1H), 7.98 (d, J=8.7 Hz, 2H), 7.87 (d, J=8.9 Hz, 3H), 7.83-7.78 (m, 4H), 7.68 (br. s, 1H), 7.64 (d, J=8.9 Hz, 2H), 7.35 (d, J=8.7 Hz, 2H), 7.26 (br. s, 1H), 6.84 (d, J=8.7 Hz, 2H), 4.95-4.88 (m, 1H), 4.16 (s, 3H), 3.98 (s, 3H), 3.34-3.21 (m, 2H), 2.11 ppm (d, J=1.2 Hz, 3H).

HRMS (ESI): m/z calculated for $C_{44}H_{39}N_9O_{11}$ [M+H]⁺: 870.2842; found: 870.2837.

Compound 7

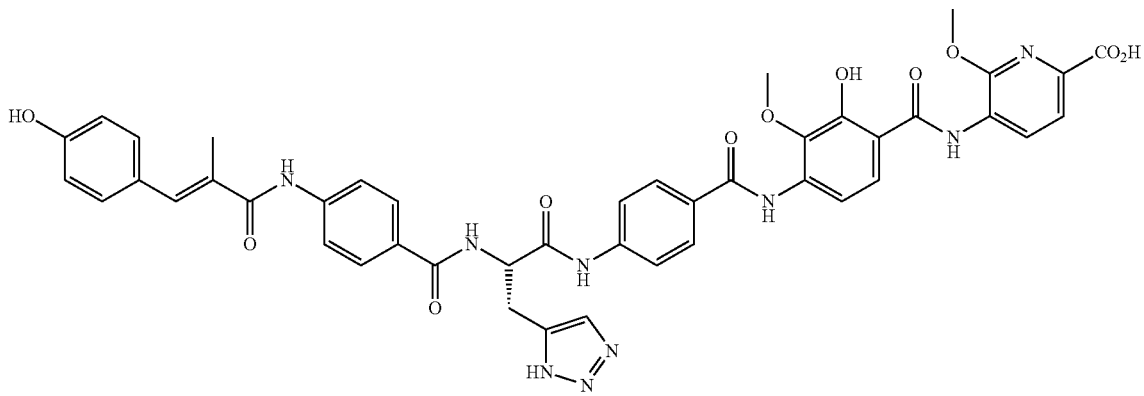

¹H NMR (DMSO-d₆, 500 MHz): δ=11.61 (s, 1H), 11.02 (s, 1H), 10.50 (s, 1H), 10.07 (s, 1H), 9.75 (s, 1H), 9.65 (1H), 8.78 (d, J=8.1 Hz, 1H), 8.72-8.65 (m, 1H), 7.97 (d, J=8.9 Hz, 2H), 7.89-7.84 (m, 2H), 7.83-7.76 (m, 6H), 7.64 (br. s, 1H), 7.60 (d, J=8.9 Hz, 1H), 7.35 (d, J=8.7 Hz, 2H), 7.26 (br. s, 1H), 6.84 (d, J=8.7 Hz, 2H), 4.95-4.88 (m, 1H), 4.07 (s, 3H), 3.78 (s, 3H), 3.27-3.20 (m 2H), 2.11 ppm (d, J=1.2 Hz, 3H).
HRMS (ESI): m/z calculated for $C_{44}H_{39}N_9O_{11}$ [M+H]⁺: 870.2842; found: 870.2845.
Compound 8
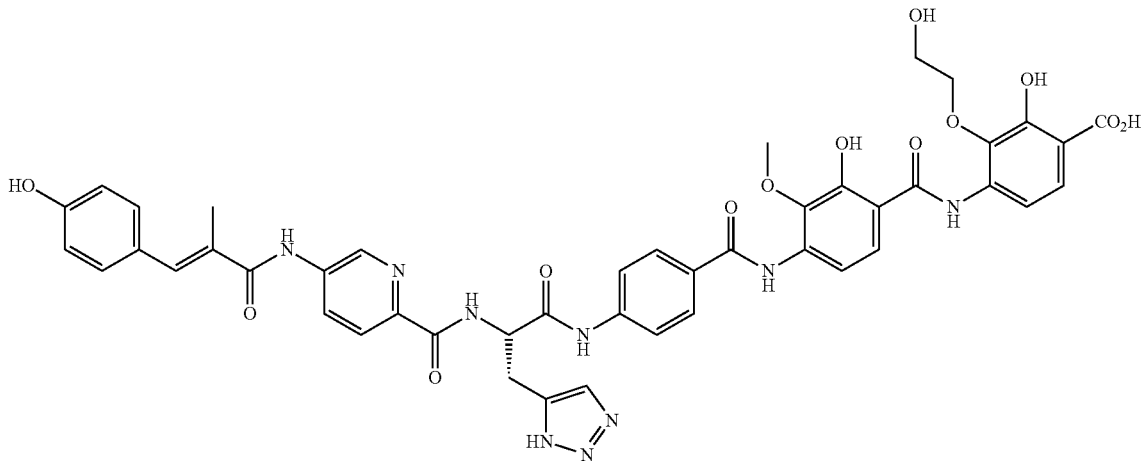
¹H NMR (DMSO-d₆, 500 MHz): δ=11.76 (s, 1H), 10.64 (s, 1H), 10.56 (s, 1H), 10.35 (s, 1H), 9.80 (br. s, 1H), 9.60 (s, 1H), 8.98 (d, J=2.3 Hz, 1H), 8.78 (d, J=8.2 Hz, 1H), 8.34 (dd, J=8.6, 2.4 Hz, 1H), 8.01 (d, J=8.5 Hz, 1H), 7.99-7.94 (m, 3H), 7.99-7.94 (m, 3H), 7.81-7.73 (m, 4H), 7.65-7.57 (m, 3H), 7.37 (d, J=8.5 Hz, 2H), 7.33 (br. s, 1H), 6.85 (d, J=8.5 Hz, 2H), 5.02-4.95 (m, 1H), 4.17 (t, J=5.2 Hz, 2H), 3.74 (t, J=5.2 Hz, 2H), 3.34 (d, J=6.0 Hz, 2H), 2.13 ppm (s, 3H).
HRMS (ESI): m/z calculated for $C_{45}H_{41}N_9O_{13}$ [M+H]⁺: 916.2897; found: 916.2897.
Compound 9
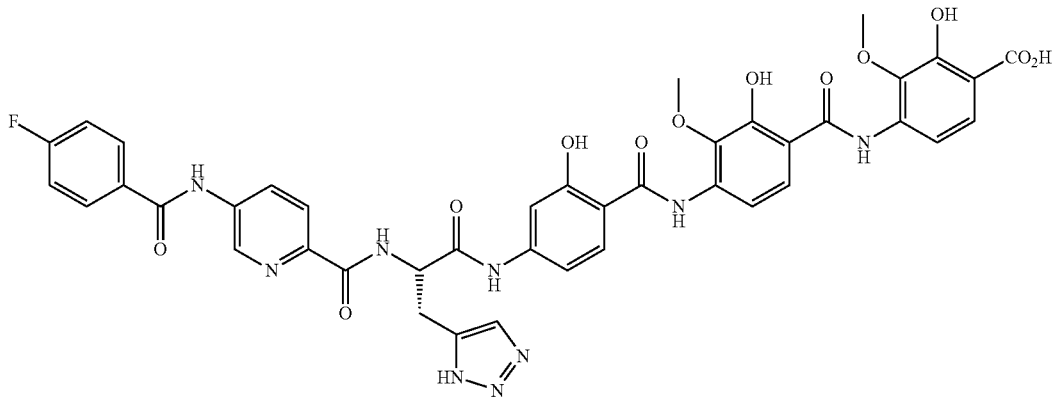

¹H NMR (DMSO-d₆, 700 MHz): δ=11.94 (s, 1H), 11.57 (s, 1H), 11.12 (s, 1H), 11.08 (s, 1H), 10.76 (s, 1H), 10.51 (s, 1H), 9.05 (d, J=2.3 Hz, 1H), 8.80 (d, J=7.9 Hz, 1H), 8.40 (dd, J=8.5, 2.3 Hz, 1H), 8.16 (d, J=8.8 Hz, 1H), 8.07-8.11 (m, 2H), 8.05 (d, J=8.8 Hz, 1H), 8.03 (d, J=9.0 Hz, 1H), 7.98 (d, J=8.8 Hz, 1H), 7.83 (d, J=8.5 Hz, 1H), 7.58-7.61 (m, 2H), 7.40-7.44 (m, 2H), 7.13 (dd, J=8.8, 1.7 Hz, 1H), 4.95-5.00 (m, 1H), 3.91 (s, 3H), 3.82 (s, 3H), 3.32 ppm (d, J=6.4 Hz, 2H)

HRMS (ESI): m/z calculated for $C_{41}H_{34}FN_9O_{12}$ [M+H]⁺: 864.2384; found 864.2379.

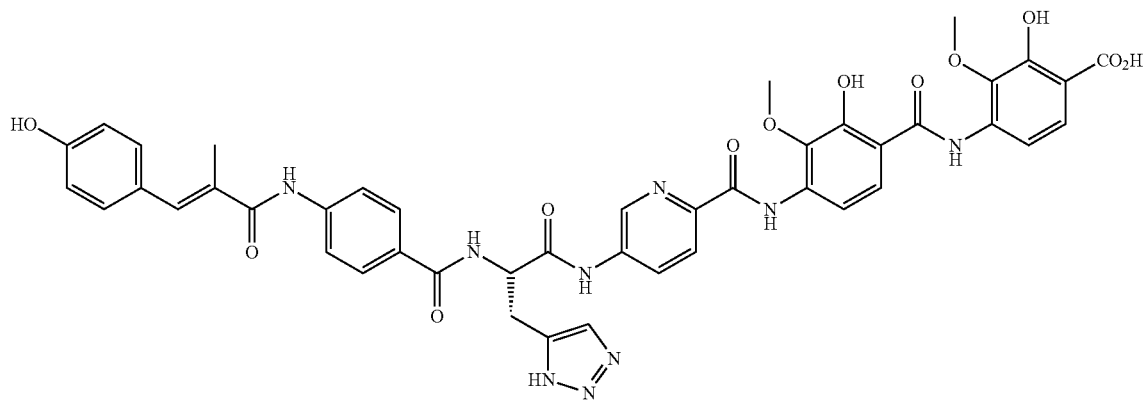

Compound 10

¹H NMR (DMSO-d₆, 700 MHz): δ=11.72 (s, 1H), 11.60 (br. s, 1H), 11.14 (s, 1H), 10.84 (s, 1H), 10.49 (s, 1H), 10.10 (s, 1H), 9.78 (br. s, 1H), 8.98 (d, J=2.0 Hz, 1H), 8.78 (d, J=7.45 Hz, 1H), 8.35 (dd, J=8.6, 2.1 Hz, 1H), 8.21 (d, J=8.6 Hz, 1H), 8.12 (d, J=9.3 Hz, 1H), 7.89-7.87 (m, 3H), 7.82 (d, J=8.9 Hz, 2H), 7.71 (br. s, 1H), 7.60 (d, J=8.9 Hz, 1H), 7.36 (d, J=8.9 Hz, 2H), 7.27 (s, 1H), 6.85 (d, J=8.4 Hz, 2H), 4.95-4.92 (m, 1H), 3.92 (s, 3H), 3.88 (s, 3H), 3.34-3.31 (m, 1H), 3.28-3.26 (m, 1H), 2.12 (s, 3H).

HRMS (ESI): m/z calculated for $C_{44}H_{39}N_9O_{12}$ [M+H]⁺: 886.27; found: 886.28.

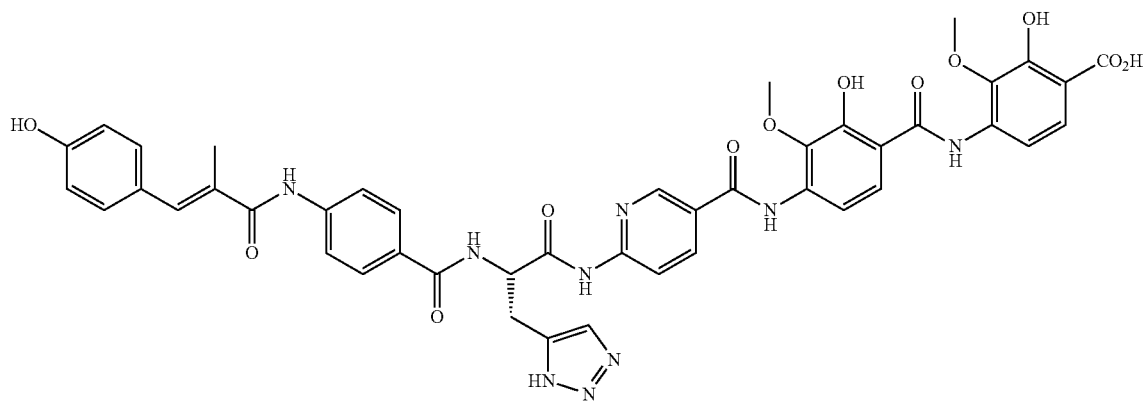

Compound 11

¹H NMR (DMSO-d$_6$, 700 MHz): δ=11.55 (s, 1H), 11.18 (s, 1H), 11.00 (br.s, 1H), 10.10 (s, 1H), 10.00 (d, J=8.9 Hz, 1H), 9.77 (d, J=8.9 Hz, 1H), 8.92 (d, J=2.0 Hz, 1H), 8.69 (d, J=6.6 Hz, 1H), 8.35 (dd, J=8.9, 2.1 Hz, 1H), 8.21 (d, J=8.7 Hz, 1H), 8.05 (d, J=9.2 Hz, 1H), 7.90 (d, J=7.7 Hz, 2H), 7.86 (d, J=8.6 Hz, 2H), 7.83 (dd, J=9.1, 2.1 Hz, 2H), 7.76-7.74 (m, 2H), 7.64 (d, J=9.1 Hz, 1H), 7.69 (d, J=8.7 Hz, 1H), 7.54 (d, J=8.9 Hz, 1H), 7.42 (t, J=7.3 Hz, 2H), 7.36-7.32 (m, 3H), 6.85 (d, J=8.4 Hz, 2H), 5.04-4.99 (m, 1H), 4.29-4.25 (m, 1H), 4.24-4.20 (m, 1H), 3.92 (s, 3H), 3.78 (s, 3H), 2.12 (s, 3H).

HRMS (ESI): m/z calculated for C$_{44}$H$_{39}$N$_9$O$_{12}$ [M+H]$^+$: 886.27; found: 886.28.

Compound 12

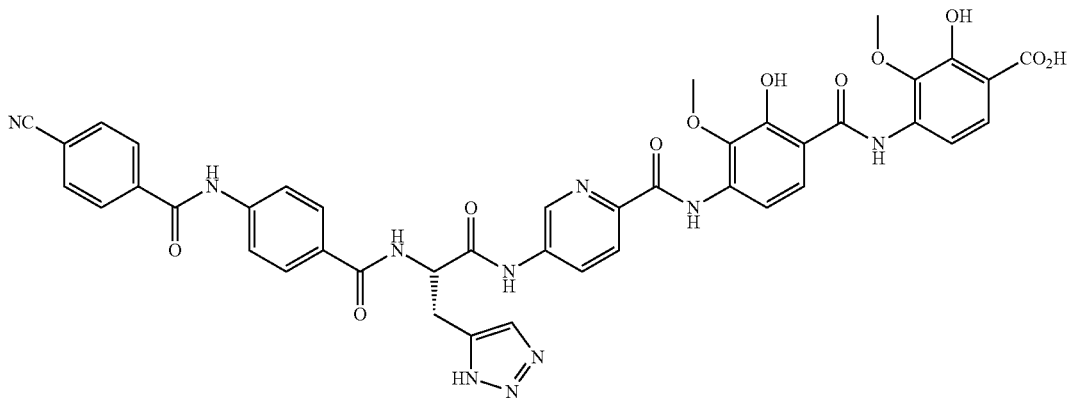

¹H NMR (DMSO-d$_6$, 700 MHz): δ=11.72 (s, 1H), 11.13 (s, 1H), 10.85 (s, 1H), 10.70 (s, 1H), 10.50 (s, 1H), 8.98 (d, J=2.4 Hz, 1H), 8.84 (d, J=6.8 Hz, 1H), 8.34 (dd, J=8.6, 2.3 Hz, 1H), 8.21 (d, J=8.5 Hz, 1H), 8.13 (d, J=8.5 Hz, 2H), 8.12 (d, J=8.9 Hz, 1H), 8.05 (d, J=8.5 Hz, 2H), 8.03 (d, J=8.8 Hz, 1H), 7.94-7.88 (m, 5H), 7.59 (d, J=8.8 Hz, 1H), 4.96-4.93 (m, 1H), 3.92 (s, 3H), 3.88 (s, 3H), 3.35-3.33 (m, 1H), 3.29-3.27 (m, 1H).

HRMS (ESI): m/z calculated for C$_{42}$H$_{34}$N$_{10}$O$_{11}$ [M+H]$^+$: 855.24; found: 855.25.

Compound 13

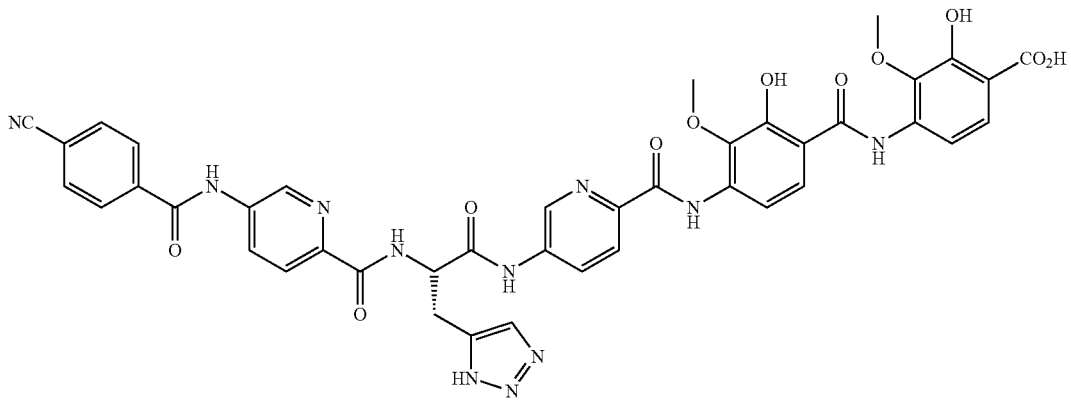

¹H NMR (DMSO-d₆, 700 MHz): $\delta$=11.72 (s, 1H), 11.62 (br. s, 1H), 11.13 (s, 1H), 10.98 (s, 1H), 10.87 (s, 1H), 10.49 (s, 1H), 9.05 (d, J=2.2 Hz, 1H), 8.96 (d, J=2.1 Hz, 1H), 8.89 (d, J=7.9 Hz, 1H), 8.42 (dd, J=8.5, 2.4 Hz, 1H), 8.30 (dd, J=8.4, 2.3 Hz, 1H), 8.22 (d, J=8.5 Hz, 1H), 8.16 (d, J=8.5, 2H), 8.11 (d, J=8.9 Hz, 1H), 8.08 (d, J=8.2 Hz, 2H), 8.03 (d, J=8.9 Hz, 1H), 7.88 (d, J=8.9 Hz, 1H), 7.59 (d, J=8.9 Hz, 1H), 5.04-5.00 (m, 1H), 3.92 (s, 3H), 3.88 (s, 3H), 3.35-3.33 (m, 1H), 3.29-3.27 (m, 1H).

HRMS (ESI): m/z calculated for $C_{41}H_{33}N_{11}O_{11}$ [M+H]⁺: 856.24; found: 855.24.

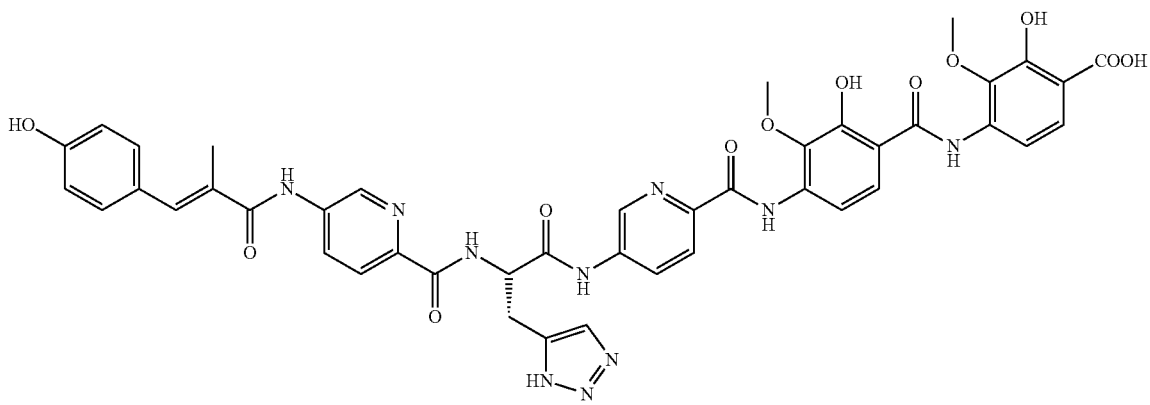

Compound 14

¹H NMR (DMSO-d₆, 700 MHz): $\delta$=11.72 (s, 1H), 11.59 (br. s, 1H), 11.14 (s, 1H), 10.87 (s, 1H), 10.49 (s, 1H), 10.37 (s, 1H), 9.81 (br. s, 1H), 8.99 (d, J=2.6 Hz, 1H), 8.96 (d, J=2.4 Hz, 1H), 8.65 (d, J=7.8 Hz, 1H), 8.34 (dd, J=8.6, 2.4 Hz, 1H), 8.30 (dd, J=8.7, 2.4 Hz, 1H), 8.22 (d, J=8.5 Hz, 1H), 8.11 (d, J=8.6 Hz, 1H), 8.04-8.01 (t, J=8.7 Hz, 2H), 7.88 (d, J=8.8 Hz, 1H), 7.59 (d, J=8.7 Hz, 1H), 7.38 (d, J=7.4 Hz, 2H), 7.34 (s, 1H), 6.86 (d, J=8.5 Hz, 2H), 5.02-4.99 (m, 1H), 3.92 (s, 3H), 3.88 (s, 3H), 3.37-3.31 (m, 2H), 2.14 (s, 3H).

HRMS (ESI): m/z calculated for $C_{43}H_{38}N_{10}O_{12}$ [M+H]⁺: 887.27; found: 887.27.

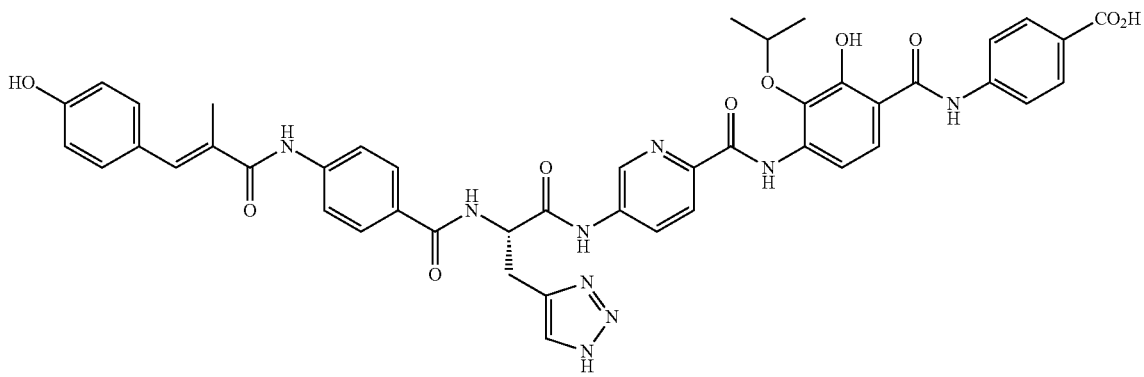

Compound 15

¹H NMR (DMSO-d₆, 700 MHz): δ=12.43-12.50 (s, 1H), 10.86-10.96 (s, 1H), 10.74 (br. s., 1H), 10.61-10.69 (i, 1H), 10.10 (br. s., 1H), 9.82 (br. s., 1H), 8.96-9.04 (m, 1H), 8.73-8.85 (m, 1H), 8.27-8.37 (m, 1H), 8.15-8.23 (m, 1H), 8.05-8.14 (m, 1H), 7.96 (d, J=7.9 Hz, 3H), 7.87 (br. s., 4H), 7.82 (d, J=7.9 Hz, 2H), 7.61-7.73 (m, 1H), 7.35 (d, J=7.7 Hz, 2H), 7.27 (br. s., 4H), 6.84 (d, J=7.9 Hz, 2H), 6.56 (br. s., 2H), 6.51-6.61 (m, 2H), 4.87-4.96 (m, 1H), 4.62-4.73 (m, 1H), 2.11 (br. s., 3H), 1.32-1.37 ppm (m, 6H).
HRMS (ESI): m/z calculated for $C_{45}H_{41}N_9O_{10}$ [M+H]⁺: 868.3049; found: 868.3075.
Compound 16
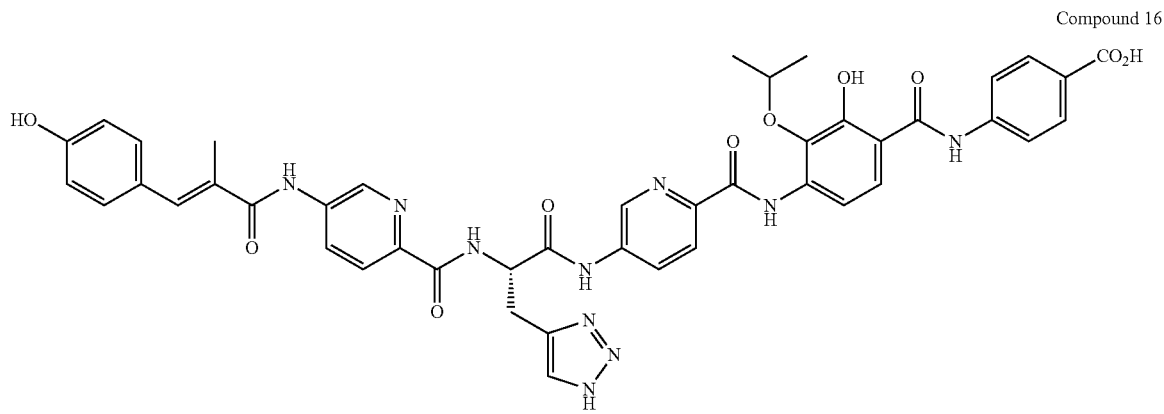 [SMILES: C/C(=C\c1ccc(O)cc1)C(=O)Nc1ccc(C(=O)N[C@@H](Cc2c[nH]nn2)C(=O)Nc2ccc(C(=O)Nc3ccc(C(=O)Nc4ccc(C(=O)O)cc4)c(O)c3OC(C)C)nc2)nc1]
¹H NMR (DMSO-d₆, 400 MHz): δ=12.46 (s, 1H), 10.85 (s, 1H), 10.75 (s, 1H), 10.62 (s, 1H), 10.38 (s, 1H), 9.78-9.90 (m, 1H), 8.99 (d, J=3.0 Hz, 2H), 8.87 (d, J=8.0 Hz, 1H), 8.24-8.39 (m, 2H), 8.07-8.23 (m, 2H), 7.95-8.05 (m, 3H), 7.83-7.94 (m, 3H), 7.50-7.76 (m, 1H), 7.28-7.45 (m, 3H), 6.85 (d, J=8.5 Hz, 2H), 5.00 (d, J=7.3 Hz, 1H), 4.54-4.78 (m, 1H), 3.37 (d, J=6.0 Hz, 2H), 2.13 (s, 3H), 1.35 ppm (dd, J=5.8, 4.5 Hz, 6H).
HRMS (ESI): m/z calculated for $C_{44}H_{40}N_{10}O_{10}$ [M+H]⁺: 869.3002; found: 869.2995.
Compound 17
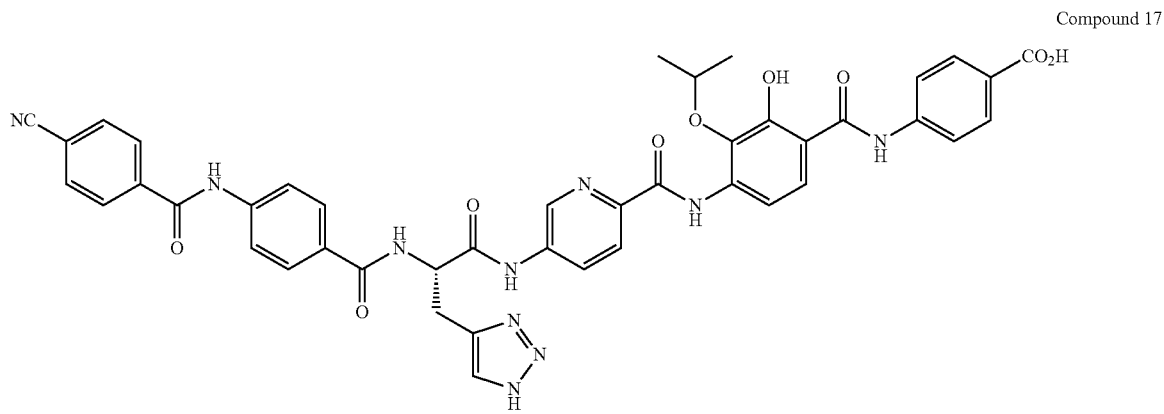 [SMILES: CC(C)Oc1c(NC(=O)c2ccc(NC(=O)[C@H](Cc3c[nH]nn3)NC(=O)c3ccc(NC(=O)c4ccc(C#N)cc4)cc3)cn2)ccc(C(=O)Nc2ccc(C(=O)O)cc2)c1O]

¹H NMR (DMSO-d₆, 400 MHz): δ=12.47 (s, 1H), 10.87 (s, 1H), 10.75 (s, 1H), 10.73 (s, 1H), 10.63 (s, 1H), 9.00 (d, J=2.0 Hz, 1H), 8.85 (d, J=7.5 Hz, 1H), 8.19 (d, J=8.5 Hz, 1H), 8.12 (t, J=8.2 Hz, 2H), 8.02-8.07 (m, 2H), 7.82-8.00 (m, 7H), 7.72 (br. s., 1H), 4.92 (d, J=6.8 Hz, 1H), 4.56-4.76 (m, 1H), 3.20-3.40 (m, 2H), 1.34 ppm (dd, J=6.0, 4.0 Hz, 6H).
HRMS (ESI): m/z calculated for $C_{43}H_{36}N_{10}O_9$ [M+H]⁺: 837.2739; found: 837.2739.
Compound 18
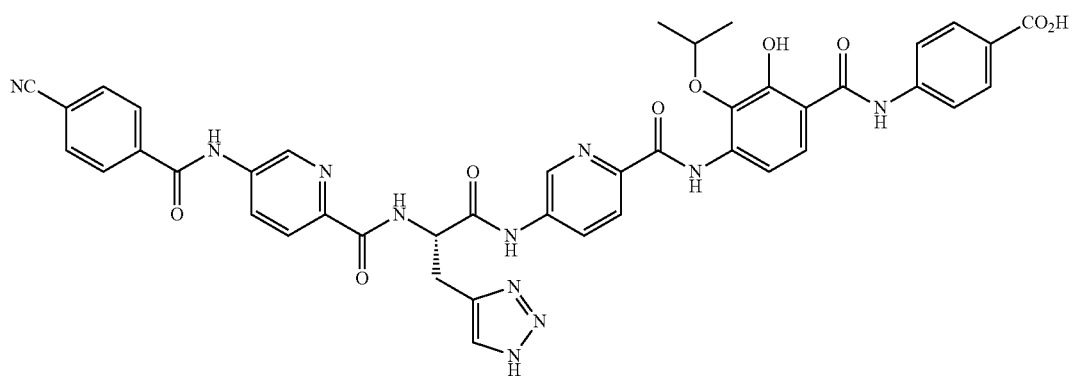
¹H NMR (DMSO-d₆, 400 MHz): δ=9.05 (d, J=2.3 Hz, 1H), 8.99 (d, J=2.3 Hz, 1H), 8.86-8.94 (m, 1H), 8.38-8.47 (m, 1H), 8.24-8.32 (m, 1H), 8.14-8.22 (m, 3H), 8.04-8.14 (m, 4H), 7.90-8.01 (m, 3H), 7.86 (d, J=8.8 Hz, 2H), 4.94-5.07 (m, 1H), 4.67 (s, 1H), 1.34 ppm (dd, J=5.8, 4.3 Hz, 6H).
HRMS (ESI): m/z calculated for $C_{42}H_{35}N_{10}O_9$ [M+H]⁺: 838.2686; found: 838.2699.
Compound 19
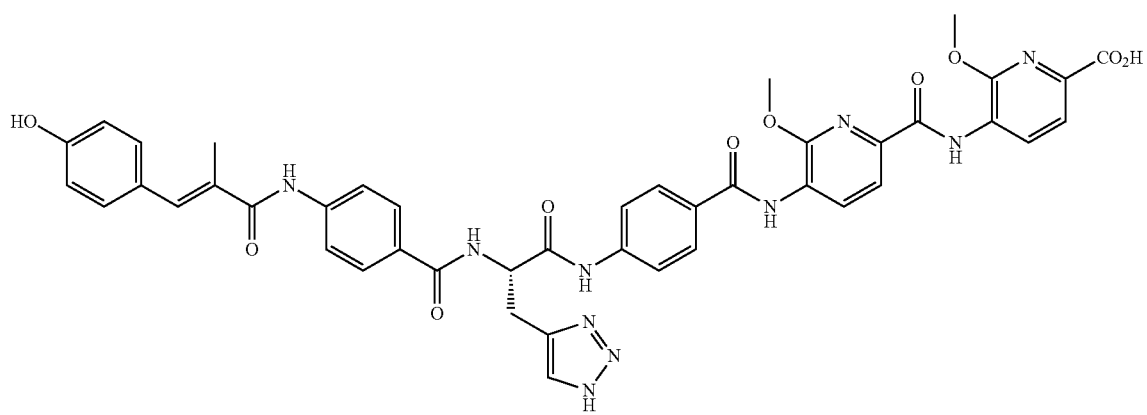

¹H NMR (400 MHz, DMSO-d₆): $\delta$=14.66 (br. s., 1H), 12.66-13.13 (m, 1H), 10.55 (br. s., 1H), 10.44 (s, 1H), 10.09 (s, 1H), 9.79 (s, 1H), 9.71 (s, 1H), 8.66-8.82 (m, 2H), 8.55 (d, J=7.8 Hz, 1H), 7.98 (d, J=8.8 Hz, 2H), 7.75-7.91 (m, 8H), 7.65 (br. s., 1H), 7.35 (d, J=8.5 Hz, 2H), 7.27 (s, 1H), 6.84 (d, J=8.5 Hz, 2H), 4.91 (d, J=5.8 Hz, 1H), 4.15 (s, 3H), 4.09 (s, 3H), 3.30-3.36 (m, 2H), 2.12 ppm (s, 3H).
HRMS (ESI): m/z calculated for $C_{43}H_{38}N_{10}O_{10}$ $[M+H]^+$ 855.2845, found 855.2823.
Compound 20
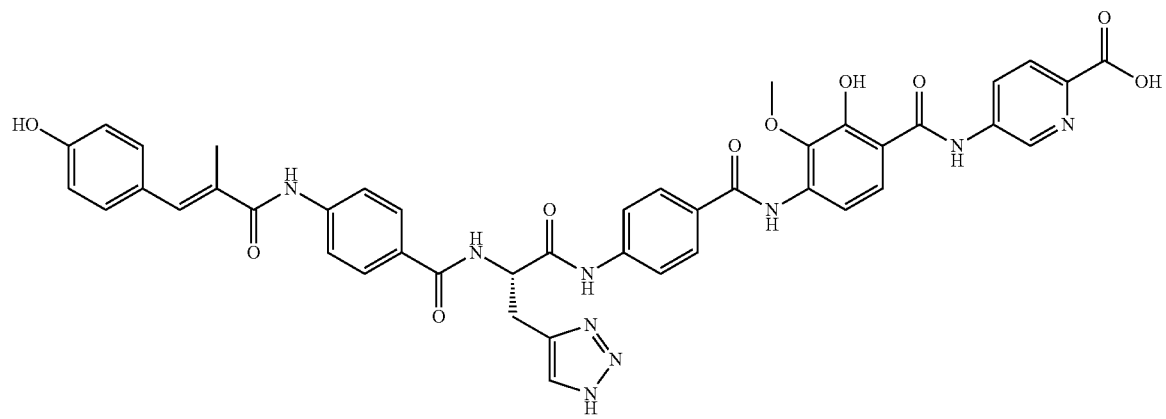
¹H NMR (500 MHz, DMSO-d₆): $\delta$=11.99 (br. s, 1H), 10.79 (s, 1H), 10.52 (s, 1H), 10.08 (s, 1H), 9.56 (s, 1H), 9.01 (s, 1H), 8.70 (d, J=7.5 Hz, 1H), 8.35-8.38 (m, 1H), 8.11 (d, J=8.5 Hz, 1H), 7.97 (d, J=7.9 Hz, 2H), 7.78-7.89 (m, 7H), 7.65-7.72 (m, 2H), 7.36 (d, J=7.7 Hz, 2H), 7.27 (s, 1H), 6.86 (s, 1H), 6.84 (s, 1H), 4.92 (dd, J=14.6, 7.9 Hz, 1H), 3.87 (s, 3H), 3.18-3.41 (m, 2H), 2.55 (s, 1H), 2.12 ppm (d, J=1.2 Hz, 3H).
HRMS (ESI): m/z calculated for $C_{43}H_{37}N_9O_{10}$ $[M+H]^+$ 840.2736, found. 840.2732.
Compound 21
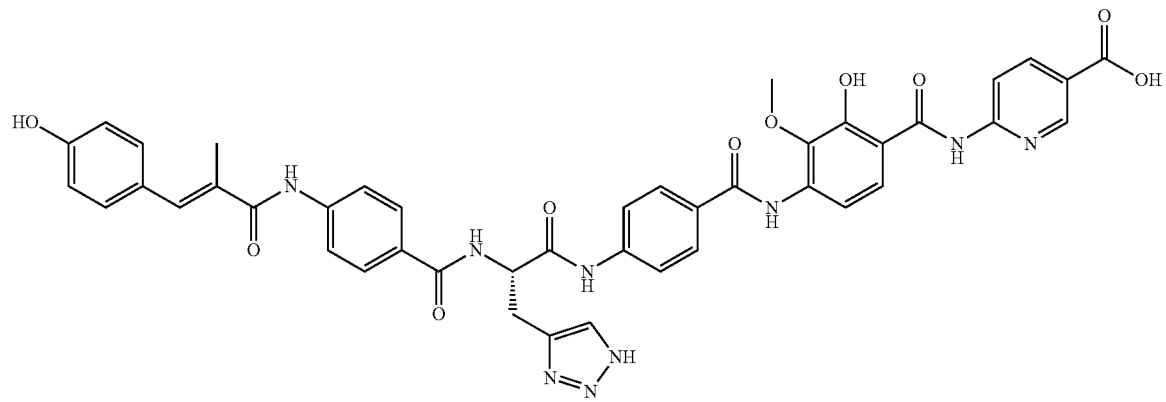

$^1$H NMR (500 MHz, DMSO-d$_6$): δ=11.73 (br. s, 1H), 11.23 (br. s, 1H), 10.51 (s, 1H), 10.08 (s, 1H), 9.62 (s, 1H), 8.89 (t, J=1.5 Hz, 1H), 8.69 (d, J=7.6 Hz, 1H), 8.35 (d, J=1.4 Hz, 2H), 7.97 (d, J=8.9 Hz, 2H), 7.78-7.90 (m 7H), 7.69 (s, 1H), 7.63 (d, J=8.9 Hz, 1H), 7.36 (d, J=7.7 Hz, 2H), 7.27 (s, 1H), 6.85 (s, 1H), 6.84 (s, 1H), 4.87-4.96 (m, 1H), 3.81 (s, 3H), 3.21-3.35 (m, 2H), 2.55 (s, 1H), 2.12 ppm (d, J=1.2 Hz, 3H).
HRMS (ESI): m/z ber. fir C$_{43}$H$_{37}$N$_9$O$_{10}$ [M+H]$^+$ 840.2736, gef. 840.2733.
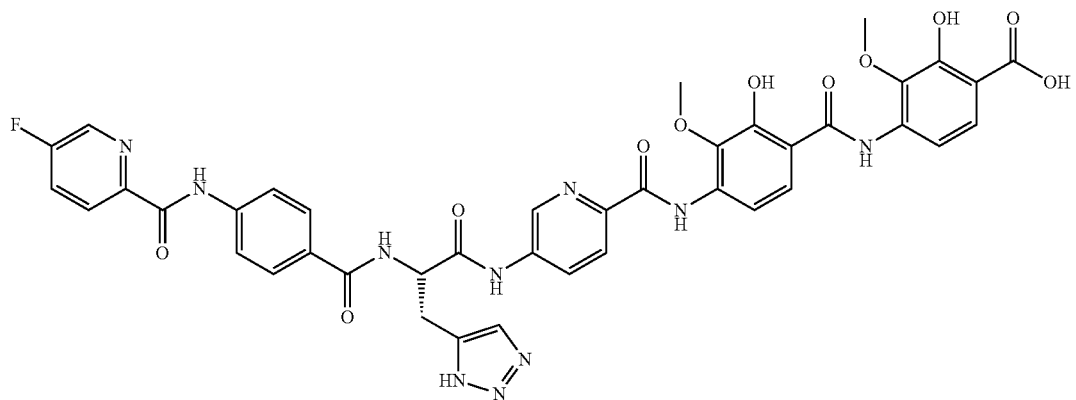
Compound 22
$^1$H NMR (700 MHz, DMSO-d$_6$): □=11.79 (s, 1H), 10.86 (s, 1H), 10.84 (s, 1H), 10.49 (s, 1H), 8.97 (d, J=2.4 Hz, 1H), 8.76 (d, J=3.1 Hz, 1H), 8.35 (dd, J=8.6, 2.3 Hz, 1H), 8.26 (dd, J=8.6, 4.6 Hz, 1H), 8.21 (d, J=8.5 Hz, 1H), 8.09 (d, J=8.4, 1H), 8.02 (d, J=8.9 Hz, 2H), 8.01 (td, J=8.6, 2.35 Hz, 1H), 7.90 (d, J=8.5 Hz, 2H), 7.86 (d, J=8.8 Hz, 1H), 7.55-7.88 (m, 5H), 4.94-4.92 ppm (m, 1H).
HRMS (ESI): m/z calculated for C$_{42}$H$_{34}$N$_{10}$O$_{11}$ [M+H]$^+$: 849.23; found: 849.24.
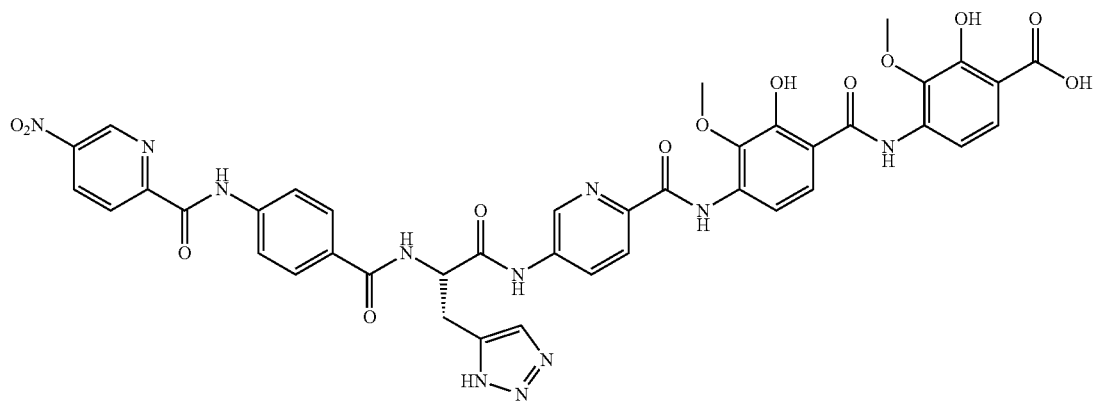
Compound 23

$^1$H NMR (700 MHz, DMSO-d$_6$): □=11.17 (s, 1H), 10.89 (s, 1H), 9.48 (s, 1H), 8.99 (s, 1H), 8.87 (dd, J=8.5, 2.4 Hz, 2H), 8.43 (d, J=8.6 Hz, 1H), 8.36 (d, J=7.2 Hz, 1H), 8.23 (d, J=8.6, 1H), 8.13 (d, J=8.5 Hz, 1H), 8.08 (d, J=8.4 Hz, 2H), 7.95 (d, J=8.4 Hz, 2H), 7.90 (s, 1H), 6.58 (s, 1H), 4.98-4.96 (m, 1H), 3.92 (s, 3H), 3.89 ppm (s, 3H).

HRMS (ESI): m/z calculated for C$_{42}$H$_{34}$N$_{10}$O$_{11}$ [M+H]$^+$: 876.23; found: 876.23.

Compound 24

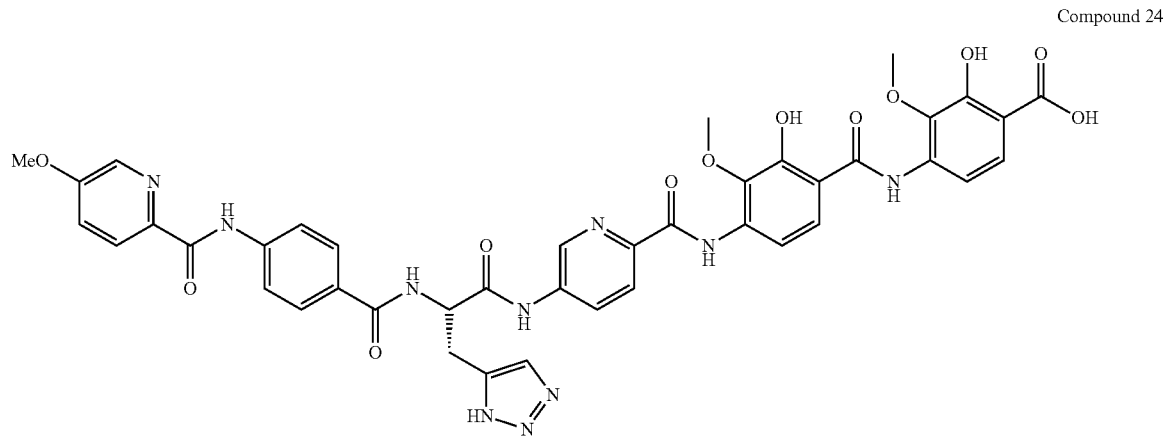

$^1$H NMR (700 MHz, DMSO-d$_6$): □=11.76 (s, 1H), 10.85 (s, 1H), 10.75 (s, 1H), 10.70 (s, 1H), 10.49 (s, 1H), 8.98 (d, J=2.4 Hz, 1H), 8.84 (d, J=6.8 Hz, 1H), 8.34 (dd, J=8.6, 2.3 Hz, 1H), 8.20 (d, J=8.6 Hz, 1H), 8.15 (d, J=8.5 Hz, 1H), 8.08 (d, J=5.6 Hz, 1H), 8.07 (d, J=5.6 Hz, 1H), 8.01 (d, J=8.8 Hz, 2H), 7.89 (d, J=8.8 Hz, 2H), 7.64 (dd, 8.4, 2.5 Hz, 1H) 7.54 (s, 1H), 4.93-4.89 (m, 1H), 3.92 (s, 3H), 3.88 (s, 3H), 3.87 (s, 3H).

HRMS (ESI): m/z calculated for C$_{42}$H$_{34}$N$_{10}$O$_{11}$ [M+H]$^+$: 861.25; found: 861.26.

Test for Biological Activity
Strains:
*E. coli* DSM 1116; *E. coli* BW25113; *S. typhimurium* TA100; *Bacillus subtilis* DSM10; *M. phlei* DSM750 and *Micrococcus luteus* DSM1790

Biological Testing:
The tests were performed using the micro dilution method.

Microdilution Assay:
The determination of MIC values was performed according to the ninth edition of the Approved Standard M07-A9 (CLSI. Methods for Dilution Antimicrobial Susceptibility Tests for Bacteria That Grow Aerobically; Approved Standard-Ninth Edition. CLSI document M07-A9. Wayne, Pa.: Clinical and Laboratory Standards Institute; 2012.)

The test was carried out for the six different bacterial strains 20 µL of cryo stock of each strain were inoculated in 20 mL of LB media (Lysogeny broth: 10 g/L peptone, 5 g/L yeast extract, 5 g/L NaCl) followed by incubation over night at 37° C., 200 rpm. The test inoculum was adjusted by the 0.5 McFarland Standard (OD625 from 0.08 to 0.1). Within 15 min of preparation, the adjusted inoculum suspension was diluted in MHBII media (BBL™ Mueller-Hinton Broth II, Becton, Dickinson and Company, New Jersey/USA) so that each well contained approximately 5×105 CFU/mL in a final volume of 100 µL. 95 µL of the inoculum were applied per well and 5 µL of the (diluted) antibiotic substance were added.

Previously the dry antibiotic compounds were dissolved in DMSO (100%) with a concentration of 2560 µg/mL and the resulting stock solutions were further diluted in DMSO (100%). 5 µL of each antibiotic dilution were applied to the microdilution tray to reach final concentrations of 64 µg/mL to 0.008 µg/mL. One row of each well plate was left as a growth control without antibiotic substances and another row of the microdilution tray was used as sterility control (only MHB II-media). The antimicrobial effect of the solvent (DMSO) was tested by adding 5 µL DMSO to several wells without antibiotics.

Purity check and cell titer control were performed according to International Standard M07-A9 on Mueller-Hinton II Agar (Mueller Hinton II Broth, 15 g/L agar-agar).

Both microdilution trays and agar plates were incubated at 37° C. for 20 h and subsequently analyzed visually. The results are summarized in table 1.

In another approach the albicidin derivatives were provided in a cyclodextrin formulation prepared as follows: 3 g of 2-Hydroxypropyl-ß-cyclodextrin (AppliChem, Darmstadt) were dissolved to a total volume of 10 ml in ddH2O to obtain a solution of 30% cyclodextrin. 12.5 µL of a 3.2 mg/ml stock solution of compound I in 100% DMSO were added to 237.5 µl 30% stock solution of cyclodextrin to give an concentration of 0.16 mg/ml compound 1 in 28.5% cyclodextrin and 5% DMSO. The formulation was mixed by vigorous vortexing for 5 min. Subsequent two-fold dilution series of compound I was prepared in 28.5% cyclodextrin and 5% DMSO and was immediately tested in microdilution assay (according to CLSI standard M07-A9) with following results: Formulated Compound 1 against *E coli* gave an MIC of <10 µM.

TABLE 1

Antibacterial activity of compounds according to the solutionagainst selected strains

| MIC [µg/µL] | E. coli DSM1116 | E. coli BW25113 | B. subtilis DSM10 | M. luteus DSM1790 | M. phlei DSM750 | S. typhimurium TA100 |
|---|---|---|---|---|---|---|
| Albicidin | 0.063 | 0.063 | 0.25 | 1.0 | 2.0 | 0.063 |
| Compound 1 | 0.016 | 0.016 | 0.25 | 0.5 | 2.0 | 0.016 |
| Compound 2 | 0.031 | 0.016 | 0.5 | 2.0 | 2.0 | 0.016 |
| Compound 3 | 0.031 | 0.031 | 1.0 | 4.0 | 2.0 | 0.031 |
| Compound 4 | 0.031 | 0.031 | 1.0 | 2.0 | 2.0 | 0.016 |
| Compound 5 | 0.016 | 0.063 | 0.25 | 2.0 | 2.0 | 0.016 |
| Compound 6 | 0.016 | 0.016 | 0.25 | 0.125 | 1.0 | 0.031 |
| Compound 7 | 0.25 | 0.5 | 2.0 | >8 | 8.0 | 0.25 |
| Compound 8 | 0.063 | 0.125 | 2.0 | 2.0 | 2.0 | 0.031 |
| Compound 9 | 0.063 | 0.125 | 1.0 | >8.0 | 1.0 | 0.31 |
| Compound 10 | ≤0.016 | ≤0.016 | 0.063 | 0.031 | 0.25 | ≤0.016 |
| Compound 11 | 1.0 | 0.5 | 0.5 | 4.0 | 8.0 | 4.0 |
| Compound 12 | 0.031 | 0.031 | 0.25 | 0.125 | 8.0 | ≤0.016 |
| Compound 13 | 0.031 | 0.031 | 0.125 | 0.063 | 1.0 | 4.0 |
| Compound 14 | ≤0.016 | 0.063 | 0.125 | 0.125 | 4.0 | ≤0.016 |
| Compound 15 | 0.031 | 0.031 | ≤0.016 | 0.063 | 0.25 | ≤0.016 |
| Compound 16 | 0.031 | ≤0.016 | ≤0.016 | ≤0.016 | 0.031 | ≤0.016 |
| Compound 17 | 0.031 | 0.031 | 0.031 | 0.125 | 0.5 | ≤0.016 |
| Compound 18 | 0.031 | ≤0.016 | ≤0.016 | ≤0.016 | 0.031 | ≤0.016 |
| Compound 19 | 0.5 | 1.0 | 4.0 | 2.0 | 8.0 | 0.5 |
| Compound 20 | >8.0 | >8.0 | ≥8.0 | ≥8.0 | ≥8.0 | 0.125 |
| Compound 21 | 0.125 | 0.125 | 4.0 | 4.0 | 4.0 | 0.016 |

The invention claimed is:

1. A compound having a molecular structure as defined by a general formula (1)

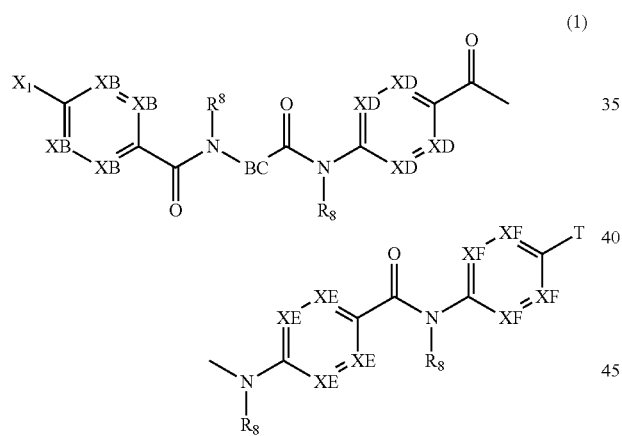

a) with XB being independently from each other N or $CR^{14}$;
b) with XD being independently from each other N or $CR^{13}$;
c) with XE being independently from each other N or $CR^{11}$;
d) with XF being independently from each other N or $CR^{10}$;
wherein at least one of XB, XD, XE and XF must be N;
with each $R^{10}$, $R^{11}$, $R^{13}$ and $R^{14}$ being selected independently from —H, —OH, —F, —Cl, —Br, —I, —CCH, —CN, —$N_3$, —$OC_1$-$C_6$ alkyl that is optionally substituted with OH or F, —$OCF_3$, —$NH_2$, —$NHCH_3$, —$N(CH_3)_2$, —$C_1$-$C_6$ alkyl, —$(CH_2)$m-$OR_a$, —$CHCH_2$, —$CH_2OH$, —$SO_2NH_2$, —$SO_2N(CH_3)_2$, —$SO_2NHCH_3$, —$CF_3$, —$NO_2$, —O—$PO_3H_2$, —O—$PO_3R_aH$, or —O—$PO_3R_{a2}$, with $R_a$ being
hydrogen,
with m being selected from 0, 1 or 2,
e) with BC being selected from

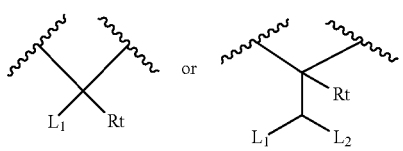

with $L_1$ being a five membered or six membered aromatic heterocycle or 3-7 membered non-aromatic heterocycle,
with Rt being selected from H or $C_1$-$C_4$ alkyl,
with $L_2$ being
f) with $X^1$ being BA-CONR$^8$— with BA being selected from

with $R^2$ and $R^3$ being selected, where applicable, independently from each other from —H, —F, —CN, —OH, a substituted or unsubstituted $C_1$-$C_3$ alkyl, a substituted or unsubstituted $C_1$-$C_3$ alkoxy, or a $C_1$-$C_3$ haloalkyl, with $R^2$ and $R^3$ optionally being selected, where applicable, independently from each other from —H, —F, —CN, —OH, —$CH_3$, —$CH_2CH_3$, —$OCH_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, with E being,
a substituted or unsubstituted C$_1$-C$_{16}$ alkyl, a substituted or unsubstituted C$_2$-C$_{16}$ alkenyl, a substituted or unsubstituted C$_2$-C$_{16}$ alkynyl,
a substituted or unsubstituted C$_3$-C$_{10}$ heterocycle,
a substituted or unsubstituted C$_5$-C$_{10}$ heteroaryl, or
a substituted or unsubstituted C$_6$-C$_{10}$ aryl;
f) with each R$^8$ being H, and
g) with T being
—CO$_2$H.

2. The compound according to claim 1, wherein independently from each other XB, XD, XE and XF are one, two, three or four N and one, two, three or four CR$^{10}$, CR$^{11}$, CR$^{13}$ and CR$^{14}$, respectively.

3. The compound according to claim 1, wherein
one or two of XB is N and none of XD, XE, XF is N, or
one or two of XD is N and none of XB, XE, XF is N, or
one or two of XE is N and none of XB, XD, XF is N, or
one or two of XF is N and none of XB, XD, XE is N.

4. The compound according to claim 1, wherein
one or two of XB is N and one or two of XD is N and none of XE, XF is N, or
one or two of XB is N and one or two of XE is N and none of XD, XF is N, or
one or two of XB is N and one or two of XF is N and none of XD, XE is N, or
one or two of XD is N and one or two of XE is N and none of XB, XF is N, or
one or two of XD is N and one or two of XF is N and none of XB, XE is N, or
one or two of XE is N and one or two of XF is N and none of XB, XD is N.

5. The compound according to claim 1, wherein
one or two of XB is N, one or two of XD is N and one or two of XE is N and none of XF is N, or
one or two of XB is N, one or two of XD is N and one or two of XF is N and none of XE is N, or
one or two of XB is N, one or two of XE is N and one or two of XF is N and none of XD is N, or
one or two of XD is N, one or two of XE is N and one or two of XF is N and none of XB is N.

6. The compound according to claim 1, wherein each R$^{10}$, R$^{11}$, R$^{13}$ and R$^{14}$ independently from being selected from —OH, —F, —OCH$_3$, —OC$_2$H$_5$, —OC$_3$H$_7$, —OCF$_3$, —CF$_3$ or —(CH$_2$)m-OR$_a$,
with Ra being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$ —CH$_2$C$_6$H$_5$, and
with m being selected from 1 or 2.

7. The compound according to claim 1, wherein moiety L$_1$ is a five membered aromatic N-heterocycle selected from a group comprising substituted or unsubstituted:
pyrroles, imidazoles, pyrazoles, triazoles, or tetrazoles;
pyrazolones, triazolones, imidazolones, or pyrrolidones,
thiadiazoles, thiazoles, isothiazoles, or thiazolidinediones; or
isoxazoles, oxazoles, or oxadiazoles.

8. The compound according to claim 1, wherein L$_1$ is a triazole.

9. The compound according to claim 1, wherein L$_1$ is a five membered non-aromatic N-heterocycle selected from a group comprising substituted or unsubstituted:
pyrrolidines or pyrazolidines,
hydantoines, imidazolidinones, isoxazolidines, or oxazolidinones, and
isothiazolidines, or isothiazolinone.

10. The compound according to claim 1, having a molecular structure as defined by the general formula (5)

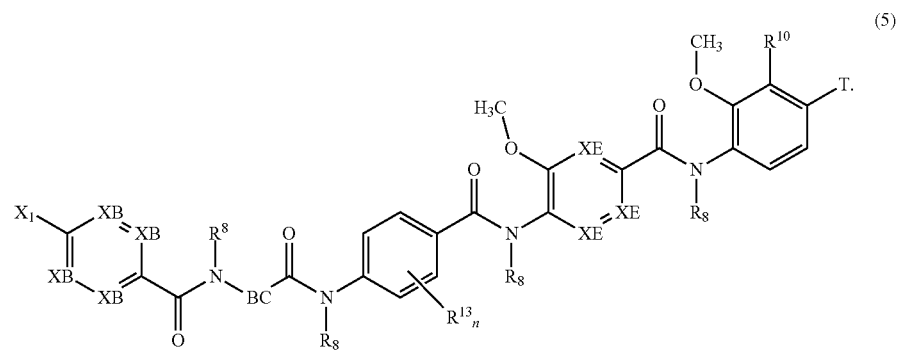

(5)

11. The compound according to claim 1, having a molecular structure as defined by the general formula (6)

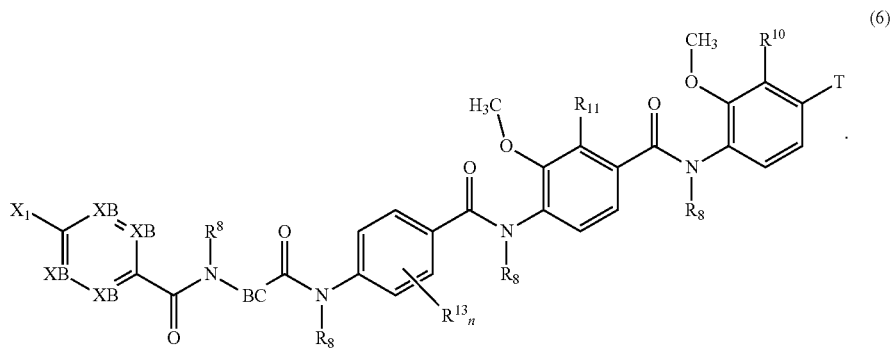

(6)

12. The compound according to claim 1, wherein $X^1$ is BA-CONHR$^8$—, with BA being BA1, and with E being

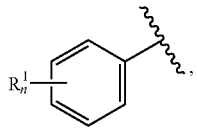

with n of $R^1_n$ being 0, 1, 2, 3, 4 or 5, and
with each $R^1$ independently from any other $R^1$ being selected from —OH, —F, —Cl, —Br, I, —CCH, —CN, —N$_3$, —OCH$_3$, —OC$_2$H$_5$, —OC$_3$H$_7$.

13. A method of treating a disease of bacterial infections by gram-negative or gram-positive bacterial strains, wherein the bacterial infection is an infection by one of the genus *Acinetobacter, Bacillus, Escherichia, Klebisella, Micrococcus, Mycobacterium, Pseudomonas*, or *Salmonella*, the method comprising administering to a subject the compound according to claim 1.

14. The compound according to claim 1, wherein:
each $R^{10}$, $R^{11}$, $R^{13}$ and $R^{14}$ being selected independently from H, —OH, —F, —OCH$_3$, —OC$_2$H$_5$, —OiC$_3$H$_7$, —OnC$_3$H$_7$, —OCF$_3$ or —CF$_3$;

the —C$_1$-C$_6$ alkyl is —CH$_3$ or —CH$_2$CH$_3$;
each $R^2$ and $R^3$ being selected independently from each other from —H, —F, —OCH$_3$ or —CH$_3$; and
with E being:
a substituted or unsubstituted C$_1$-C$_8$ alkyl, a substituted or unsubstituted C$_2$-C$_8$ alkenyl, a substituted or unsubstituted C$_2$-C$_8$ alkynyl, a substituted or unsubstituted C$_3$-C$_{10}$ cycloalkyl, or a substituted or unsubstituted C$_4$-C$_{10}$ heterocycle.

15. The compound according to claim 6, wherein one of $R^{10}$, $R^{11}$ and $R^{13}$ is —OH, OCH$_3$, —OC$_2$H$_5$ or —OiPr.

16. The compound according to claim 7, wherein L$_1$ is substituted or unsubstituted: 3H-pyrazol-3-ones, 4H-pyrazol-4-ones, 1,2-dihydro-3H-pyrazol-3-ones, 2,4-dihydro-3H-pyrazol-3-ones, 1,2,4-triazol-3-ones, 1,3,4-thiadiazoles, 1,3,4-oxadiazoles or 1,2,4-oxadiazoles.

17. The compound according to claim 9, wherein L$_1$ is substituted or unsubstituted: imidazolidin-4-ones, or 1,3,-oxazolidin-2-ones.

18. The compound according to claim 12, wherein R1 is OiPr, —OCF3, —NH2, —NHCH3, —N(CH3)2, —CH3, —CH2-CH3, —CF3, —OCONH2, —NO$_2$, —OCH2O—, —O—PO3H2, —O—PO3RaH —O—PO3Ra2 or —(CH2)m-ORa.

* * * * *